United States Patent
Czechtizky et al.

(10) Patent No.: US 9,440,941 B2
(45) Date of Patent: Sep. 13, 2016

(54) SUBSTITUTED CHROMAN-6-YLOXY-CYCLOALKANES AND THEIR USE AS PHARMACEUTICALS

(71) Applicant: SANOFI, Paris (FR)

(72) Inventors: Werngard Czechtizky, Frankfurt am Main (DE); John Weston, Frankfurt am Main (DE); Nils Rackelmann, Frankfurt am Main (DE); Volker Kraft, Frankfurt am Main (DE); Petra Arndt, Frankfurt am Main (DE); Klaus Wirth, Frankfurt am Main (DE); Heinz Goegelein, Frankfurt am Main (DE); Olaf Ritzeler, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/772,375

(22) PCT Filed: Mar. 7, 2014

(86) PCT No.: PCT/EP2014/054417
§ 371 (c)(1),
(2) Date: Sep. 2, 2015

(87) PCT Pub. No.: WO2014/135674
PCT Pub. Date: Sep. 12, 2014

(65) Prior Publication Data
US 2016/0016928 A1  Jan. 21, 2016

(30) Foreign Application Priority Data
Mar. 8, 2013 (EP) .................................. 13305263

(51) Int. Cl.
| | | |
|---|---|---|
| *C07D 311/60* | (2006.01) | |
| *C07F 9/655* | (2006.01) | |
| *C07D 409/12* | (2006.01) | |
| *C07D 413/12* | (2006.01) | |
| *C07D 405/12* | (2006.01) | |
| *C07D 417/12* | (2006.01) | |
| *C07D 417/14* | (2006.01) | |
| *C07D 407/14* | (2006.01) | |
| *C07D 407/12* | (2006.01) | |

(52) U.S. Cl.
CPC .......... *C07D 311/60* (2013.01); *C07D 405/12* (2013.01); *C07D 407/12* (2013.01); *C07D 407/14* (2013.01); *C07D 409/12* (2013.01); *C07D 413/12* (2013.01); *C07D 417/12* (2013.01); *C07D 417/14* (2013.01); *C07F 9/65522* (2013.01)

(58) Field of Classification Search
None
See application file for complete search history.

(56) References Cited

U.S. PATENT DOCUMENTS

| | | |
|---|---|---|
| 8,912,224 B2 | 12/2014 | Czechtizky et al. |
| 2014/0243292 A1 | 8/2014 | Czechtizky et al. |
| 2015/0087648 A1 | 3/2015 | Czechtizky et al. |

FOREIGN PATENT DOCUMENTS

| | | |
|---|---|---|
| EP | 0978506 A1 | 9/2000 |
| JP | 2008-189592 A | 8/2008 |
| WO | 97/09306 A1 | 3/1997 |
| WO | 02/32883 A1 | 4/2002 |
| WO | 03/006452 A1 | 1/2003 |
| WO | 04/000813 A1 | 12/2003 |
| WO | 2004/063191 A1 | 7/2004 |
| WO | 2009/115238 A1 | 9/2009 |
| WO | 2010/039474 A1 | 8/2010 |

OTHER PUBLICATIONS

Antoons, G. et al., "Alternative strategies in arrhythmia therapy: Evaluation of Na/Ca exchange as an anti-arrhythmic target", Pharmacology & Therapeutics (2012), vol. 134, pp. 26-42.
Bers, D. M. et al., "Regulation of Ca2+ and Na+ in Normal and Failing Cardiac Myocytes", Annals New York Academy of Sciences (2006), vol. 1080, pp. 165-177.
Dickstein, K. et al., "ESC Guidelines for the diagnosis and treatment of acute and chronic heart failure 2008", European Journal of Heart Failure (2008), pp. 933-989.
Flesch, M. et al., "Evidence for Functional Relevance of an Enhanced Expression of the Na+—Ca2+ Exchanger in Failing Human Myocardium", Circulation (1996), vol. 94, pp. 992-1002.
Hasenfuss, G. et al., "Relationship Between Na+—Ca2+—Exchanger Protein Levels and Diastolic Function of Failing Human Myocardium", Circulation (1999), vol. 99, pp. 641-648.
Kumara Swamy, K.C. et al., "Mitsunobu and Related Reactions: Advances and Applications", Chemical Reviews (2009), vol. 109, pp. 2551-2651.

(Continued)

*Primary Examiner* — Brian J Davis
(74) *Attorney, Agent, or Firm* — McDonnell Boehnen Hulbert & Berghoff

(57) ABSTRACT

The present invention relates to substituted chroman-6-yloxy-cycloalkanes of the formula (I) in which Ar, R1 to R4, p and q are as defined in the claims. The compounds of the formula (I) are inhibitors of the sodium-calcium exchanger (NCX), especially of the sodium-calcium exchanger of subtype 1 (NCX1), and are suitable for the treatment of diverse disorders in which intracellular calcium homeostasis is disturbed, such as arrhythmias, heart failure and stroke. The invention furthermore relates to processes for the preparation of the compounds of the formula (I), their use as pharmaceuticals, and pharmaceutical compositions comprising them.

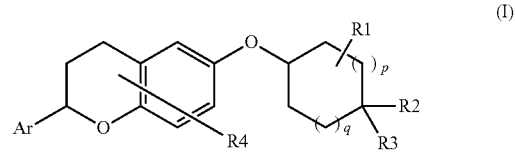

18 Claims, No Drawings

(56) References Cited

OTHER PUBLICATIONS

Matsuda, T. et al., "SEA0400, a Novel and Selective Inhibitor of the Na+—Ca2+ Exchanger, Attenuates Reperfusion Injury in the in Vitro and in Vivo Cerebral Ischemic Models", Journal of Pharmacology and Experimental Therapeutics (2001), vol. 298, pp. 249-256.

Mitsunobu, O., "The Use of Diethyl Azodicarboxylate and Triphenylphosphine in Synthesis and Transformation of Natural Products", Synthesis (1981), pp. 1-28.

Parissis, J.T. et al., "Inotropes in cardiac patients: update 2011", Current Opinion in Critical Care (2010), vol. 16, pp. 432-441.

Pott, C. et al., "Triple Threat: The Na+/Ca2+ Exchanger in the Pathophysiology of Cardiac Arrhythmia, Ischemia and Heart Failure", Current Drug Targets (2011), vol. 12, pp. 737-747.

Savelieva, I. et al., "Atrial fibrillation and heart failure: natural history and pharmacological treatment", Europace (2004), vol. 5., pp. S5-S19.

Schotten, U. et al., "Atrial fibrillation-induced atrial contractile dysfunction: a tachycardiomyopathy of a different sort", Cardiovascular Research (2002), vol. 53, pp. 192-201.

Sipido, K.R. et al., "[Ca2+]i-dependent membrane currents in guinea-pig ventricular cells in the absence of Na/Ca exchange", Pflügers Archiv—European Journal of Physiology (1995), vol. 430, pp. 871-878.

Verkerk, A.O. et al., "Ionic Mechanism of Delayed Afterdepolarizations in Ventricular Cells Isolated From Human End-Stage Failing Hearts", Circulation (2001), vol. 104, pp. 2728-2733.

European Search Report for EP13305263.9 dated Jun. 14, 2013 (mailed Jun. 21, 2013), pp. 1-4.

International Search Report (ISR) with Written Opinion for PCT/EP2014/054417 dated Apr. 19, 2014 (mailed Apr. 25, 2014), pp. 1-9.

SUBSTITUTED CHROMAN-6-YLOXY-CYCLOALKANES AND THEIR USE AS PHARMACEUTICALS

This application is a national stage application under 35 U.S.C. §371 of International Application No. PCT/EP2014/054417, filed Mar. 7, 2014, which claims the priority of European Application No. 13305263.9 filed on Mar. 8, 2013.

The present invention relates to substituted chroman-6-yloxy-cycloalkanes of the formula I,

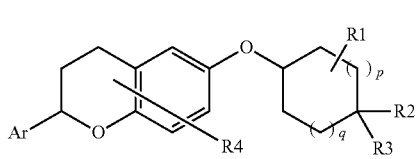

in which Ar, R1 to R4, p and q are as defined below. The compounds of the formula I are inhibitors of the sodium-calcium exchanger (NCX), especially of the sodium-calcium exchanger of subtype 1 (NCX1), and are suitable for the treatment of diverse disorders in which intracellular calcium homeostasis is disturbed, such as arrhythmias, heart failure and stroke. The invention furthermore relates to processes for the preparation of the compounds of the formula I, their use as pharmaceuticals, and pharmaceutical compositions comprising them.

Over the last decade major pharmacologic advances have been realized in the management of heart failure (HF), or congestive heart failure (CHF). Beta-blockers and inhibitors of the renin-angiotensin-aldosterone system have been found to have a favorable effect in CHF with regard to mortality and improvement of symptoms (K. Dickstein et al., Eur. J. Heart Fail. 10 (2008): 933-989). Nevertheless, morbidity and mortality have remained unacceptably high. The number of patients with CHF, and in particular more severe forms of CHF, is even growing, in part paradoxically because of the success of these treatment approaches. Thus, there is still a need for agents that can help improve CHF outcome and enhance quality of life. Blockers of the sodium-calcium exchanger (NCX), a transport protein which is involved in the regulation of cellular calcium and sodium levels, have the potential to improve the prognosis of CHF and quality of life.

The function of the NCX is to extrude calcium in cardiomyocytes and other cell types such as neurons. In CHF, the NCX was shown to be upregulated, thus unloading the cell from calcium and further decreasing myocardial contractility (M. Flesch et al., Circulation 94 (1996): 992-1002; G. Hasenfuss et al., Circulation 99 (1999): 641-648). Pump failure in CHF is not only due to irreversible structural changes and loss of myocardium, but also due to adverse functional changes including a disturbance of the intracellular calcium homeostasis. The latter can be treated by inhibition of the NCX. Three subtypes of the NCX have been described. In the heart, predominantly subtype 1 is expressed.

Through the NCX, calcium is exchanged for sodium, and extracellular sodium is the driving force for the exchanger. The stoichiometry of the exchanger is that three sodium ions enter the cell for the extrusion of one calcium ion. This stoichiometry causes a positive inward current which is depolarizing in nature. The depolarizing current, if of a sufficient size, could induce afterdepolarizations of the ventricular and atrial action potential. Afterdepolarizations are oscillations of the electric membrane potential and can occur during (early afterdepolarizations, EADs) or after (delayed afterdepolarizations, DADs) the cardiac action potential. The occurrence of EADs is associated with a prolonged ventricular action potential (visible as prolonged QT interval in the electrocardiogram (ECG)), which is a common feature of the failing heart. Afterdepolarizations are believed to be the major trigger of cardiac arrhythmias, which therefore are also called triggered activity (D. M. Bers et al., Ann. N. Y. Acad. Sci. 1080 (2006): 165-177; K. R. Sipido et al., Pflugers Arch. 430 (1995): 871-878; A. O. Verkerk et al., Circulation 104 (2001): 2728-2733; C. Pott et al., Current Drug Targets 12 (2011): 737-747; G. Antoons et al., Pharmacol. Ther. 134 (2012): 26-42). The premature beats arising from the NCX-induced depolarizing currents can cause more complex and irreversible arrhythmias such as episodes of tachycardia, ventricular flutter or ventricular fibrillation.

Patients with pump failure, or heart failure, typically suffer from arrhythmias and arrhythmic death. About 50% of the cardiac mortality in CHF is due to arrhythmic death. NCX blockade is therefore a means of improving pump failure and associated symptoms as well as of reducing arrhythmic death. Current positive inotropic drugs are associated with proarrhythmic effects that either increase mortality, such as in the case of phosphodiesterase inhibitors, or annihilate the positive effects achieved by an improvement of pump failure by the positive inotropic effect (J. T. Parissis et al., Curr. Opin. Crit. Care 16 (2010): 432-441). On the other hand, a number of clinically useful antiarrhythmic drugs have a negative inotropic effect on the heart worsening the symptoms of heart failure. NCX blockers are therapeutically unique in that they can address the two major problems of CHF, pump failure and arrhythmias.

NCX blockade is particularly interesting for advanced stages of CHF, like NYHA Classes III and IV according to the New York Heart Association Functional Classification of heart failure, in which the therapeutic options, i.e. beta-blockers, inhibitors of the renin angiotensin-aldosterone system, diuretics and vasodilators, already are fully exploited. Elderly patients progressing to end-stage HF present a new emerging population. In this late stage a vasodilator effect is no more desirable in a considerable part of the patients because blood pressure is already lowered as a consequence of pump failure. Phosphodiesterase inhibitors as positive inotropic drugs not only suffer from the drawback of being proarrhythmic, but also from a vasodilator effect.

Atrial fibrillation (AF) is the most frequent arrhythmia. AF affects about 6.8 million patients in the US and the European Union, and its prevalence is strongly rising because of the aging of the population and of the successful treatment of myocardial infarction, coronary artery disease and congestive heart failure. AF causes about 25% of all strokes, and increases mortality. Also in AF, upregulation of the NCX has been demonstrated (U. Schotten et al., Cardiovasc. Res. 53 (2002): 192-201). Upregulation of the NCX can be involved in the induction of AF by the arrhythmogenic activity of the NCX and in its maintenance, and hence NCX blockers have therapeutically favorable effects in the therapy and prevention of AF. Since AF is an increasing disease in the aging population and is frequently associated with heart failure in up to about 45% of patients (I. Savelieva et al., Europace 5 Suppl 1 (2004): S5-S19), NCX blockers would be particularly favorable in patients with AF and CHF.

Since NCX blockers also exert a positive inotropic effect in the atria, they may be particularly favorable in diastolic heart failure where ventricular filling is the major problem as a consequence of ventricular stiffening. A more vigorous atrial contraction would improve ventricular filling in diastolic heart failure.

Since a reduced cardiac output has deleterious effects on the perfusion of organs such as the kidney, brain and heart, inhibition of the NCX, which increases the contractility of the heart, is able to improve perfusion of the brain, heart and kidney for a therapy or prevention of stroke, dementia and Alzheimer's disease, renal failure and cardiac ischemia. Since the NCX is also involved in salt sensitive hypertension, its inhibition is also suited for the treatment of hypertension.

Inhibitors of the NCX are also suited for the therapy and prevention of life threatening conditions in which inotropic support is required to maintain a sufficient level of blood supply. This includes all forms of shock, hemodynamic shock, cardiogenic shock and septic shock. Inhibitors of the NCX are particularly suited to treat these conditions because they are neutral on heart rate and lack the proarrhythmic or vasodilator or vasoconstrictor properties of other inotropic drugs.

In stroke, NCX blockers have the potential of improving the outcome since in neuronal hypoxia, as occurs in stroke, the NCX reverses its transport direction to reverse mode, and loads the cells with calcium leading to a calcium overload. This leads to accelerated cell death due to excessive intracellular calcium concentrations. Moreover, a low cardiac output can lead to brain ischemia favoring stroke. NCX blockers will increase cardiac output and raise brain perfusion. Hence, NCX blockers have a potential in the therapy and prevention of stroke (T. Matsuda et al., J. Pharmacol. Exp. Ther. 298 (2001): 249-256).

Certain compounds capable of inhibiting the NCX have already been described, e.g. in EP 0978506, JP 2008/189592, WO 2004/000813, WO 2004/063191, WO 03/006452, WO 02/32883, WO 97/09306. However, there still is a need for further compounds which inhibit the NCX and are suitable for use as pharmaceuticals in the treatment of the mentioned disease states. It has now been found that the compounds of the formula I are excellent inhibitors of the sodium-calcium exchanger (NCX), especially of the sodium-calcium exchanger of subtype 1 (NCX1), and have a favorable property profile for such use.

Thus, a subject of the present invention are the compounds of the formula I, in any of their stereoisomeric forms and mixtures of stereoisomeric forms in any ratio, and the pharmaceutically acceptable salts thereof,

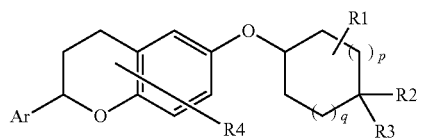

I wherein

Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_3-C_7)$-cycloalkyl-$(C_1-C_4)$-alkyl-, HO—, $(C_1-C_6)$-alkyl-O—, $(C_3-C_7)$-cycloalkyl-O— and $(C_3-C_7)$-cycloalkyl-$(C_1-C_4)$-alkyl-O—, and two groups R0 bonded to adjacent ring carbon atoms in Ar, together with the carbon atoms carrying them, can form a 5-membered to 7-membered mono-unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of fluorine and $(C_1-C_4)$-alkyl;

R1 is hydrogen or one or more identical or different substituents selected from the series consisting of fluorine and $(C_1-C_4)$-alkyl;

R2 is selected from the series consisting of hydrogen, $(C_1-C_6)$-alkyl, HO—, $(C_1-C_6)$-alkyl-O—, $(C_1-C_6)$-alkyl-C(O)—O—, phenyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, wherein $(C_1-C_6)$-alkyl is unsubstituted or substituted by one or more identical or different substituents R20;

R3 is selected from the series consisting of hydrogen and $(C_1-C_6)$-alkyl, wherein $(C_1-C_6)$-alkyl is unsubstituted or substituted by one or two identical or different substituents selected from the series consisting of $(C_3-C_7)$-cycloalkyl, phenyl, HO— and $(C_1-C_4)$-alkyl-O—;

or the groups R2 and R3 together are oxo;

R4 is hydrogen or one or more identical or different substituents selected from the series consisting of halogen, $(C_1-C_4)$-alkyl and $(C_1-C_4)$-alkyl-O—;

R5 and R6 are independently of one another selected from the series consisting of hydrogen, $(C_1-C_6)$-alkyl, $(C_2-C_6)$-alkenyl, $(C_3-C_7)$-cycloalkyl, $(C_6-C_{10})$-bicycloalkyl, phenyl, Het1 and Het2, wherein $(C_1-C_6)$-alkyl is unsubstituted or substituted by one or more identical or different substituents R20, and $(C_3-C_7)$-cycloalkyl, $(C_6-C_{10})$-bicycloalkyl and Het2 all are unsubstituted or substituted by one or more identical or different substituents R21, and phenyl and Het1 all are unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of $(C_1-C_6)$-alkyl, $(C_3-C_7)$-cycloalkyl, phenyl, Het1 and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, and phenyl and Het1 all are unsubstituted or substituted by one or more identical or different substituents R22;

R8 is selected from the series consisting of hydrogen and $(C_1-C_4)$-alkyl;

R9 is selected from the series consisting of $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R10 is selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R20 is selected from the series consisting of R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R22 is selected from the series consisting of halogen, $(C_1-C_4)$-alkyl, HO—$(C_1-C_4)$-alkyl-, $(C_3-C_7)$-cycloalkyl, HO—, oxo, $(C_1-C_6)$-alkyl-O—, $(C_3-C_7)$-cycloalkyl-O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, R33-O—C(O)—N(R32)-, $(C_1-C_6)$-alkyl-S(O)$_2$—N(R32)-, NC—, R33-C(O)—, R31-N(R32)-C(O)—, R34-O—C(O)— and R31-N(R32)-S(O)$_2$—;

R24 is a 3-membered to 10-membered, monocyclic or bicyclic ring which is saturated, partially unsaturated or aromatic and comprises 0, 1, 2, 3 or 4 identical or different ring heteroatoms selected from the series consisting of nitrogen, oxygen and sulfur, and which is unsubstituted or substituted by one or more identical or different substituents R22;

R30 and R33 are independently of one another selected from the series consisting of $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R31 and R32 are independently of one another selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-, or the groups R31 and R32, together with the nitrogen atom carrying them, form a 4-membered to 7-membered, monocyclic saturated heterocycle which, in addition to the nitrogen atom carrying R31 and R32, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl;

R34 is selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

Het1 is a 5-membered or 6-membered, monocyclic, aromatic heterocycle which comprises 1, 2 or 3 identical or different ring heteroatoms selected from the series consisting of nitrogen, oxygen and sulfur, and which is unsubstituted or substituted by one or more identical or different substituents selected from the series consisting of halogen, $(C_1-C_4)$-alkyl and $(C_1-C_4)$-alkyl-O—, unless specified otherwise;

Het2 is a 4-membered to 10-membered, monocyclic or bicyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, $(C_1-C_4)$-alkyl and $(C_1-C_4)$-alkyl-O—, unless specified otherwise;

wherein all cycloalkyl and bicycloalkyl groups, independently of any other substituents which can be present on a cycloalkyl or bicycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

If the group R1 is hydrogen, the carbon atoms of the cycloalkane ring in the compounds of the formula I and all other compounds in which R1 occurs, carry hydrogen atoms only, apart from the groups R2 and R3 and the oxygen atom linking the cycloalkane ring to the chroman ring. Groups R1 in the compounds of the formula I and all other compounds in which R1 occurs, which are different from hydrogen, i.e. fluorine and $(C_1-C_4)$-alkyl substituents representing R1, can be bonded to any of the ring carbon atoms of the cycloalkane ring depicted in formula I which has a free binding site, i.e. to any ring carbon atom of the cycloalkane ring except for the ring carbon atom carrying the groups R2 and R3, as is indicated by the bond originating at R1 which is not directed to a specific carbon atom. Likewise, if the group R4 is hydrogen, the chroman ring in the compounds of the formula I and all other compounds in which R4 occurs, carries hydrogen atoms only, apart from the group Ar and the oxygen atom linking the chroman ring to the cycloalkane ring. Groups R4 in the compounds of the formula I and all other compounds in which R4 occurs, which are different from hydrogen, i.e. halogen, $(C_1-C_4)$-alkyl and $(C_1-C_4)$-alkyl-O— substituents representing R4, can be bonded to any of the carbon atoms of the chroman ring depicted in formula I which have a free binding site, i.e. to the carbon atoms in ring positions 2, 3, 4, 5, 7 and 8 of the chroman ring as identified in formula I', as is indicated by the bond originating at R4 which is not directed to a specific carbon atom of the chroman ring.

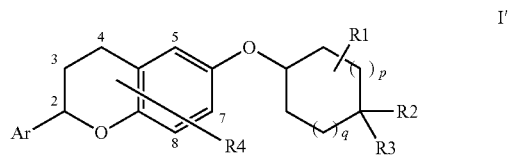

In all free binding sites of the carbon atoms in ring positions 2, 3, 4, 5, 7 and 8 of the chroman ring which are not occupied by groups R4 different from hydrogen, as well as in all free binding sites of the cycloalkane ring which are not occupied by groups R1 different from hydrogen, hydrogen atoms are present. I.e., if in a compound of the formula I no group R4 is present which is different from hydrogen, the carbon atoms in ring positions 2, 5, 7 and 8 of the chroman ring carry one hydrogen atom, and the carbon atoms in ring positions 3 and 4 of the chroman ring carry two hydrogen atoms. If in a compound of the formula I no group R1 is present which is different from hydrogen, the ring carbon atom of the cycloalkane ring which carries the oxygen atom linked to the chroman ring, carries one hydrogen atom, and the other ring carbon atoms apart from the atom carrying R2 and R3 carry two hydrogen atoms. Compounds of the formula I in which no group R4 and/or no group R1 is present which is different from hydrogen, may alternatively be represented by a modified formula I in which R4 and/or R1 and the bond originating at them are omitted. If substituents R4 and/or R1 are present, i.e. atoms or groups representing R4 and/or R1 which are different from hydrogen, one or more of the said hydrogen atoms are replaced by the substituents.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO— substituted alkyl group (HO-alkyl-, hydroxyalkyl group). Depending on the respective definition, the number of carbon atoms in an alkyl group can be 1, 2, 3, 4, 5 or 6, or 1, 2, 3 or 4, or 1, 2 or 3, or 1 or 2, or 1. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Examples of alkyl-O— groups are methoxy, ethoxy, n-propoxy, isopropoxy, n-butoxy, isobutoxy, tert-butoxy, n-pentoxy. Examples of alkyl-$S(O)_n$— are methylsulfanyl-($CH_3$—S—), methanesulfinyl-($CH_3$—S(O)—), methanesulfonyl ($CH_3$—$S(O)_2$—), ethylsulfanyl-($CH_3$—$CH_2$—S—), ethanesulfinyl-($CH_3$—$CH_2$—S(O)—), ethanesulfonyl ($CH_3$—$CH_2$—$S(O)_2$—), 1-methylethylsulfanyl-(($CH_3$)$_2$CH—S—), 1-methylethanesulfinyl-(($CH_3$)$_2$CH—S(O)—), 1-methylethanesulfonyl (($CH_3$)$_2$CH—$S(O)_2$—). In one embodiment of the invention, the number n is selected from the series consisting of 0 and 2, wherein all numbers n are independent of each other and can be identical or different. In another embodiment the number n in any of its occurrences, independent of its meaning in other occurrences, is 0. In another embodiment the number n in any of its occurrences, independent of its meaning in other occurrences, is 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. As examples of substituted alkyl groups, specifically of HO—($C_1$-$C_4$)-alkyl-groups, for example, hydroxymethyl, 1-hydroxyethyl, 2-hydroxyethyl, 1-hydroxypropyl, 2-hydroxypropyl, 3-hydroxypropyl, 1-hydroxy-1-methylethyl, 2-hydroxy-1-methylethyl, 1-hydroxybutyl, 4-hydroxybutyl, 2-hydroxy-1-methylpropyl or 2-hydroxy-1-methylpropyl may be mentioned.

Independently of any other substituents which can be present on an alkyl group, and unless specified otherwise, alkyl groups can be substituted by one or more fluorine substituents, for example by 1, 2, 3, 4, 5, 6, 7, 8, 9, 10 or 11 fluorine substituents, or by 1, 2, 3, 4 or 5 fluorine substituents, or by 1, 2 or 3 fluorine substituents, which can be located in any positions. I.e., independently of any other substituents which can be present on an alkyl group, an alkyl group can be unsubstituted by fluorine substituents, i.e. not carry fluorine substituents, or substituted by fluorine substituents, wherein all alkyl groups in the compounds of the formula I are independent of one another with regard to the optional substitution by fluorine substituents. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-$S(O)_n$— groups are trifluoromethylsulfanyl-($CF_3$—S—), trifluoromethanesulfinyl-($CF_3$—S(O)—) and trifluoromethanesulfonyl ($CF_3$—$S(O)_2$—). With respect to all groups or substituents in the compounds of the formula I which can be an alkyl group which can generally contain one or more fluorine substituents, as an example of groups or substituents containing fluorine-substituted alkyl which may be included in the definition of the group or substituent, the group $CF_3$ (trifluoromethyl), or respective groups such as $CF_3$—O— or $CF_3$—S—, may be mentioned.

The above explanations with respect to alkyl groups apply correspondingly to alkyl groups which in the definition of a group in the compounds of the formula I are bonded to two adjacent groups, or linked to two groups, and may be regarded as divalent alkyl groups (alkanediyl groups), like in the case of the alkyl part of a substituted alkyl group. Thus, such groups can also be linear or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are —$CH_2$—, —$CH_2$—$CH_2$—, —$CH_2$—$CH_2$—$CH_2$—, —$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—. Examples of fluoro-substituted alkanediyl groups, which can contain 1, 2, 3, 4, 5 or 6 fluorine substituents, for example, are —CHF—, —$CF_2$—, —$CF_2$—$CH_2$—, —$CH_2$—$CF_2$—, —$CF_2$—$CF_2$—, —CF($CH_3$)—, —C($CF_3$)$_2$—, —C($CH_3$)$_2$—$CF_2$—, —$CF_2$—C($CH_3$)$_2$—.

The above explanations with respect to alkyl groups apply correspondingly to unsaturated hydrocarbon residues, i.e. alkenyl groups, which in one embodiment of the invention contain one double bond. Thus, for example, alkenyl groups can likewise be linear or branched. Double bonds can be present in any positions. The number of carbon atoms in an alkenyl group can be 2, 3, 4, 5 or 6, or 2, 3, 4 or 5, or 3, 4 or 5, for example. Examples of alkenyl are ethenyl (vinyl), prop-1-enyl, prop-2-enyl (allyl), but-2-enyl, but-3-enyl, 2-methylprop-2-enyl, 3-methylbut-2-enyl, hex-3-enyl, hex-4-enyl, 4-methylpent-3-enyl. In one embodiment of the invention, an alkenyl group contains at least three carbon atoms and is bonded to the remainder of the molecule via a carbon atom which is not part of a double bond.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. The number of ring carbon atoms in a ($C_6$-$C_{10}$)-bicycloalkyl group can be 6, 7, 8, 9 or 10. The two cycles in a bicycloalkyl group can have one, two or more ring carbon atoms in common and can be fused or form a bridged bicycle or a spirocycle. Examples of bicycloalkyl are bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.2.2]nonyl and bicyclo[4.4.0]decyl. Bicycloalkyl groups can be bonded via any ring carbon atom. Independently of any other substituents which can be present on a cycloalkyl group or bicycloalkyl group, and unless specified otherwise, cycloalkyl groups and bicycloalkyl groups can be substituted by one or more ($C_1$-$C_4$)-alkyl substituents, for example by 1, 2, 3 or 4 identical or different ($C_1$-$C_4$)-alkyl substituents, for example by methyl groups, which can be located in any positions. I.e., independently of any other substituents which can be present on a cycloalkyl group or bicycloalkyl group, cycloalkyl groups and bicycloalkyl groups can be unsubstituted by ($C_1$-$C_4$)-alkyl substituents, i.e. not carry ($C_1$-$C_4$)-alkyl substituents, or substituted by ($C_1$-$C_4$)-alkyl substituents, wherein all cycloalkyl groups and bicycloalkyl groups in the compounds of the formula I are independent of one another with regard to the optional substitution by ($C_1$-$C_4$)-alkyl substituents. Examples of such alkyl-substituted cycloalkyl groups and bicycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl, 3,3,5,5-tetramethylcyclohexyl, 7,7-dimethylbicyclo[2.2.1]heptyl, 6,6-dimethylbicyclo[3.1.1]heptyl and 1,7,7-trimethylbicyclo[2.2.1]heptyl.

Independently of any other substituents including ($C_1$-$C_4$)-alkyl substituents which can be present on a cycloalkyl group or bicycloalkyl group, and unless specified otherwise, cycloalkyl groups and bicycloalkyl groups can further be substituted by one or more fluorine substituents, for example by 1, 2, 3, 4, 5, 6, 7, 8, 9, 10 or 11 fluorine substituents, or by 1, 2, 3, 4 or 5 fluorine substituents, or by 1, 2 or 3 fluorine substituents, which can be located in any positions and can also be present in a ($C_1$-$C_4$)-alkyl substituent. I.e., independently of any other substituents which can be present on a cycloalkyl group or bicycloalkyl group, cycloalkyl groups and bicycloalkyl groups can be unsubstituted by fluorine substituents, i.e. not carry fluorine substituents, or substituted by fluorine substituents, wherein all cycloalkyl groups and bicycloalkyl groups in the compounds of the formula I are independent of one another with regard to the optional substitution by fluorine substituents. Examples of fluoro-substituted cycloalkyl groups and bicycloalkyl groups are 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl, 1-fluorobicyclo[2.2.2]octyl and 1,4-difluorobicyclo[2.2.2]octyl. Cycloalkyl groups can also be substituted simultaneously by fluorine and alkyl. Examples of the group ($C_3$-$C_7$)-cycloalkyl-($C_1$-$C_4$)-alkyl- are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. In one embodiment of the invention, a ($C_3$-$C_7$)-cycloalkyl-($C_1$-$C_4$)-alkyl-group in any one or more occurrences of such a group, independently of any other occurrences, is a ($C_3$-$C_7$)-cycloalkyl-($C_1$-$C_2$)-alkyl-group, in another embodiment a ($C_3$-$C_7$)-cycloalkyl-$CH_2$— group. In the group ($C_3$-$C_7$)-cycloalkyl-($C_1$-$C_4$)-alkyl-, and likewise in all other groups, the terminal hyphen denotes the free bond via which the group is bonded, and thus indicates via which subgroup a group composed of subgroups is bonded.

In substituted phenyl groups, including phenyl groups representing Ar and R24, the substituents can be located in any positions. In monosubstituted phenyl groups, the substituent can be located in position 2, in position 3 or in position 4. In disubstituted phenyl groups, the substituents can be located in positions 2 and 3, in positions 2 and 4, in positions 2 and 5, in positions 2 and 6, in positions 3 and 4, or in positions 3 and 5. In trisubstituted phenyl groups, the substituents can be located in positions 2, 3 and 4, in positions 2, 3 and 5, in positions 2, 3 and 6, in positions 2, 4 and 5, in positions 2, 4 and 6, or in positions 3, 4 and 5. If a phenyl group carries four substituents, some of which can be fluorine atoms, for example, the substituents can be located in positions 2, 3, 4 and 5, in positions 2, 3, 4 and 6, or in positions 2, 3, 5 and 6. If a polysubstituted phenyl group or any other polysubstituted group carries different substituents, each substituent can be located in any suitable position, and the present invention comprises all positional isomers. The number of substituents in a substituted phenyl group can be 1, 2, 3, 4 or 5. In one embodiment of the invention, the number of substituents in a substituted phenyl group, and likewise in other embodiments the number of substituents in any other substituted group which can carry one or more substituents, is 1, 2, 3 or 4, in another embodiment 1, 2 or 3, in another embodiment 1 or 2, in another embodiment 1, wherein the number of substituents in any occurrence of such a substituted group is independent of the number of substituents in other occurrences.

In heterocyclic groups, including the groups Het1 and Het2 and heterocyclic groups R24, and other heterocyclic rings which can be present in the compounds of the formula I, such as rings formed by two groups together with the atom or atoms carrying them, the hetero ring members can be present in any combination and located in any suitable ring positions, provided that the resulting group and the compound of the formula I are suitable and sufficiently stable as a pharmaceutical active compound. In one embodiment of the invention, two oxygen atoms in any heterocyclic ring in the compounds of the formula I cannot be present in adjacent ring positions. In another embodiment of the invention, two hetero ring members selected from the series consisting of oxygen atoms and sulfur atoms cannot be present in adjacent ring positions in any heterocyclic ring in the compounds of the formula I. In another embodiment of the invention, two hetero ring members selected from the series consisting of nitrogen atoms carrying an exocyclic group like a hydrogen atom or a substituent, sulfur atoms and oxygen atoms cannot be present in adjacent ring positions in any heterocyclic ring in the compounds of the formula I. In an aromatic heterocyclic ring the choice of hetero ring members is limited by the prerequisite that the ring is aromatic, i.e. it comprises a cyclic system of six delocalized pi electrons.

Monocyclic aromatic heterocycles are 5-membered or 6-membered rings and, in the case of a 5-membered ring, comprise one ring heteroatom selected from the series consisting of oxygen, sulfur and nitrogen, wherein this ring nitrogen carries an exocyclic group like a hydrogen atom or a substituent, and optionally one or more further ring nitrogen atoms, and, in the case of a 6-membered ring, comprise one or more nitrogen atoms as ring heteroatoms, but no oxygen atoms and sulfur atoms as ring heteroatoms. Unless specified otherwise in the definition of the group, heterocyclic groups can be bonded via any suitable ring atom, i.e. any ring atom which carries a hydrogen atom or a substituent, including ring carbon atoms and ring nitrogen atoms. In one embodiment of the invention, any of the heterocyclic groups occurring in the compounds of the formula I in any of its occurrences, is independently of its other occurrences and independently of any other heterocyclic group, bonded via a ring carbon atom, and in another embodiment via a ring nitrogen atom, if applicable. In substituted heterocyclic groups, the substituents can be located in any positions.

The number of ring heteroatoms which can be present in a heterocyclic group in the compounds of the formula I, the number of cycles, i.e. whether the heterocyclic group can be monocyclic and/or bicyclic, the number of ring members which can be present, and the degree of saturation, i.e. whether the heterocyclic group is saturated and does not contain a double bond within the ring, or whether it is partially unsaturated and contains one or more, for example one or two, double bonds within the ring but is not aromatic, or whether it is aromatic and thus contains two double bonds within the ring in the case of a 5-membered monocyclic aromatic heterocycle, three double bonds within the ring in the case of a 6-membered monocyclic aromatic heterocycle, four double bonds within the ring in the case of 9-membered bicyclic aromatic heterocycle, and five double bonds within the ring in the case of 10-membered aromatic heterocycle, is specified in the definitions of the individual groups in the compounds of the formula I. The two cycles in a bicyclic heterocyclic group can have one, two or more ring atoms in common and can be fused or form a bridged bicycle or a spirocycle. As examples of heterocyclic ring systems, from which heterocyclic groups in the compounds of the formula I can be derived, and from any one or more of which any of the heterocyclic groups in the compounds of the formula I, independently of any other heterocyclic group, is selected in one embodiment of the invention, provided that the ring system is comprised by the definition of the group, oxetane, thietane, azetidine, furan, tetrahydrofuran, thiophene, tetrahydrothiophene, pyrrole, pyrroline, pyrrolidine, 1,3-dioxole, 1,3-dioxolane, isoxazole ([1,2]oxazole), isoxazoline, isoxazolidine, oxazole ([1,3]oxazole), oxazoline, oxazolidine, isothiazole ([1,2]thiazole), isothiazoline, isothiazolidine, thiazole ([1,3]thiazole), thiazoline, thiazolidine, pyrazole, pyrazoline, pyrazolidine, imidazole, imidazoline, imidazolidine, [1,2,3]triazole, [1,2,4]triazole, [1,2,4]oxadiazole, [1,3,4]oxadiazole, [1,2,5]oxadiazole, [1,2,4]thiadiazole, 1H-tetrazole, pyran, tetrahydropyran, thiopyran, tetrahydrothiopyran, 2,3-dihydro[1,4]dioxine, 1,4-dioxane, pyridine, 1,2,5,6-tetrahydropyridine, piperidine, morpholine, thiomorpholine, piperazine, pyridazine, pyrimidine, pyrazine, [1,2,4]triazine, oxepane, thiepane, azepane, [1,3]diazepane, [1,4]diazepane, [1,4]oxazepane, [1,4]thiazepane, azocane, 3-azabicyclo[3.1.0]hexane, octahydrocyclopenta[b]pyrrole, octahydrocyclopenta[c]pyrrole, 2-azaspiro[4.4]nonane, 7-azabicyclo[2.2.1]heptane, 2,7-diazaspiro[4.4]nonane, octahydropyrrolo[3,4-b]pyrrole, 6,7-dihydro-5H-pyrrolo[2,1-c][1,2,4]triazole, imidazo[2,1-b]thiazole, 6,7-dihydro-5H-thiazolo[3,2-a]pyrimidine, benzofuran, isobenzofuran, benzothiophene (benzo[b]thiophene), 1H-indole, 2,3-dihydro-1H-indole, octahydroindole, 2H-isoindole, octahydroisoindole, benzo[1,3]dioxole, benzoxazole, benzthiazole, 1H-benzimidazole, imidazo[1,2-a]pyridine, [1,2,4]triazolo[4,3-a]pyridine, chroman, isochroman, thiochroman, benzo[1,4]dioxane, 3,4-dihydro-2H-benzo[1,4]oxazine, 3,4-dihydro-2H-benzo[1,4]thiazine, 2-azaspiro[4.5]decane, 3-azabicyclo[3.2.2]nonane, quinoline, 1,2,3,4-tetrahydroquinoline, 5,6,7,8-tetrahydroquinoline, isoquinoline, 1,2,3,4-tetrahydroisoquinoline, 5,6,7,8-tetrahydroisoquinoline, 2,7-diazaspiro[4.5]decane, 2,8-diazaspiro[4.5]decane, cinnoline, quinazoline, quinoxaline, phthalazine and [1,8]naphthyridine may be mentioned, which can all be unsubstituted or substituted in any suitable positions as specified in the definition of the respective group in the compounds of the formula I, wherein the given degree of unsaturation is by way of example only, and in the individual groups also ring systems with a higher or lower degree of saturation, or hydrogenation, or of unsaturation can be present as specified in the definition of the group.

As mentioned, the heterocyclic groups can be bonded via any suitable ring atom. For example, among others can an oxetane and a thietane ring be bonded via positions 2 and 3, an azetidine ring via positions 1, 2 and 3, a furan ring, a tetrahydrofuran ring, a thiophene ring and a tetrahydrothiophene via positions 2 and 3, a pyrrole ring and a pyrrolidine ring via positions 1, 2 and 3, an isoxazole ring and an isothiazole ring via positions 3, 4 and 5, a pyrazole ring via positions 1, 3, 4 and 5, an oxazole ring and a thiazole ring via positions 2, 4 and 5, an imidazole ring and an imidazolidine ring via positions 1, 2, 4 and 5, a 1H-tetrazole ring via positions 1 and 5, a tetrahydropyran and a tetrahydrothiopyran ring via positions 2, 3 and 4, a 1,4-dioxane ring via position 2, a pyridine ring via positions 2, 3 and 4, a piperidine ring via positions 1, 2, 3 and 4, a morpholine ring and a thiomorpholine ring via positions 2, 3 and 4, a piperazine ring via positions 1 and 2, a pyrimidine ring via positions 2, 4 and 5, a pyrazine ring via position 2, an azepane ring via positions 1, 2, 3 and 4, a 3-azabicyclo[3.1.0]hexane ring via positions 3 and 6, an octahydrocyclopenta[b]pyrrole and an octahydrocyclopenta[c]pyrrole ring via position 1, a 2-azaspiro[4.4]nonane ring via position 2, a 7-azabicyclo[2.2.1]heptane ring via position 7, an octahydropyrrolo[3,4-b]pyrrole ring via positions 1 and 5, a 6,7-dihydro-5H-pyrrolo[2,1-c][1,2,4]triazole ring via position 3, an imidazo[2,1-b]thiazole ring via positions 2, 5 and 6, a 6,7-dihydro-5H-thiazolo[3,2-a]pyrimidine via position 3, a benzofuran ring and a benzothiophene ring via positions 2, 3, 4, 5, 6 and 7, a 1H-indole ring, a 2,3-dihydro-1H-indole and an octahydroindole ring via positions 1, 2, 3, 4, 5, 6 and 7, a benzo[1,3]dioxole ring via positions 4, 5, 6 and 7, a benzoxazole ring and a benzthiazole ring via positions 2, 4, 5, 6 and 7, a 1H-benzimidazole ring via positions 1, 2, 4, 5, 6 and 7, an imidazo[1,2-a]pyridine ring via positions 2 and 3, a [1,2,4]triazolo[4,3-a]pyridine ring via position 3, a benzo[1,4]dioxane ring via positions 5, 6, 7 and 8, a 3-azabicyclo[3.2.2]nonane ring via position 3, a quinoline ring via positions 2, 3, 4, 5, 6, 7 and 8, a 1,2,3,4-tetrahydroquinoline ring via positions 1, 5, 6, 7 and 8, a 5,6,7,8-tetrahydroquinoline via positions 2, 3 and 4, an isoquinoline ring via positions 1, 3, 4, 5, 6, 7 and 8, a 1,2,3,4-tetrahydroisoquinoline ring via positions 2, 5, 6, 7 and 8, a 5,6,7,8-tetrahydroisoquinoline ring via positions 1, 3, 4 and 5, a 2,7-diazaspiro[4.5]decane ring via positions 2 and 7, a 2,8-diazaspiro[4.5]decane ring via positions 2 and 8, for example, wherein the resulting residues of the heterocyclic groups can all be unsubstituted or substituted in any suitable positions as specified for the respective group in the definition of the compounds of the formula I.

Halogen is fluorine, chlorine, bromine or iodine. In one embodiment of the invention, in any of its occurrences halogen is fluorine, chlorine or bromine, in another embodiment fluorine or chlorine, in another embodiment fluorine, in another embodiment chlorine, wherein all occurrences of halogen are independent of each other.

An oxo group, i.e. a doubly bonded oxygen atom, when occurring as a substituent on a carbon atom, replaces two hydrogen atoms on a carbon atom of the parent system. Thus, if a $CH_2$ group is substituted by oxo, it becomes a carbonyl group (C(O), C=O). Just so, if the groups R2 and R3 together are oxo, the group C(R2)-R3 in the cycloalkane ring depicted in formula I becomes a carbonyl group. Oxo groups can also occur on sulfur atoms, such as on ring sulfur atoms in saturated and partially unsaturated heterocycles in which generally, besides a ring sulfur atom, also an S(O) group (S(=O)) and an S(O)$_2$ group (S(=O)$_2$) can be present as hetero ring members. An oxo group cannot occur as a substituent on a carbon atom in an aromatic ring such as in a phenyl group.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example the carbon atom in position 2 of the chroman ring or in unsubstituted or substituted alkyl groups, can all independently of each other have S configuration or R configuration. The invention relates to enantiomers, both the levorotatory and the dextrorotatory antipode, in enantiomerically pure form and essentially enantiomerically pure form, for example with a molar ratio of the two enantiomers of 98:2, or 99:1, or greater, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 98:2, or 99:1, or greater, and in the form of mixtures of the cis isomer and the trans isomer in all ratios. Cis/trans isomerism can occur in substituted rings, for example. The preparation of individual stereoisomers, if desired, can be carried out by resolution of a mixture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound of the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomers of the intermediate into the enantiomeric forms of the final compound of the formula I, or by performing an enantioselective reaction in the course of the synthesis. The invention also comprises all tautomeric forms of the compounds of the formula I.

Besides the free compounds of the formula I, i.e. compounds in which acidic and basic groups are not present in the form of a salt, the present invention comprises also salts of the compounds of the formula I, in particular their physiologically acceptable salts, or toxicologically acceptable salts, or pharmaceutically acceptable salts, which can be formed on one or more acidic or basic groups in the compounds of the formula I, for example on basic heterocyclic moieties. The compounds of the formula I may thus be deprotonated on an acidic group and be used for example as alkali metal salts, for example sodium or potassium salts, or as ammonium salts, for example as salts with ammonia or organic amines or amino acids. Compounds of the formula I comprising at least one basic group may also be prepared and used in the form of their acid addition salts, for example in the form of pharmaceutically acceptable salts with inorganic acids and organic acids, such as salts with hydrochloric acid and thus be present in the form of the hydrochlorides, for example. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

In one embodiment of the invention, the group Ar is phenyl which is unsubstituted or substituted by 1, 2, 3 or 4, in another embodiment by 1, 2 or 3, in another embodiment by 1 or 2 identical or different substituents R0. In another embodiment, Ar is phenyl which is unsubstituted or substituted by 1 substituent R0. In another embodiment Ar is unsubstituted phenyl. In another embodiment, Ar is phenyl which is substituted by 1, 2, 3 or 4, in another embodiment by 1, 2 or 3, in another embodiment by 1 or 2 identical or different substituents R0. In another embodiment, Ar is phenyl which is substituted by 1 substituent R0. If one substituent R0 is present in Ar, in one embodiment it is located in position 2, in another embodiment in position 3, in another embodiment in position 4 of the phenyl group. If two substituents R0 are present which do not form a ring together with the carbon atoms carrying them, in one embodiment they are located in positions 2 and 3, in another embodiment in positions 2 and 4, in another embodiment in positions 2 and 5, in another embodiment in positions 2 and 6, in another embodiment in positions 3 and 4, and in another embodiment in positions 3 and 5 of the phenyl group.

The double bond which is present in the mono-unsaturated ring which can be formed by two substituents R0 bonded to adjacent ring carbon atoms in Ar together with the carbon atoms carrying them, is present between the said two adjacent ring carbon in the aromatic ring Ar which are common to the ring Ar and the ring formed by the two groups R0, and because of the rules of nomenclature for fused rings is regarded as a double bond present in both rings. The case that two groups R0 bonded to adjacent carbon atoms in Ar together with the carbon atoms carrying them form a 5-membered to 7-membered mono-unsaturated ring, which is a monocyclic ring, can in other words be regarded as two groups R0 together forming a divalent residue comprising a chain of 3 to 5 atoms of which 0, 1 or 2 are identical or different heteroatoms selected from the series consisting of nitrogen, oxygen and sulfur, the terminal atoms of which, which are bonded to the two adjacent ring carbon atoms in Ar, are separated from each other by 1 to 3 atoms. Examples of such divalent residues, from any one or more of which two groups R0 bonded to adjacent ring carbon atoms in Ar are selected in one embodiment of the invention, are the residues —CH$_2$—CH$_2$—CH$_2$—, —CH$_2$—CH$_2$—CH$_2$—CH$_2$—, —CH$_2$—CH$_2$—CH$_2$—

CH$_2$—CH$_2$—, —O—CH$_2$—CH$_2$—, —CH$_2$—CH$_2$—O—, —O—CH$_2$—O—, —O—CH$_2$—CH$_2$—O—, —O—CH$_2$—CH$_2$—CH$_2$—O—, —NH—CH$_2$—CH$_2$—O—, —O—CH$_2$—CH$_2$—NH—, —S—CH$_2$—CH$_2$—NH— and —NH—CH$_2$—CH$_2$—S—, which can all be substituted on carbon atoms and nitrogen atoms by substituents selected from the series consisting of fluorine and (C$_1$-C$_4$)-alkyl, for example fluorine and methyl, and can thus also be present, for example, as the divalent residues —O—CF$_2$—O—, —O—C(CH$_3$)$_2$—O—, —N(CH$_3$)—CH$_2$—CH$_2$—O—, —O—CH$_2$—CH$_2$—N(CH$_3$)—, —S—CH$_2$—CH$_2$—N(CH$_3$)— and —N(CH$_3$)—CH$_2$—CH$_2$—S—. In one embodiment of the invention, the ring which can be formed by two groups R0 bonded to adjacent ring carbon atoms in Ar together with the carbon atoms carrying them, is a 5-membered or 6-membered, in another embodiment a 5-membered, in another embodiment a 6-membered ring. In one embodiment of the invention, the number of substituents selected from the series consisting of fluorine and (C$_1$-C$_4$)-alkyl, which can be present in a ring formed by two groups R0 bonded to adjacent ring carbon atoms in Ar together with the carbon atoms carrying them, is 1, 2 or 3, in another embodiment 1 or 2, in another embodiment 1. In one embodiment of the invention, substituents which can be present in a ring formed by two groups R0 bonded to adjacent ring carbon atoms in Ar together with the carbon atoms carrying them, are fluorine substituents, and in another embodiment they are (C$_1$-C$_4$)-alkyl substituents, for example methyl substituents, and in another embodiment are substituents in such a ring bonded to a ring nitrogen atom selected from the series consisting of (C$_1$-C$_4$)-alkyl.

In one embodiment of the invention, the group R0 is selected from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl-, HO— and (C$_1$-C$_6$)-alkyl-O—, in another embodiment from the series consisting of halogen, (C$_1$-C$_6$)-alkyl, (C$_3$-C$_7$)-cycloalkyl, HO— and (C$_1$-C$_6$)-alkyl-O—, in another embodiment from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl- and (C$_1$-C$_6$)-alkyl-O—, in another embodiment from the series consisting of halogen, (C$_1$-C$_6$)-alkyl, (C$_3$-C$_7$)-cycloalkyl, (C$_1$-C$_6$)-alkyl-O— and (C$_3$-C$_7$)-cycloalkyl-O—, in another embodiment from the series consisting of halogen, (C$_1$-C$_6$)-alkyl, (C$_3$-C$_7$)-cycloalkyl and (C$_1$-C$_6$)-alkyl-O—, in another embodiment from the series consisting of halogen, (C$_1$-C$_6$)-alkyl, HO— and (C$_1$-C$_6$)-alkyl-O—, in another embodiment from the series consisting of halogen, (C$_1$-C$_6$)-alkyl and (C$_1$-C$_6$)-alkyl-O—, in another embodiment from the series consisting of halogen and (C$_1$-C$_6$)-alkyl, in another embodiment from the series consisting of halogen, in another embodiment from the series consisting of (C$_1$-C$_6$)-alkyl, and in another embodiment from the series consisting of (C$_1$-C$_6$)-alkyl-O—, and in all these embodiments two groups R1 bonded to adjacent carbon atoms in Ar, together with the carbon atoms carrying them, can form a 5-membered to 7-membered mono-unsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of fluorine and (C$_1$-C$_4$)-alkyl.

In one embodiment, R0 is selected from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl-, HO—, (C$_1$-C$_6$)-alkyl-O—, (C$_3$-C$_7$)-cycloalkyl-O— and (C$_3$-C$_7$)-cycloalkyl-(C$_1$-C$_4$)-alkyl-O—, in another embodiment from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl-, HO— and (C$_1$-C$_6$)-alkyl-O—, in another embodiment from the series consisting of halogen, (C$_1$-C$_6$)-alkyl, (C$_3$-C$_7$)-cycloalkyl, HO— and (C$_1$-C$_6$)-alkyl-O—, in another embodiment from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl- and (C$_1$-C$_6$)-alkyl-O—, in another embodiment from the series consisting of halogen, (C$_1$-C$_6$)-alkyl, (C$_3$-C$_7$)-cycloalkyl, (C$_1$-C$_6$)-alkyl-O— and (C$_3$-C$_7$)-cycloalkyl-O—, in another embodiment from the series consisting of halogen, (C$_1$-C$_6$)-alkyl, (C$_3$-C$_7$)-cycloalkyl and (C$_1$-C$_6$)-alkyl-O—, in another embodiment from the series consisting of halogen, (C$_1$-C$_6$)-alkyl, HO— and (C$_1$-C$_6$)-alkyl-O—, in another embodiment from the series consisting of halogen, (C$_1$-C$_6$)-alkyl and (C$_1$-C$_6$)-alkyl-O—, in another embodiment from the series consisting of halogen and (C$_1$-C$_6$)-alkyl, in another embodiment from the series consisting of halogen, in another embodiment from the series consisting of (C$_1$-C$_6$)-alkyl, and in another embodiment from the series consisting of (C$_1$-C$_6$)-alkyl-O—.

In one embodiment, a (C$_1$-C$_6$)-alkyl group which represents R0 or is present in the group (C$_1$-C$_6$)-alkyl-O— representing R0, is a (C$_1$-C$_4$)-alkyl group, in another embodiment a (C$_1$-C$_3$)-alkyl group, in another embodiment a (C$_1$-C$_2$)-alkyl group, in another embodiment a methyl group. In one embodiment of the invention, a (C$_3$-C$_7$)-cycloalkyl group which represents R0 or is present in R0, is a (C$_3$-C$_6$)-cycloalkyl group, in another embodiment a (C$_3$-C$_4$)-cycloalkyl group, in another embodiment a cyclopropyl group. In one embodiment, halogen representing R0 is selected from the series consisting of fluorine and chlorine, in another embodiment it is fluorine.

Examples of groups Ar including the optional substituents R0, from any one or more of which Ar is selected in one embodiment of the invention, are phenyl, i.e. unsubstituted phenyl, 2-fluoro-phenyl, 3-fluoro-phenyl, 4-fluoro-phenyl, 2-chloro-phenyl, 3-chloro-phenyl, 4-chloro-phenyl, 2-methyl-phenyl (o-tolyl), 3-methyl-phenyl (m-tolyl), 4-methyl-phenyl (p-tolyl), 2-ethyl-phenyl, 3-ethyl-phenyl, 4-ethyl-phenyl, 2-methoxy-phenyl, 3-methoxy-phenyl, 4-methoxy-phenyl, 2-ethoxy-phenyl, 3-ethoxy-phenyl, 4-ethoxy-phenyl, 2-propoxy-phenyl, 3-propoxy-phenyl, 4-propoxy-phenyl, 2-isopropoxy-phenyl, 3-isopropoxy-phenyl, 4-isopropoxy-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 2-chloro-3-fluoro-phenyl, 2-chloro-4-fluoro-phenyl, 2-chloro-5-fluoro-phenyl, 2-chloro-6-fluoro-phenyl, 3-chloro-2-fluoro-phenyl, 3-chloro-4-fluoro-phenyl, 3-chloro-5-fluoro-phenyl, 4-chloro-2-fluoro-phenyl, 4-chloro-3-fluoro-phenyl, 5-chloro-2-fluoro-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 2-fluoro-3-methyl-phenyl, 2-fluoro-4-methyl-phenyl, 2-fluoro-5-methyl-phenyl, 2-fluoro-6-methyl-phenyl, 3-fluoro-2-methyl-phenyl, 3-fluoro-4-methyl-phenyl, 3-fluoro-5-methyl-phenyl, 4-fluoro-2-methyl-phenyl, 4-fluoro-3-methyl-phenyl, 5-fluoro-2-methyl-phenyl, 2-chloro-3-methyl-phenyl, 2-chloro-4-methyl-phenyl, 2-chloro-5-methyl-phenyl, 2-chloro-6-methyl-phenyl, 3-chloro-2-methyl-phenyl, 3-chloro-4-methyl-phenyl, 3-chloro-5-methyl-phenyl, 4-chloro-2-methyl-phenyl, 4-chloro-3-methyl-phenyl, 5-chloro-2-methyl-phenyl, 2-fluoro-3-methoxy-phenyl, 2-fluoro-4-methoxy-phenyl, 2-fluoro-5-methoxy-phenyl, 2-fluoro-6-methoxy-phenyl, 3-fluoro-2-methoxy-phenyl, 3-fluoro-4-methoxy-phenyl, 3-fluoro-5- methoxy-phenyl, 4-fluoro-2-methoxy-phenyl, 4-fluoro-3-methoxy-phenyl, 5-fluoro-2-methoxy-phenyl, 2-methoxy-3-methyl-phenyl, 2-methoxy-4-methyl-phenyl, 2-methoxy-5-methyl-phenyl, 2-methoxy-6-methyl-phenyl, 3-methoxy-2-methyl-phenyl, 3-methoxy-4-methyl-phenyl, 3-methoxy-5-methyl-phenyl, 4-methoxy-2-methyl-phenyl, 4-methoxy-3-methyl-phenyl, 5-methoxy-2-methyl-phenyl.

In one embodiment of the invention, the group R1 is hydrogen or one or more fluorine substituents. I.e., in this embodiment the cycloalkane ring depicted in formula I is unsubstituted or substituted by one or more fluorine substituents, apart from the groups R2 and R3 and the oxygen atom linking the cycloalkane ring to the chroman ring. In another embodiment, the group R1 is hydrogen or one or more $(C_1-C_4)$-alkyl substituents. I.e., in this embodiment the cycloalkane ring depicted in formula I is unsubstituted or substituted by one or more $(C_1-C_4)$-alkyl substituents, apart from the groups R2 and R3 and the oxygen atom linking the cycloalkane ring to the chroman ring. In another embodiment, the group R1 is hydrogen. I.e., in this embodiment the cycloalkane ring depicted in formula I is unsubstituted, or in other words carries hydrogen atoms only, apart from the groups R2 and R3 and the oxygen atom linking the cycloalkane ring to the chroman ring. In one embodiment, the number of fluorine atoms and/or $(C_1-C_4)$-alkyl groups representing R1 is 1, 2, 3 or 4, in another embodiment 1, 2 or 3, in another embodiment 1 or 2, in another embodiment 1. In one embodiment, $(C_1-C_4)$-alkyl representing R1 is $(C_1-C_3)$-alkyl, in another embodiment $(C_1-C_2)$-alkyl, in another embodiment methyl. In one embodiment, the ring carbon atom of the cycloalkane ring depicted in formula I which carries the oxygen atom linking the ring to the chroman ring, does not carry a group R1 which is fluorine or $(C_1-C_4)$-alkyl, i.e. this embodiment the said ring carbon atom carries a hydrogen atom.

In one embodiment of the invention, the group R2 is selected from the series consisting of $(C_1-C_6)$-alkyl, HO—, $(C_1-C_6)$-alkyl-O—, $(C_1-C_6)$-alkyl-C(O)—O—, phenyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, $(C_1-C_6)$-alkyl-O—, $(C_1-C_6)$-alkyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, $(C_1-C_6)$-alkyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, $(C_1-C_6)$-alkyl-C(O)—O—, Het1-C(O)—O—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, $(C_1-C_6)$-alkyl-O—, $(C_1-C_6)$-alkyl-C(O)—O—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, $(C_1-C_6)$-alkyl-O—, $(C_1-C_6)$-alkyl-C(O)—O—, Het1-C(O)—O—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, $(C_1-C_6)$-alkyl-O—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, $(C_1-C_6)$-alkyl-C(O)—O—, Het1-C(O)—O—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, $(C_1-C_6)$-alkyl-O—, R5-N(R6)-, R7-C(O)—N(R8)-, R9-N(R10)-C(O)—N(R8)- and R5-N(R6)-C(O)—, in another embodiment from the series consisting of $(C_1-C_6)$-alkyl, HO—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, R5-N(R6)-, R7-C(O)—N(R8)-, R9-N(R10)-C(O)—N(R8)- and R5-N(R6)-C(O)—, in another embodiment from the series consisting of $(C_1-C_6)$-alkyl, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, R5-N(R6)-, R7-C(O)—N(R8)-, R9-N(R10)-C(O)—N(R8)- and R5-N(R6)-C(O)—, in another embodiment from the series consisting of $(C_1-C_6)$-alkyl, R5-N(R6)-, R7-C(O)—N(R8)- and R5-N(R6)-C(O)—, in another embodiment from the series consisting of $(C_1-C_6)$-alkyl, HO—, $(C_1-C_6)$-alkyl-O—, $(C_1-C_6)$-alkyl-C(O)—O—, phenyl-C(O)—O— and Het1-C(O)—O—, in another embodiment from the series consisting of $(C_1-C_6)$-alkyl, HO—, $(C_1-C_6)$-alkyl-C(O)—O and Het1-C(O)—O—, in another embodiment from the series consisting of HO—, $(C_1-C_6)$-alkyl-O—, $(C_1-C_6)$-alkyl-C(O)—O— and Het1-C(O)—O—, in another embodiment from the series consisting of HO—, $(C_1-C_6)$-alkyl-C(O)—O— and Het1-C(O)—O—, wherein in all these embodiments $(C_1-C_6)$-alkyl is unsubstituted or substituted by one or more identical or different substituents R20, or in all these embodiments R2 and R3 together are oxo.

In one embodiment, R2 is selected from the series consisting of $(C_1-C_6)$-alkyl, HO—, $(C_1-C_6)$-alkyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, R5-N(R6)-, R7-C(O)—N(R8)-, R7-S(O)$_2$—N(R8)-, R9-N(R10)-C(O)—N(R8)- and R5-N(R6)-C(O)—, in another embodiment from the series consisting of $(C_1-C_6)$-alkyl, HO—, $(C_1-C_6)$-alkyl-C(O)—O—, Het1-C(O)—O—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, HO—, R5-N(R6)-, R7-C(O)—N(R8)-, in another embodiment from the series consisting of $(C_1-C_6)$-alkyl, HO—, R5-N(R6)-, R7-C(O)—N(R8)-, R9-N(R10)-C(O)—N(R8)- and R5-N(R6)-C(O)—, in another embodiment from the series consisting of $(C_1-C_6)$-alkyl, R5-N(R6)-, R7-C(O)—N(R8)-, R7-S(O)$_2$—N(R8)- and R5-N(R6)-C(O)—, in another embodiment from the series consisting of $(C_1-C_6)$-alkyl, R5-N(R6)-, R7-C(O)—N(R8)- and R5-N(R6)-C(O)—, in another embodiment from the series consisting of $(C_1-C_6)$-alkyl, R5-N(R6)- and R5-N(R6)-C(O)—, in another embodiment from the series consisting of R5-N(R6)-, R7-C(O)—N(R8)- and R7-S(O)$_2$—N(R8)-, in another embodiment from the series consisting of R5-N(R6)-, R7-C(O)—N(R8)- and R5-N(R6)-C(O)—, in another embodiment from the series consisting of $(C_1-C_6)$-alkyl and R5-N(R6)-, in another embodiment from the series consisting of $(C_1-C_6)$-alkyl and R5-N(R6)-C(O)—, in another embodiment from the series consisting of R5-N(R6)- and R5-N(R6)-C(O)—, wherein in all these embodiments $(C_1-C_6)$-alkyl is unsubstituted or substituted by one or more identical or different substituents R20.

In one embodiment, R2 is $(C_1-C_6)$-alkyl which is unsubstituted or substituted by one or more identical or different substituents R20. In another embodiment, R(2) is R5-N(R6)- and the compounds of the formula I thus are compounds of the formula Ia.

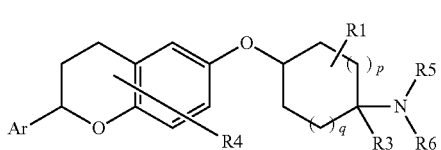

In another embodiment, R(2) is R7-C(O)—N(R8)- and the compounds of the formula I thus are compounds of the formula Ib.

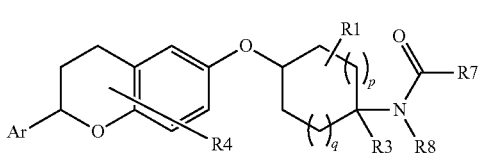

In another embodiment, R(2) is R7-S(O)$_2$—N(R8)- and the compounds of the formula I thus are compounds of the formula Ic.

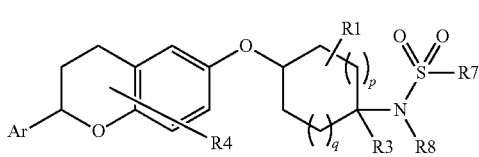

In another embodiment, R(2) is R5-N(R6)-C(O)— and the compounds of the formula I thus are compounds of the formula Id.

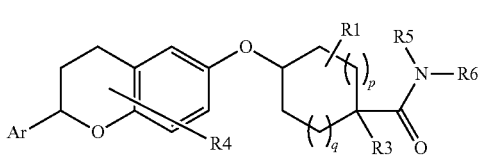

The groups Ar, R1, R3 to R8 and the numbers p and q in the compounds of the formulae Ia, Ib, Ic and Id are defined as in the compounds of the formula I.

In one embodiment, the number of substituents R20 in a substituted ($C_1$-$C_6$)-alkyl group which represents R2 or is present in the groups ($C_1$-$C_6$)-alkyl-O— or ($C_1$-$C_6$)-alkyl-C(O)—O— representing R2, is 1, 2, 3 or 4, in another embodiment 1, 2 or 3, in another embodiment 1 or 2, in another embodiment 1. In one embodiment, a ($C_1$-$C_6$)-alkyl group which represents R2, is substituted by one or more identical or different substituents R20, i.e. it is not unsubstituted. In one embodiment, a ($C_1$-$C_6$)-alkyl group which represents R2 is substituted by one or more identical or different substituents R20, one of which is bonded to the carbon atom of the alkyl group which is bonded to the cycloalkane ring depicted in formula I, i.e. in position 1 of the alkyl group. In one embodiment, a ($C_1$-$C_6$)-alkyl group which represents R2 or is present in the groups ($C_1$-$C_6$)-alkyl-O— or ($C_1$-$C_6$)-alkyl-C(O)—O— representing R2, is a ($C_1$-$C_4$)-alkyl group, in another embodiment a ($C_1$-$C_3$)-alkyl group, in another embodiment a ($C_1$-$C_2$)-alkyl group, in another embodiment a methyl group, which are all unsubstituted or substituted by one or more identical or different substituents R20, and in one embodiment are substituted by one or more identical or different substituents R20, wherein in one embodiment the number of substituents R20 is 1, 2 or 3, in another embodiment 1 or 2, and in another embodiment 1. In one embodiment, a ($C_1$-$C_6$)-alkyl group which represents R2 is a methyl group which is substituted by one substituent R20, and in this embodiment the group R2 thus is the group R20-CH$_2$—.

In one embodiment of the invention, the group R3 is hydrogen, in another embodiment it is ($C_1$-$C_6$)-alkyl, which is unsubstituted or substituted by one or two identical or different substituents selected from the series consisting of ($C_3$-$C_7$)-cycloalkyl, phenyl, HO— and ($C_1$-$C_4$)-alkyl-O—, wherein alkyl groups representing R3, like alkyl groups in general, can independently of these specified substituents be substituted by one or more fluorine substituents. In one embodiment, the number of substituents selected from the series consisting of ($C_3$-$C_7$)-cycloalkyl, phenyl, HO— and ($C_1$-$C_4$)-alkyl-O— in a substituted alkyl group representing R3 is one. In one embodiment, an alkyl group representing R3 is not substituted by substituents selected from the series consisting of ($C_3$-$C_7$)-cycloalkyl, phenyl, HO— and ($C_1$-$C_4$)-alkyl-O—. In one embodiment, the substituents in an alkyl group representing R3 are selected from the series consisting of ($C_3$-$C_7$)-cycloalkyl, phenyl and ($C_1$-$C_4$)-alkyl-O—, in another embodiment from the series consisting of ($C_3$-$C_7$)-cycloalkyl and phenyl, and in another embodiment they are phenyl groups. In one embodiment, a ($C_1$-$C_6$)-alkyl group representing R3 is a ($C_1$-$C_4$)-alkyl group, in another embodiment a ($C_1$-$C_3$)-alkyl group, in another embodiment a ($C_1$-$C_2$)-alkyl group, in another embodiment a methyl group. In one embodiment, R2 and R3 have their individual meanings, but together are not oxo. In another embodiment, R2 and R3 together are oxo.

As indicated above, in the free binding sites of the chroman ring, i.e. binding sites in positions 2, 3, 4, 5, 7 and 8 of the chroman ring which are not occupied by bonds within the ring or the bond to the group Ar, hydrogen atoms or substituents selected from the series consisting of halogen, ($C_1$-$C_4$)-alkyl and ($C_1$-$C_4$)-alkyl-O— can be present which represent groups R4. In one embodiment of the invention, in the free binding site in position 2 of the chroman ring, i.e. the free binding site of the ring carbon atom which carries the group Ar, a hydrogen atom is present, and in the free binding sites in positions 3, 4, 5, 7 and 8 of the chroman ring hydrogen atoms or substituents selected from the series consisting of halogen, ($C_1$-$C_4$)-alkyl and ($C_1$-$C_4$)-alkyl-O— are present. In another embodiment of the invention, in the free binding sites in positions 2, 3 and 4 of the chroman ring hydrogen atoms are present, and in the free binding sites in positions 5, 7 and 8 of the chroman ring hydrogen atoms or substituents selected from the series consisting of halogen, ($C_1$-$C_4$)-alkyl and ($C_1$-$C_4$)-alkyl-O— are present. In another embodiment of the invention, in the free binding sites in positions 2 and 5 of the chroman ring hydrogen atoms are present, and in the free binding sites in positions 3, 4, 7 and 8 of the chroman ring hydrogen atoms or substituents selected from the series consisting of halogen, ($C_1$-$C_4$)-alkyl and ($C_1$-$C_4$)-alkyl-O— are present. In another embodiment of the invention, in the free binding sites in positions 2, 5, 7 and 8 of the chroman ring hydrogen atoms are present, and in the free binding sites in positions 3 and 4 of the chroman ring hydrogen atoms or substituents selected from the series consisting of halogen, $(C_1-C_4)$-alkyl and $(C_1-C_4)$-alkyl-O— are present. In one embodiment, the number of groups R4 which are different from hydrogen, i.e. the number of substituents R4 which are selected from halogen, $(C_1-C_4)$-alkyl and $(C_1-C_4)$-alkyl-O—, is 1, 2 or 3, in another embodiment it is 1 or 2, in another embodiment it is 1, and in another embodiment it is 0, and in the latter embodiment thus no groups R4 which are different from hydrogen are present in the chroman ring, and hydrogen atoms are present in all its free binding sites. In one embodiment, R4 is hydrogen or one or more identical or different substituents selected from the series consisting of halogen and $(C_1-C_4)$-alkyl, in another embodiment R4 is hydrogen or one or more identical or different substituents selected from the series consisting of fluorine, chlorine and $(C_1-C_4)$-alkyl. In one embodiment, R4 in the free binding sites in positions 2, 3 and 4 of the chroman ring is hydrogen or one or more identical or different substituents selected from the series consisting of fluorine and $(C_1-C_4)$-alkyl, in another embodiment R4 in the free binding sites in positions 2, 3 and 4 of the chroman ring is hydrogen or one or more identical or different substituents selected from the series consisting of $(C_1-C_4)$-alkyl, and R4 in the free binding sites in positions 5, 7 and 8 of the chroman ring is hydrogen or one or more identical or different substituents selected from the series consisting of halogen, $(C_1-C_4)$-alkyl and $(C_1-C_4)$-alkyl-O—, in another embodiment R4 in the free binding sites in positions 5, 7 and 8 of the chroman ring is hydrogen or one or more identical or different substituents selected from the series consisting of halogen and $(C_1-C_4)$-alkyl, in another embodiment R4 in the free binding sites in positions 5, 7 and 8 of the chroman ring is hydrogen or one or more identical or different substituents selected from the series consisting of halogen. In one embodiment of the invention, a $(C_1-C_4)$-alkyl group representing R4 or present in R4 is $(C_1-C_2)$-alkyl, in another embodiment it is methyl.

In one embodiment of the invention, R5 and R6 are independently of one another selected from the series consisting of hydrogen, $(C_1-C_6)$-alkyl, $(C_2-C_6)$-alkenyl, $(C_3-C_7)$-cycloalkyl, $(C_6-C_{10})$-bicycloalkyl, Het1 and Het2, in another embodiment from the series consisting of hydrogen, $(C_1-C_6)$-alkyl, $(C_2-C_6)$-alkenyl, $(C_3-C_7)$-cycloalkyl, Het1 and Het2, in another embodiment from the series consisting of hydrogen, $(C_1-C_6)$-alkyl, $(C_3-C_7)$-cycloalkyl, Het1 and Het2, in another embodiment from the series consisting of hydrogen, $(C_1-C_6)$-alkyl, $(C_3-C_7)$-cycloalkyl and $(C_6-C_{10})$-bicycloalkyl, in another embodiment from the series consisting of hydrogen, $(C_1-C_6)$-alkyl, $(C_3-C_7)$-cycloalkyl and Het2, in another embodiment from the series consisting of hydrogen, $(C_1-C_6)$-alkyl and $(C_3-C_7)$-cycloalkyl, in another embodiment from the series consisting of hydrogen and $(C_1-C_6)$-alkyl, wherein in all these embodiments $(C_1-C_6)$-alkyl is unsubstituted or substituted by one or more identical or different substituents R20, and $(C_3-C_7)$-cycloalkyl, $(C_6-C_{10})$-bicycloalkyl and Het2 all are unsubstituted or substituted by one or more identical or different substituents R21, and Het1 is unsubstituted or substituted by one or more identical or different substituents R22.

In one embodiment of the invention, one of the groups R5 and R6 is selected from the series consisting of hydrogen and $(C_1-C_6)$-alkyl, in another embodiment from the series consisting of hydrogen and $(C_1-C_4)$-alkyl, in another embodiment from the series consisting of hydrogen and $(C_1-C_2)$-alkyl, in another embodiment from the series consisting of hydrogen and methyl, and in another embodiment is hydrogen, and the other of the groups R5 and R6 is selected from the series consisting of hydrogen, $(C_1-C_6)$-alkyl, $(C_2-C_6)$-alkenyl, $(C_3-C_7)$-cycloalkyl, $(C_6-C_{10})$-bicycloalkyl, phenyl, Het1 and Het2, in another embodiment from the series consisting of hydrogen, $(C_1-C_6)$-alkyl, $(C_2-C_6)$-alkenyl, $(C_3-C_7)$-cycloalkyl, $(C_6-C_{10})$-bicycloalkyl, Het1 and Het2, in another embodiment from the series consisting of hydrogen, $(C_1-C_6)$-alkyl, $(C_2-C_6)$-alkenyl, $(C_3-C_7)$-cycloalkyl, Het1 and Het2, in another embodiment from the series consisting of hydrogen, $(C_1-C_6)$-alkyl, $(C_3-C_7)$-cycloalkyl, Het1 and Het2, in another embodiment from the series consisting of hydrogen, $(C_1-C_6)$-alkyl, $(C_3-C_7)$-cycloalkyl and $(C_6-C_{10})$-bicycloalkyl, in another embodiment from the series consisting of hydrogen, $(C_1-C_6)$-alkyl, $(C_3-C_7)$-cycloalkyl and Het2, in another embodiment from the series consisting of hydrogen, $(C_1-C_6)$-alkyl and $(C_3-C_7)$-cycloalkyl, in another embodiment from the series consisting of hydrogen and $(C_1-C_6)$-alkyl, wherein in all these embodiments $(C_1-C_6)$-alkyl, $(C_1-C_4)$-alkyl, $(C_1-C_2)$-alkyl and methyl representing R5 or R6 is unsubstituted or substituted by one or more identical or different substituents R20, and $(C_3-C_7)$-cycloalkyl, $(C_6-C_{10})$-bicycloalkyl and Het2 all are unsubstituted or substituted by one or more identical or different substituents R21, and Het1 is unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21.

In one embodiment of the invention, one of the groups R5 and R6 is selected from the series consisting of hydrogen and ($C_1$-$C_6$)-alkyl, in another embodiment from the series consisting of hydrogen and ($C_1$-$C_4$)-alkyl, in another embodiment from the series consisting of hydrogen and ($C_1$-$C_2$)-alkyl, in another embodiment from the series consisting of hydrogen and methyl, and in another embodiment is hydrogen, and the other of the groups R5 and R6 is selected from the series consisting of hydrogen, ($C_1$-$C_6$)-alkyl, ($C_2$-$C_6$)-alkenyl, ($C_3$-$C_7$)-cycloalkyl, ($C_6$-$C_{10}$)-bicycloalkyl, phenyl, Het1 and Het2, in another embodiment from the series consisting of hydrogen, ($C_1$-$C_6$)-alkyl, ($C_2$-$C_6$)-alkenyl, ($C_3$-$C_7$)-cycloalkyl, ($C_6$-$C_{10}$)-bicycloalkyl, Het1 and Het2, in another embodiment from the series consisting of hydrogen, ($C_1$-$C_6$)-alkyl, ($C_2$-$C_6$)-alkenyl, ($C_3$-$C_7$)-cycloalkyl, Het1 and Het2, in another embodiment from the series consisting of hydrogen, ($C_1$-$C_6$)-alkyl, ($C_3$-$C_7$)-cycloalkyl, Het1 and Het2, in another embodiment from the series consisting of hydrogen, ($C_1$-$C_6$)-alkyl, ($C_3$-$C_7$)-cycloalkyl and ($C_6$-$C_{10}$)-bicycloalkyl, in another embodiment from the series consisting of hydrogen, ($C_1$-$C_6$)-alkyl, ($C_3$-$C_7$)-cycloalkyl and Het2, in another embodiment from the series consisting of hydrogen, ($C_1$-$C_6$)-alkyl and ($C_3$-$C_7$)-cycloalkyl, in another embodiment from the series consisting of hydrogen and ($C_1$-$C_6$)-alkyl, wherein in all these embodiments ($C_1$-$C_6$)-alkyl, ($C_1$-$C_4$)-alkyl, ($C_1$-$C_2$)-alkyl and methyl representing R5 or R6 is unsubstituted or substituted by one or more identical or different substituents R20, and ($C_3$-$C_7$)-cycloalkyl, ($C_6$-$C_{10}$)-bicycloalkyl and Het2 all are unsubstituted or substituted by one or more identical or different substituents R21, and Het1 is unsubstituted or substituted by one or more identical or different substituents R22. In one embodiment, R5 and R6 both are hydrogen.

In one embodiment of the invention, one of the groups R5 and R6 is selected from the series consisting of hydrogen and ($C_1$-$C_6$)-alkyl, in another embodiment from the series consisting of hydrogen and ($C_1$-$C_4$)-alkyl, in another embodiment from the series consisting of hydrogen and ($C_1$-$C_2$)-alkyl, in another embodiment from the series consisting of hydrogen and methyl, and in another embodiment is hydrogen, and the other of the groups R5 and R6 is selected from the series consisting of ($C_1$-$C_6$)-alkyl, ($C_2$-$C_6$)-alkenyl, ($C_3$-$C_7$)-cycloalkyl, ($C_6$-$C_{10}$)-bicycloalkyl, phenyl, Het1 and Het2, in another embodiment from the series consisting of ($C_1$-$C_6$)-alkyl, ($C_2$-$C_6$)-alkenyl, ($C_3$-$C_7$)-cycloalkyl, ($C_6$-$C_{10}$)-bicycloalkyl, Het1 and Het2, in another embodiment from the series consisting of ($C_1$-$C_6$)-alkyl, ($C_2$-$C_6$)-alkenyl, ($C_3$-$C_7$)-cycloalkyl, Het1 and Het2, in another embodiment from the series consisting of ($C_1$-$C_6$)-alkyl, ($C_3$-$C_7$)-cycloalkyl, Het1 and Het2, in another embodiment from the series consisting of ($C_1$-$C_6$)-alkyl, ($C_3$-$C_7$)-cycloalkyl and ($C_6$-$C_{10}$)-bicycloalkyl, in another embodiment from the series consisting of ($C_1$-$C_6$)-alkyl, ($C_3$-$C_7$)-cycloalkyl and Het2, in another embodiment from the series consisting of ($C_1$-$C_6$)-alkyl and ($C_3$-$C_7$)-cycloalkyl, in another embodiment from the series consisting of ($C_1$-$C_6$)-alkyl, wherein in all these embodiments ($C_1$-$C_6$)-alkyl, ($C_1$-$C_4$)-alkyl, ($C_1$-$C_2$)-alkyl and methyl representing R5 or R6 is unsubstituted or substituted by one or more identical or different substituents R20, and ($C_3$-$C_7$)-cycloalkyl, ($C_6$-$C_{10}$)-bicycloalkyl and Het2 all are unsubstituted or substituted by one or more identical or different substituents R21, and Het1 is unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21.

In one embodiment of the invention, one of the groups R5 and R6 is selected from the series consisting of hydrogen and ($C_1$-$C_6$)-alkyl, in another embodiment from the series consisting of hydrogen and ($C_1$-$C_4$)-alkyl, in another embodiment from the series consisting of hydrogen and ($C_1$-$C_2$)-alkyl, in another embodiment from the series consisting of hydrogen and methyl, and in another embodiment is hydrogen, and the other of the groups R5 and R6 is selected from the series consisting of ($C_1$-$C_6$)-alkyl, ($C_2$-$C_6$)-alkenyl, ($C_3$-$C_7$)-cycloalkyl, ($C_6$-$C_{10}$)-bicycloalkyl, phenyl, Het1 and Het2, in another embodiment from the series consisting of ($C_1$-$C_6$)-alkyl, ($C_2$-$C_6$)-alkenyl, ($C_3$-$C_7$)-cycloalkyl, ($C_6$-$C_{10}$)-bicycloalkyl, Het1 and Het2, in another embodiment from the series consisting of ($C_1$-$C_6$)-alkyl, ($C_2$-$C_6$)-alkenyl, ($C_3$-$C_7$)-cycloalkyl, Het1 and Het2, in another embodiment from the series consisting of ($C_1$-$C_6$)-alkyl, ($C_3$-$C_7$)-cycloalkyl, Het1 and Het2, in another embodiment from the series consisting of ($C_1$-$C_6$)-alkyl, ($C_3$-$C_7$)-cycloalkyl and ($C_6$-$C_{10}$)-bicycloalkyl, in another embodiment from the series consisting of ($C_1$-$C_6$)-alkyl, ($C_3$-$C_7$)-cycloalkyl and Het2, in another embodiment from the series consisting of ($C_1$-$C_6$)-alkyl and ($C_3$-$C_7$)-cycloalkyl, in another embodiment from the series consisting of ($C_1$-$C_6$)-alkyl, wherein in all these embodiments ($C_1$-$C_6$)-alkyl, ($C_1$-$C_4$)-alkyl, ($C_1$-$C_2$)-alkyl and methyl representing R5 or R6 is unsubstituted or substituted by one or more identical or different substituents R20, and ($C_3$-$C_7$)-cycloalkyl, ($C_6$-$C_{10}$)-bicycloalkyl and Het2 all are unsubstituted or substituted by one or more identical or different substituents R21, and Het1 is unsubstituted or substituted by one or more identical or different substituents R22.

In one embodiment of the invention, a ($C_1$-$C_6$)-alkyl group representing R5 or R6 is a ($C_1$-$C_4$)-alkyl group, in another embodiment a ($C_1$-$C_3$)-alkyl group, in another embodiment a ($C_1$-$C_2$)-alkyl group, in another embodiment any one or more groups selected from the series consisting of butyl, propyl, isopropyl, ethyl and methyl, for example selected from the series consisting of methyl, ethyl and propyl, which are all unsubstituted or substituted by one or more, for example 1, 2 or 3, or 1 or 2, or 1, identical or different substituents R20, which substituents can be present in any positions, for example in position 1 and/or in position 2 of an ethyl group representing R5 or R6, or in position 1 and/or in position 2 and/or in position 3 of a propyl group representing R5 or R6.

In one embodiment of the invention, the number of identical or different substituents R20 which are optionally present in a ($C_1$-$C_6$)-alkyl group representing R5 or R6, is 1, 2, 3 or 4, in another embodiment it is 1, 2 or 3, in another embodiment it is 1 or 2, in another embodiment it is 1, in another embodiment it is 0. In one embodiment, the number of groups R24 representing substituents R20, which are optionally present in a ($C_1$-$C_6$)-alkyl group representing R5 or R6 besides any other substituents R20, is 1 or 2, in another embodiment it is 1, in another embodiment it is 0 (zero), i.e., in the latter embodiment R20 is as defined, but is not R24. In one embodiment, the number of oxo groups representing substituents R20, which are optionally present in a ($C_1$-$C_6$)-alkyl group representing R5 or R6 besides any other substituents R20, is 1 or 2, in another embodiment it is 1, in another embodiment it is 0. In one embodiment, the number of groups selected from the series consisting of R31-N(R32)-C(O)—, R34-O—C(O)— and R31-N(R32)-S(O)$_2$— representing substituents R20, which are optionally present in a ($C_1$-$C_6$)-alkyl group representing R5 or R6 besides any other substituents R20, is 1 or 2, in another embodiment it is 1, in another embodiment it is 0.

In one embodiment of the invention, the number of identical or different substituents R21 which are optionally present in ($C_3$-$C_7$)-cycloalkyl, ($C_6$-$C_{10}$)-bicycloalkyl and Het2 groups representing R5 or R6, is independently of each other 1, 2, 3 or 4, in another embodiment it is 1, 2 or 3, in another embodiment it is 1 or 2, in another embodiment it is 1. In one embodiment, the number of groups R24 representing substituents R21, which are optionally present in ($C_3$-$C_7$)-cycloalkyl, ($C_6$-$C_{10}$)-bicycloalkyl and Het2 groups representing R5 or R6 besides any other substituents R21, is 1 or 2, in another embodiment it is 1, in another embodiment it is 0. In one embodiment, the number of oxo groups representing substituents R21, which are optionally present in ($C_3$-$C_7$)-cycloalkyl, ($C_6$-$C_{10}$)-bicycloalkyl and Het2 groups representing R5 or R6 besides any other substituents R21, is 1 or 2, in another embodiment it is 1, in another embodiment it is 0. In one embodiment, the number of groups selected from the series consisting of R34-O—C(O)—($C_1$-$C_4$)-alkyl-, R31-N(R32)-C(O)—, R34-O—C(O)— and R31-N(R32)-S(O)$_2$— representing substituents R21, which are optionally present in ($C_3$-$C_7$)-cycloalkyl, ($C_6$-$C_{10}$)-bicycloalkyl and Het2 groups representing R5 or R6 besides any other substituents R21, is 1 or 2, in another embodiment it is 1, in another embodiment it is 0.

In one embodiment of the invention, the number of identical or different substituents R22 which are optionally present in phenyl and Het1 groups representing R5 or R6, is independently of each other 1, 2, 3 or 4, in another embodiment it is 1, 2 or 3, in another embodiment it is 1 or 2, in another embodiment it is 1, in another embodiment it is 0. In one embodiment, the number of groups selected from the series consisting of R31-N(R32)-C(O)—, R34-O—C(O)— and R31-N(R32)-S(O)$_2$— representing substituents R22, which are optionally present in phenyl and Het1 groups representing R5 or R6 besides any other substituents R22, is 1 or 2, in another embodiment it is 1, in another embodiment it is 0.

The monocyclic heterocycle which can be formed by the groups R5 and R6 together with the nitrogen atom carrying them, which heterocycle is thus bonded via a ring nitrogen atom, can be 4-membered, 5-membered, 6-membered or 7-membered. In one embodiment of the invention, this heterocycle is 4-membered to 6-membered, in another embodiment it is 5-membered to 6-membered, in another embodiment it is 5-membered, in another embodiment it is 6-membered. In one embodiment, a heterocycle formed by the groups R5 and R6 together with the nitrogen atom carrying them, is saturated or contains one double bond within the ring, in another embodiment it is saturated. In one embodiment, the further ring heteroatom which is optionally present in a heterocycle formed by the groups R5 and R6 together with the nitrogen atom carrying them, is selected from the series consisting of nitrogen and oxygen, in another embodiment it is a nitrogen atom, and in another embodiment it is an oxygen atom. Examples of heterocyclic groups, from any one or more of which the heterocyclic groups formed by the groups R5 and R6 together with the nitrogen atom carrying them is selected in one embodiment of the invention, are azetidin-1-yl, pyrrolidin-1-yl, piperidin-1-yl, azepan-1-yl, imidazolidin-1-yl, oxazolidin-3-yl, thiazolidin-3-yl, piperazin-1-yl, morpholin-4-yl and thiomorpholin-4-yl, which can all be unsubstituted or substituted by one or more identical or different substituents R21.

In one embodiment of the invention, the number of identical or different substituents R21 which are optionally present in a heterocycle formed by R5 and R6 together with the nitrogen atom carrying them, is 1, 2, 3 or 4, in another embodiment it is 1, 2 or 3, in another embodiment it is 1 or 2, in another embodiment it is 1, in another embodiment it is 0. In one embodiment, the number of groups R24 representing substituents R21, which are optionally present in a heterocycle formed by R5 and R6 together with the nitrogen atom carrying them besides any other substituents R21, is 1 or 2, in another embodiment it is 1, in another embodiment it is 0. In one embodiment, the number of oxo groups representing substituents R21, which are optionally present in a heterocycle formed by R5 and R6 together with the nitrogen atom carrying them besides any other substituents R21, is 1 or 2, in another embodiment it is 1, in another embodiment it is 0. In one embodiment, the number of groups selected from the series consisting of R34-O—C(O)—($C_1$-$C_4$)-alkyl-, R31-N(R32)-C(O)—, R34-O—C(O)— and R31-N(R32)-S(O)$_2$— representing substituents R21, which are optionally present in a heterocycle formed by R5 and R6 together with the nitrogen atom carrying them besides any other substituents R21, is 1 or 2, in another embodiment it is 1, in another embodiment it is 0.

In one embodiment of the invention, R7 is in any of its occurrences, independently of other occurrences, selected from the series consisting of ($C_1$-$C_6$)-alkyl, ($C_3$-$C_7$)-cycloalkyl, Het1 and Het2, in another embodiment from the series consisting of ($C_1$-$C_6$)-alkyl, ($C_3$-$C_7$)-cycloalkyl and Het2, in another embodiment from the series consisting of ($C_1$-$C_6$)-alkyl, Het1 and Het2, in another embodiment from the series consisting of ($C_3$-$C_7$)-cycloalkyl, Het1 and Het2, in another embodiment from the series consisting of ($C_1$-$C_6$)-alkyl and Het2, in another embodiment from the series consisting of ($C_3$-$C_7$)-cycloalkyl and Het2, in another embodiment from the series consisting of phenyl and Het1, in another embodiment it is ($C_1$-$C_6$)-alkyl, in another embodiment it is ($C_3$-$C_7$)-cycloalkyl, in another embodiment is phenyl, in another embodiment is Het1, and in another embodiment is Het2, wherein all groups ($C_1$-$C_6$)-alkyl are unsubstituted or substituted by one or more identical or different substituents R20, all groups ($C_3$-$C_7$)-cycloalkyl and Het2 are unsubstituted or substituted by one or more identical or different substituents R2, and all groups phenyl and Het1 are unsubstituted or substituted by one or more identical or different substituents R22.

In one embodiment of the invention, the number of identical or different substituents R20 which are optionally present in a ($C_1$-$C_6$)-alkyl group representing R7, is 1, 2, 3 or 4, in another embodiment it is 1, 2 or 3, in another embodiment it is 1 or 2, in another embodiment it is 1, in another embodiment it is 0. In one embodiment, the number of groups R24 representing substituents R20, which are optionally present in a ($C_1$-$C_6$)-alkyl group representing R7 besides any other substituents R20, is 1 or 2, in another embodiment it is 1, in another embodiment it is 0 (zero), i.e., in the latter embodiment R20 is as defined, but is not R24. In one embodiment, the number of oxo groups representing substituents R20, which are optionally present in a ($C_1$-$C_6$)-alkyl group representing R7 besides any other substituents R20, is 1 or 2, in another embodiment it is 1, in another embodiment it is 0. In one embodiment, the number of groups selected from the series consisting of R31-N(R32)-C(O)—, R34-O—C(O)— and R31-N(R32)-S(O)$_2$— representing substituents R20, which are optionally present in a ($C_1$-$C_6$)-alkyl group representing R7 besides any other substituents R20, is 1 or 2, in another embodiment it is 1, in another embodiment it is 0.

In one embodiment of the invention, the number of identical or different substituents R21 which are optionally present in ($C_3$-$C_7$)-cycloalkyl and Het2 groups representing R7, is independently of each other 1, 2, 3 or 4, in another embodiment it is 1, 2 or 3, in another embodiment it is 1 or 2, in another embodiment it is 1, in another embodiment it is 0. In one embodiment, the number of groups R24 representing substituents R21, which are optionally present in ($C_3$-$C_7$)-cycloalkyl and Het2 groups representing R7 besides any other substituents R21, is 1 or 2, in another embodiment it is 1, in another embodiment it is 0. In one embodiment, the number of oxo groups representing substituents R21, which are optionally present in ($C_3$-$C_7$)-cycloalkyl and Het2 groups representing R7 besides any other substituents R21, is 1 or 2, in another embodiment it is 1, in another embodiment it is 0. In one embodiment, the number of groups selected from the series consisting of R34-O—C(O)—($C_1$-$C_4$)-alkyl-, R31-N(R32)-C(O)—, R34-O—C(O)— and R31-N(R32)-S(O)$_2$— representing substituents R21, which are optionally present in ($C_3$-$C_7$)-cycloalkyl and Het2 groups representing R7 besides any other substituents R21, is 1 or 2, in another embodiment it is 1, in another embodiment it is 0.

In one embodiment of the invention, the number of identical or different substituents R22 which are optionally present in phenyl and Het1 groups representing R7, is independently of each other 1, 2, 3 or 4, in another embodiment it is 1, 2 or 3, in another embodiment it is 1 or 2, in another embodiment it is 1, in another embodiment it is 0. In one embodiment, the number of groups selected from the series consisting of R31-N(R32)-C(O)—, R34-O—C(O)— and R31-N(R32)-S(O)$_2$— representing substituents R22, which are optionally present in phenyl and Het1 groups representing R7 besides any other substituents R22, is 1 or 2, in another embodiment it is 1, in another embodiment it is 0.

In one embodiment of the invention, R8 is in any of its occurrences, independently of its other occurrences, selected from the series consisting of hydrogen and ($C_1$-$C_3$)-alkyl, in another embodiment from the series consisting of hydrogen and ($C_1$-$C_2$)-alkyl, in another embodiment from the series consisting of hydrogen and methyl, and in another embodiment R8 is hydrogen.

In one embodiment of the invention, R9 is selected from the series consisting of ($C_1$-$C_6$)-alkyl, ($C_3$-$C_7$)-cycloalkyl, ($C_3$-$C_7$)-cycloalkyl-($C_1$-$C_4$)-alkyl- and Het1-($C_1$-$C_4$)-alkyl-, in another embodiment from the series consisting of ($C_1$-$C_6$)-alkyl, ($C_3$-$C_7$)-cycloalkyl and ($C_3$-$C_7$)-cycloalkyl-($C_1$-$C_4$)-alkyl-, in another embodiment from the series consisting of ($C_1$-$C_6$)-alkyl and ($C_3$-$C_7$)-cycloalkyl, in another embodiment from the series consisting of ($C_1$-$C_6$)-alkyl, and in another embodiment from the series consisting of ($C_1$-$C_4$)-alkyl.

In one embodiment of the invention, R10 is selected from the series consisting of hydrogen, ($C_1$-$C_6$)-alkyl, ($C_3$-$C_7$)-cycloalkyl, ($C_3$-$C_7$)-cycloalkyl-($C_1$-$C_4$)-alkyl- and Het1-($C_1$-$C_4$)-alkyl-, in another embodiment from the series consisting of hydrogen, ($C_1$-$C_6$)-alkyl, ($C_3$-$C_7$)-cycloalkyl and ($C_3$-$C_7$)-cycloalkyl-($C_1$-$C_4$)-alkyl-, in another embodiment from the series consisting of hydrogen, ($C_1$-$C_6$)-alkyl and ($C_3$-$C_7$)-cycloalkyl, in another embodiment from the series consisting of hydrogen and ($C_1$-$C_6$)-alkyl, in another embodiment from the series consisting of hydrogen and ($C_1$-$C_4$)-alkyl, in another embodiment from the series consisting of ($C_1$-$C_6$)-alkyl, ($C_3$-$C_7$)-cycloalkyl, ($C_3$-$C_7$)-cycloalkyl-($C_1$-$C_4$)-alkyl- and Het1-($C_1$-$C_4$)-alkyl-, in another embodiment from the series consisting of ($C_1$-$C_6$)-alkyl, ($C_3$-$C_7$)-cycloalkyl, and ($C_3$-$C_7$)-cycloalkyl-($C_1$-$C_4$)-alkyl-, in another embodiment from the series consisting of ($C_1$-$C_6$)-alkyl and ($C_3$-$C_7$)-cycloalkyl, in another embodiment from the series consisting of ($C_1$-$C_6$)-alkyl, and in another embodiment from the series consisting of ($C_1$-$C_4$)-alkyl.

In one embodiment of the invention, R20 is selected from the series consisting of R24, fluorine, HO—, ($C_1$-$C_6$)-alkyl-O—, ($C_3$-$C_7$)-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, ($C_1$-$C_6$)-alkyl-S(O)$_n$—, ($C_3$-$C_7$)-cycloalkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, ($C_1$-$C_6$)-alkyl-O—, ($C_3$-$C_7$)-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, ($C_1$-$C_6$)-alkyl-O—, ($C_3$-$C_7$)-cycloalkyl-O—, HO—S(O)$_2$—O—, (HO)$_2$P(O)—O—, (HO)$_2$P(O)—O—CH$_2$—O—C(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, oxo, ($C_1$-$C_6$)-alkyl-O—, ($C_3$-$C_7$)-cycloalkyl-O—, R30-C(O)—O—, R30-NH—C(O)—O—, HO—S(O)$_2$—O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)- and R31-N(R32)-C(O)—, in another embodiment from the series consisting of R24, fluorine, HO—, ($C_1$-$C_6$)-alkyl-O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)—, R34-O—C(O)— and R31-N(R32)-S(O)$_2$—, in another embodiment from the series consisting of R24, fluorine, HO—, ($C_1$-$C_6$)-alkyl-O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)— and R34-O—C(O)—, in another embodiment from the series consisting of R24, fluorine, HO—, ($C_1$-$C_6$)-alkyl-O—, (HO)$_2$P(O)—O—, ($C_1$-$C_6$)-alkyl-S(O)$_n$—, R31-N(R32)-, R33-C(O)—N(R32)- and ($C_1$-$C_6$)-alkyl-S(O)$_2$—N(R32)-, in another embodiment from the series consisting of R31-N(R32)-, R33-C(O)—N(R32)- and ($C_1$-$C_6$)-alkyl-S(O)$_2$—N(R32)-, in another embodiment from the series consisting of R24, fluorine, HO—, $(C_1-C_6)$-alkyl-O—, $(HO)_2P(O)$—O—, $(C_1-C_6)$-alkyl-S(O)$_n$— and R31-N(R32)-, in another embodiment from the series consisting of R24, fluorine, HO—, $(C_1-C_6)$-alkyl-O— and $(HO)_2P(O)$—O—, in another embodiment from the series consisting of R24, fluorine, HO—, $(C_1-C_6)$-alkyl-O—, HO—S(O)$_2$—O—, $(HO)_2P(O)$—O— and $(HO)_2P(O)$—O—CH$_2$—O—C(O)—O—, in another embodiment from the series consisting of R24, fluorine, HO—, $(C_1-C_6)$-alkyl-O—, HO—S(O)$_2$—O— and $(HO)_2P(O)$—O—, in another embodiment from the series consisting of HO—, $(C_1-C_6)$-alkyl-O—, R30-C(O)—O—, R30-NH—C(O)—O—, HO—S(O)$_2$—O— and $(HO)_2P(O)$—O—, in another embodiment from the series consisting of HO—, R30-C(O)—O—, R30-NH—C(O)—O—, HO—S(O)$_2$—O— and $(HO)_2P(O)$—O—, in another embodiment from the series consisting of HO—, HO—S(O)$_2$—O— and $(HO)_2P(O)$—O—, in another embodiment from the series consisting of HO— and $(HO)_2P(O)$—O—, in another embodiment from the series consisting of R24, HO— and $(HO)_2P(O)$—O—, in another embodiment from the series consisting of R24 and HO—, and in another embodiment R20 is HO—, and in another embodiment R20 is R24, wherein in case that more than one substituent R20 is present, the substituents R20 are independently of one another defined as in any of these embodiments.

In one embodiment of the invention, R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, $(HO)_2P(O)$—O—, $(HO)_2P(O)$—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—, in another embodiment from the series consisting of $(C_1-C_4)$-alkyl, HO—$(C_1-C_4)$-alkyl-, R31-N(R32)-$(C_1-C_4)$-alkyl-, R24, fluorine, HO—, oxo, $(C_1-C_6)$-alkyl-O—, R30-C(O)—O—, R30-NH—C(O)—O—, HO—S(O)$_2$—O—, $(HO)_2P(O)$—O—, $(HO)_2P(O)$—O—CH$_2$—O—C(O)—O—, $(C_1-C_6)$-alkyl-S(O)$_n$—, R31-N(R32)-, R33-C(O)—N(R32)-, $(C_1-C_6)$-alkyl-S(O)$_2$—N(R32)-, R31-N(R32)-C(O)— and R34-O—C(O)—, in another embodiment from the series consisting of $(C_1-C_4)$-alkyl, HO—$(C_1-C_4)$-alkyl-, R31-N(R32)-$(C_1-C_4)$-alkyl-, R24, fluorine, HO—, oxo, $(C_1-C_6)$-alkyl-O—, R30-C(O)—O—, R30-NH—C(O)—O—, HO—S(O)$_2$—O—, $(HO)_2P(O)$—O—, $(HO)_2P(O)$—O—CH$_2$—O—C(O)—O—, R31-N(R32)-, R33-C(O)—N(R32)- and $(C_1-C_6)$-alkyl-S(O)$_2$—N(R32)-, in another embodiment from the series consisting of $(C_1-C_4)$-alkyl, HO—$(C_1-C_4)$-alkyl-, R31-N(R32)-$(C_1-C_4)$-alkyl-, R24, fluorine, HO—, oxo, $(C_1-C_6)$-alkyl-O—, HO—S(O)$_2$—O—, $(HO)_2P(O)$—O—, $(HO)_2P(O)$—O—CH$_2$—O—C(O)—O— and R31-N(R32)-, in another embodiment from the series consisting of $(C_1-C_4)$-alkyl, HO—$(C_1-C_4)$-alkyl-, fluorine, HO—, oxo, $(C_1-C_6)$-alkyl-O—, HO—S(O)$_2$—O—, $(HO)_2P(O)$—O— and $(HO)_2P(O)$—O—CH$_2$—O—C(O)—O—, in another embodiment from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, $(HO)_2P(O)$—O—, $(C_1-C_6)$-alkyl-S(O)$_n$—, R31-N(R32)-, R33-C(O)—N(R32)-, $(C_1-C_6)$-alkyl-S(O)$_2$—N(R32)- and R31-N(R32)-C(O)—, in another embodiment from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, $(C_1-C_6)$-alkyl-O—, $(C_3-C_7)$-cycloalkyl-O—, HO—S(O)$_2$—O—, $(HO)_2P(O)$—O—, $(C_1-C_6)$-alkyl-S(O)$_n$—, R31-N(R32)-, R33-C(O)—N(R32)- and R31-N(R32)-C(O)—, in another embodiment from the series consisting of $(C_1-C_4)$-alkyl, HO—$(C_1-C_4)$-alkyl-, R31-N(R32)-$(C_1-C_4)$-alkyl-, fluorine, HO—, $(C_1-C_6)$-alkyl-O—, $(C_3-C_7)$-cycloalkyl-O—, HO—S(O)$_2$—O—, $(HO)_2P(O)$—O—, R31-N(R32)-, R33-C(O)—N(R32)- and R31-N(R32)-C(O)—, in another embodiment from the series consisting of $(C_1-C_4)$-alkyl, HO—$(C_1-C_4)$-alkyl-, R31-N(R32)-$(C_1-C_4)$-alkyl-, fluorine, HO—, $(C_1-C_6)$-alkyl-O—, $(C_3-C_7)$-cycloalkyl-O—, HO—S(O)$_2$—O—, $(HO)_2P(O)$—O—, R31-N(R32)-, R33-C(O)—N(R32)- and R31-N(R32)-C(O)—, in another embodiment from the series consisting of $(C_1-C_4)$-alkyl, HO—$(C_1-C_4)$-alkyl-, R31-N(R32)-$(C_1-C_4)$-alkyl-, fluorine, HO—, $(C_1-C_6)$-alkyl-O—, $(C_3-C_7)$-cycloalkyl-O—, HO—S(O)$_2$—O—, $(HO)_2P(O)$—O—, R31-N(R32)-, R33-C(O)—N(R32)- and R31-N(R32)-C(O)—, in another embodiment from the series consisting of $(C_1-C_4)$-alkyl, fluorine, HO—, oxo, HO—S(O)$_2$—O—, $(HO)_2P(O)$—O— and $(HO)_2P(O)$—O—CH$_2$—O—C(O)—O—, in another embodiment from the series consisting of $(C_1-C_4)$-alkyl, fluorine, HO—, oxo, HO—S(O)$_2$—O— and $(HO)_2P(O)$—O—, in another embodiment from the series consisting of $(C_1-C_4)$-alkyl, fluorine, HO—, oxo and $(HO)_2P(O)$—O—, in another embodiment from the series consisting of $(C_1-C_4)$-alkyl, fluorine, HO— and oxo, in another embodiment from the series consisting of $(C_1-C_4)$-alkyl, HO—$(C_1-C_4)$-alkyl-, fluorine, HO—, $(C_1-C_6)$-alkyl-O—, HO—S(O)$_2$—O— and $(HO)_2P(O)$—O—, in another embodiment from the series consisting of $(C_1-C_4)$-alkyl, fluorine, HO—, HO—S(O)$_2$—O— and $(HO)_2P(O)$—O—, in another embodiment from the series consisting of $(C_1-C_4)$-alkyl, fluorine, HO—, HO—S(O)$_2$—O— and $(HO)_2P(O)$—O—, in another embodiment from the series consisting of $(C_1-C_4)$-alkyl, fluorine, HO— and $(HO)_2P(O)$—O—, in another embodiment from the series consisting of $(C_1-C_4)$-alkyl, fluorine and HO—, wherein in case that more than one substituent R21 is present, the substituents R21 are independently of one another defined as in any of these embodiments. In one embodiment, substituents R21 which are bonded to a ring nitrogen atom, as can occur in the case of the group Het2 or the ring which can be formed by R5 and R6 together with the nitrogen atom carrying them, are selected from the series consisting of $(C_1-C_4)$-alkyl, HO—$(C_1-C_4)$-alkyl-, R31-N(R32)-$(C_1-C_4)$-alkyl- and R24, wherein R24 is bonded via a ring carbon atom, in another embodiment from the series consisting of $(C_1-C_4)$-alkyl.

In one embodiment of the invention, R22 is selected from the series consisting of halogen, $(C_1-C_4)$-alkyl, HO—$(C_1-C_4)$-alkyl-, $(C_3-C_7)$-cycloalkyl, HO—, oxo, $(C_1-C_6)$-alkyl-O—, HO—S(O)$_2$—O—, $(HO)_2P(O)$—O—, $(HO)_2P(O)$—O—CH$_2$—O—C(O)—O—, $(C_1-C_6)$-alkyl-S(O)$_n$—, R31-N(R32)-, R33-C(O)—N(R32)-, R33-O—C(O)—N(R32)-, $(C_1-C_6)$-alkyl-S(O)$_2$—N(R32)-, NC—, R31-N(R32)-C(O)— and R31-N(R32)-S(O)$_2$—, in another embodiment from the series consisting of halogen, $(C_1-C_4)$-alkyl, HO—$(C_1-C_4)$-alkyl-, $(C_3-C_7)$-cycloalkyl, HO—, oxo, $(C_1-C_6)$-alkyl-O—, HO—S(O)$_2$—O—, $(HO)_2P(O)$—O—, $(HO)_2P(O)$—O—CH$_2$—O—C(O)—O—, $(C_1-C_6)$-alkyl-S(O)$_n$—, R31-N(R32)-, NC— and R31-N(R32)-C(O)—, in another embodiment from the series consisting of halogen, $(C_1-C_4)$-alkyl, HO—, oxo, $(C_1-C_6)$-alkyl-O—, HO—S(O)$_2$—O—, $(HO)_2P(O)$—O—, $(HO)_2P(O)$—O—CH$_2$—O—C(O)—O—, $(C_1-C_6)$-alkyl-S(O)$_n$—, R31-N(R32)-, NC— and R31-N(R32)-C(O)—, in another embodiment from the series consisting of halogen, $(C_1-C_4)$-alkyl, HO—, $(C_1-C_6)$-alkyl- O—, HO—S(O)₂—O—, (HO)₂P(O)—O—, (HO)₂P(O)—O—CH₂—O—C(O)—O—, R31-N(R32)-, NC— and R31-N(R32)-C(O)—, in another embodiment from the series consisting of halogen, (C₁-C₄)-alkyl, HO—(C₁-C₄)-alkyl-, (C₃-C₇)-cycloalkyl, HO—, oxo, (C₁-C₆)-alkyl-O—, (C₃-C₇)-cycloalkyl-O—, HO—S(O)₂—O—, (HO)₂P(O)—O—, (C₁-C₆)-alkyl-S(O)ₙ—, R31-N(R32)-, R33-C(O)—N(R32)-, R33-O—C(O)—N(R32)-, (C₁-C₆)-alkyl-S(O)₂—N(R32)-, NC—, R33-C(O)— and R31-N(R32)-C(O)—, in another embodiment from the series consisting of halogen, (C₁-C₄)-alkyl, HO—(C₁-C₄)-alkyl-, (C₃-C₇)-cycloalkyl, HO—, (C₁-C₆)-alkyl-O—, (C₃-C₇)-cycloalkyl-O—, HO—S(O)₂—O—, (HO)₂P(O)—O—, (C₁-C₆)-alkyl-S(O)ₙ—, R31-N(R32)-, R33-C(O)—N(R32)-, NC—, R33-C(O)— and R31-N(R32)-C(O)—, in another embodiment from the series consisting of halogen, (C₁-C₄)-alkyl, HO—(C₁-C₄)-alkyl-, (C₃-C₇)-cycloalkyl, HO—, (C₁-C₆)-alkyl-O—, (C₃-C₇)-cycloalkyl-O—, HO—S(O)₂—O—, (HO)₂P(O)—O—, (C₁-C₆)-alkyl-S(O)ₙ—, R31-N(R32)-, R33-C(O)—N(R32)- and R31-N(R32)-C(O)—, in another embodiment from the series consisting of halogen, (C₁-C₄)-alkyl, HO—, (C₁-C₆)-alkyl-O—, HO—S(O)₂—O—, (HO)₂P(O)—O—, R31-N(R32)- and NC—, in another embodiment from the series consisting of halogen, (C₁-C₄)-alkyl, HO—, (C₁-C₆)-alkyl-O—, HO—S(O)₂—O—, (HO)₂P(O)—O— and NC—, in another embodiment from the series consisting of halogen, (C₁-C₄)-alkyl, HO—, (C₁-C₆)-alkyl-O—, (HO)₂P(O)—O— and NC—, in another embodiment from the series consisting of halogen, (C₁-C₄)-alkyl, (C₁-C₆)-alkyl-O— and NC—, in another embodiment from the series consisting of halogen, (C₁-C₄)-alkyl and (C₁-C₆)-alkyl-O—, in another embodiment from the series consisting of halogen and (C₁-C₄)-alkyl, wherein in case that more than one substituent R22 is present, the substituents R22 are independently of one another defined as in any of these embodiments. In one embodiment, substituents R22 which are bonded to a ring nitrogen atom, as can occur in the case of the group Het1 and R24, are selected from the series consisting (C₁-C₄)-alkyl, HO—(C₁-C₄)-alkyl- and (C₃-C₇)-cycloalkyl, in another embodiment from the series consisting of (C₁-C₄)-alkyl.

The monocyclic or bicyclic group R24 can be 3-membered, 4-membered, 5-membered, 6-membered, 7-membered, 8-membered, 9-membered or 10-membered. In one embodiment of the invention, a monocyclic group R24 is 3-membered, 4-membered, 5-membered, 6-membered or 7-membered, and a bicyclic group R24 is 6-membered, 7-membered, 8-membered, 9-membered or 10-membered. In one embodiment of the invention, R24 is a monocyclic ring, in another embodiment a 3-membered to 7-membered monocyclic ring, in another embodiment a 3-membered to 6-membered monocyclic ring, in another embodiment a 4-membered to 6-membered monocyclic ring, in another embodiment a 5-membered or 6-membered monocyclic ring, in another embodiment a bicyclic ring, in another embodiment a 6-membered to 10-membered bicyclic ring, in another embodiment a 7-membered to 10-membered bicyclic ring, in another embodiment a 7-membered to 9-membered bicyclic ring. The two cycles in a bicyclic group R24 can be fused or form a bridged bicycle or a spirocycle. The monocyclic or bicyclic ring R24 can be saturated, i.e. not contain any double bonds within the ring system, or be partially unsaturated, i.e. contain one or more double bonds within the ring system, for example, one two, three or four double bonds, or one, two or three double bonds, or one or two double bonds, or one double bond, but is not fully aromatic, i.e. it does not contain a cyclic system of six delocalized pi electrons in the case of a monocycle or of ten delocalized pi electrons in the case of a bicycle, or it can be aromatic. The number of double bonds which can be present in a ring, depends on the type of the ring system and the ring size. Partially unsaturated rings R24 include also bicyclic ring systems in which one of the two cycles is aromatic and the other is not aromatic. In one embodiment, R24 is a saturated or aromatic ring, in another embodiment a saturated ring, in another embodiment an aromatic ring.

The ring R24 can be carbocyclic, i.e. contain 0 (zero) ring heteroatoms, or heterocyclic, i.e. contain 1, 2, 3 or 4 identical or different ring heteroatoms. In one embodiment, the number of ring heteroatoms which are present in R24 is 0, 1, 2 or 3, in another embodiment 0, 1 or 2, in another embodiment 0 or 1. In one embodiment of the invention, R24 is in any of its occurrences, independently of its other occurrences, a carbocyclic ring, and in another embodiment it is a heterocyclic ring. In a bicyclic ring R24, ring heteroatoms can be present in one of the two rings or in both rings in any suitable positions. In bridged and fused bicyclic rings, ring nitrogen atoms can also be present in bridgehead positions and fusion positions. In one embodiment of the invention, a 3-membered ring R24 is carbocyclic ring, specifically a cyclopropane ring, i.e., in this case the group R24 is a cyclopropyl group. In one embodiment, ring heteroatoms which are present in R24, are selected from the series consisting of nitrogen and oxygen, in another embodiment from the series consisting of nitrogen and sulfur, and in another embodiment they are nitrogen atoms. R24 can be bonded via any ring carbon atom and any ring nitrogen atom which has a free binding position. In a bicyclic group R24, the ring atom via which R24 is bonded, can be present in a saturated ring, a partially unsaturated ring or in an aromatic ring. In one embodiment of the invention, R24 is bonded in any of its occurrences, independently of its other occurrences, via a ring carbon atom, in another embodiment via a ring nitrogen atom.

Types of cyclic groups which are comprised by the definition of R24, are cycloalkyl groups, bicycloalkyl groups, phenyl groups, naphthyl groups including naphthalen-1-yl groups and naphthalen-2-yl groups, partially hydrogenated naphthyl groups such as 1,2,3,4-tetrahydronaphthalenyl groups, monocyclic and bicyclic aromatic heterocyclic groups such as the group Het1, for example, and saturated and partially unsaturated monocyclic and bicyclic heterocyclic groups such as the group Het2. The explanations given above and below with respect to such groups apply correspondingly to such groups representing R24, as do the explanations given above with respect to heterocyclic groups in general. Examples of groups, from any one or more of which the group R24 is selected in one embodiment of the invention, are the groups of the following formulae,

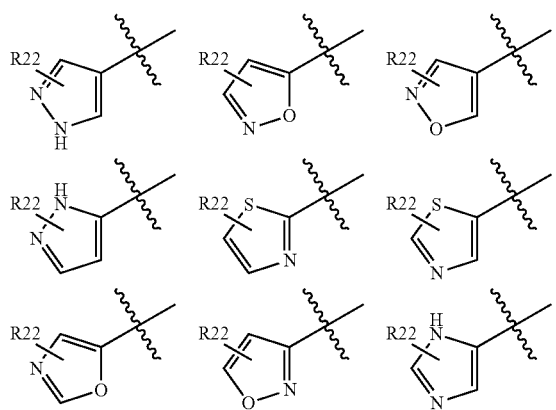

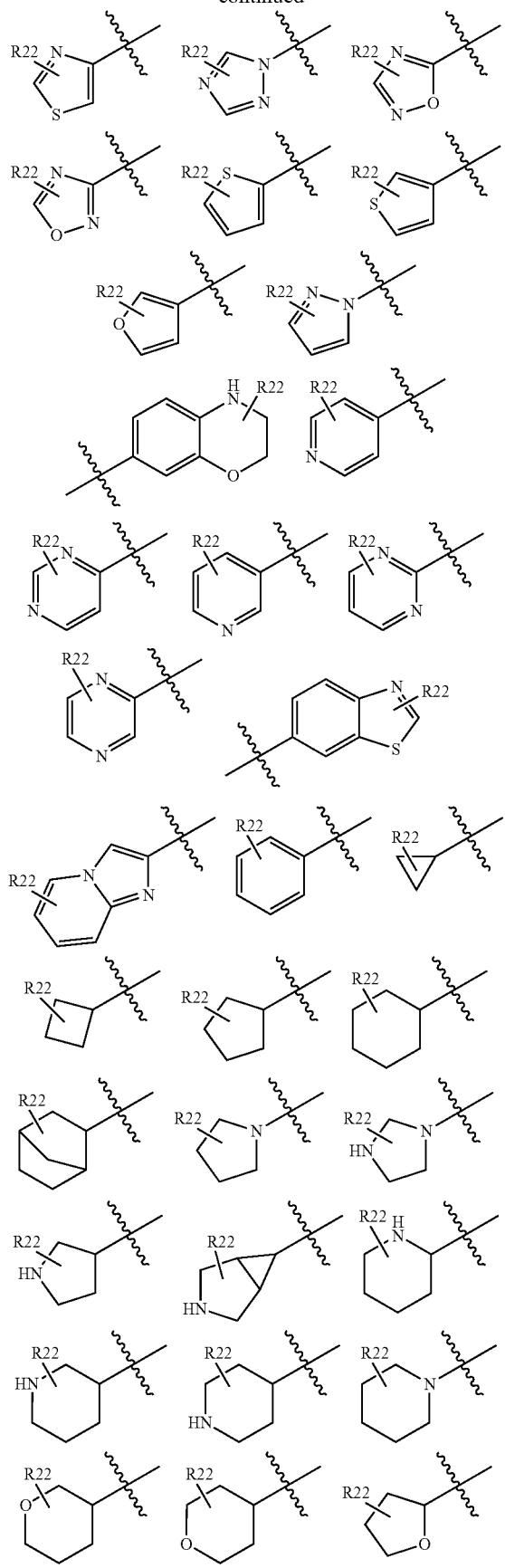
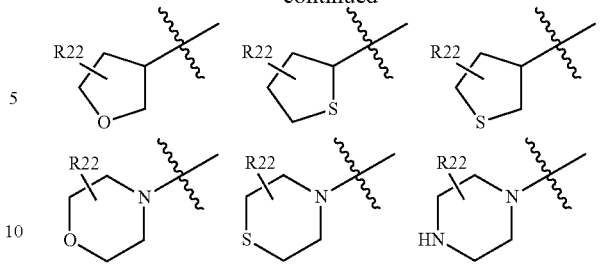

in which the line crossed with the symbol

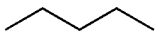

represents the free bond via which the group is bonded. The bond originating at the substituent R22 which is depicted in these formulae, which is not directed to a specific atom, indicates that these groups are optionally substituted by one or more identical or different substituents R22, i.e. they are unsubstituted or substituted by one or more identical or different substituents R22, and that the substituents R22 can be present in any positions.

In one embodiment of the invention, the number of identical or different substituents R22 which are optionally present in the group R24, is 1, 2, 3 or 4, in another embodiment it is 1, 2 or 3, in another embodiment it is 1 or 2, in another embodiment it is 1, in another embodiment it is 0. In one embodiment, the number of oxo groups representing substituents R22, which are optionally present in R24 besides any other substituents R22, is 1 or 2, in another embodiment it is 1, in another embodiment it is 0. In one embodiment, the number of groups selected from the series consisting of R31-N(R32)-C(O)—, R34-O—C(O)— and R31-N(R32)-S(O)$_2$— representing substituents R22, which are optionally present in R24 besides any other substituents R22, is 1 or 2, in another embodiment it is 1, in another embodiment it is 0.

In one embodiment of the invention, R30 is in any of its occurrences, independently of its other occurrences, selected from the series consisting of ($C_1$-$C_6$)-alkyl, ($C_3$-$C_7$)-cycloalkyl and ($C_3$-$C_7$)-cycloalkyl-($C_1$-$C_4$)-alkyl-, in another embodiment from the series consisting of ($C_1$-$C_6$)-alkyl, in another embodiment from the series consisting of ($C_1$-$C_4$)-alkyl, in another embodiment from the series consisting of ($C_1$-$C_3$)-alkyl, in another embodiment from the series consisting of ($C_1$-$C_2$)-alkyl, and in another embodiment R30 is methyl.

In one embodiment of the invention, R31 and R32 are in any of their occurrences, independently of other occurrences, and independently of one another, selected from the series consisting of hydrogen, ($C_1$-$C_6$)-alkyl, ($C_3$-$C_7$)-cycloalkyl and ($C_3$-$C_7$)-cycloalkyl-($C_1$-$C_4$)-alkyl-, in another embodiment from the series consisting of hydrogen and ($C_1$-$C_6$)-alkyl, in another embodiment from the series consisting of hydrogen and ($C_1$-$C_4$)-alkyl, in another embodiment from the series consisting of hydrogen and methyl, or the groups R31 and R32, together with the nitrogen atom carrying them, form a 4-membered to 7-membered, monocyclic saturated heterocycle which, in addition to the nitrogen atom carrying R31 and R32, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl. In another embodiment, R31 and R32 are in any of their occurrences, independently of other occurrences, and independently of one another, selected from the series consisting of hydrogen, $(C_1-C_6)$-alkyl, $(C_3-C_7)$-cycloalkyl and $(C_3-C_7)$-cycloalkyl-$(C_1-C_4)$-alkyl-, in another embodiment from the series consisting of hydrogen and $(C_1-C_6)$-alkyl, in another embodiment from the series consisting of hydrogen and $(C_1-C_4)$-alkyl, in another embodiment from the series consisting of hydrogen and methyl.

The monocyclic heterocycle which can be formed by the groups R31 and R32 together with the nitrogen atom carrying them, which heterocycle is thus bonded via a ring nitrogen atom, can be 4-membered, 5-membered, 6-membered or 7-membered. In one embodiment of the invention, the heterocycle formed by the groups R31 and R32 together with the nitrogen atom carrying them, is 5-membered or 6-membered, in another embodiment it is 6-membered. In one embodiment, the further ring heteroatom which is optionally present in a heterocycle formed by the groups R31 and R32 together with the nitrogen atom carrying them, is selected from the series consisting of nitrogen and oxygen, in another embodiment it is a nitrogen atom, and in another embodiment it is an oxygen atom. In one embodiment of the invention, the number of substituents selected from the series consisting of fluorine and $(C_1-C_4)$-alkyl, which can be present in a ring formed by the groups R31 and R32 together with the nitrogen atom carrying them, is 1, 2 or 3, in another embodiment 1 or 2, in another embodiment 1, in another embodiment it is 0. In one embodiment of the invention, substituents which can be present in a ring formed by the groups R31 and R32 together with the nitrogen atom carrying them, are fluorine substituents, and in another embodiment they are $(C_1-C_4)$-alkyl substituents, for example methyl substituents, and in another embodiment are substituents in such a ring bonded to a ring nitrogen atom selected from the series consisting of $(C_1-C_4)$-alkyl. Examples of heterocyclic groups, from any one or more of which the heterocyclic groups formed by the groups R31 and R32 together with the nitrogen atom carrying them is selected in one embodiment of the invention, are azetidin-1-yl, pyrrolidin-1-yl, piperidin-1-yl, morpholin-4-yl, thiomorpholin-4-yl, and 4-methylpiperazin-1-yl.

In one embodiment of the invention, R33 is in any of its occurrences, independently of its other occurrences, selected from the series consisting of $(C_1-C_6)$-alkyl, $(C_3-C_7)$-cycloalkyl and $(C_3-C_7)$-cycloalkyl-$(C_1-C_4)$-alkyl-, in another embodiment from the series consisting of $(C_1-C_6)$-alkyl, in another embodiment from the series consisting of $(C_1-C_4)$-alkyl, in another embodiment from the series consisting of $(C_1-C_3)$-alkyl, in another embodiment from the series consisting of $(C_1-C_2)$-alkyl, and in another embodiment R33 is methyl.

In one embodiment of the invention, R34 is in any of its occurrences, independently of its other occurrences, selected from the series consisting of hydrogen, $(C_1-C_6)$-alkyl, $(C_3-C_7)$-cycloalkyl and $(C_3-C_7)$-cycloalkyl-$(C_1-C_4)$-alkyl-, in another embodiment from the series consisting of hydrogen and $(C_1-C_6)$-alkyl, in another embodiment from the series consisting of hydrogen and $(C_1-C_4)$-alkyl, in another embodiment from the series consisting of hydrogen and $(C_1-C_3)$-alkyl, in another embodiment from the series consisting of $(C_1-C_4)$-alkyl, in another embodiment from the series consisting of $(C_1-C_3)$-alkyl, and in another embodiment R34 is hydrogen.

In one embodiment of the invention, the aromatic group Het1 is in any of its occurrences, independently of other occurrences, a 5-membered heterocycle which comprises one ring heteroatom which is selected from the series consisting of nitrogen, oxygen and sulfur, and a further ring heteroatom which is a ring nitrogen atom, or it is 6-membered heterocycle which comprises one or two ring nitrogen atoms, in another embodiment Het1 is selected from the series consisting of the aromatic heterocycles pyrazole, imidazole, isoxazole, oxazole, thiazole, pyridine, pyrimidine and pyrazine, in another embodiment from the series consisting of pyrazole, isoxazole, oxazole, thiazole, pyridine and pyrimidine, in another embodiment from the series consisting of pyrazole, isoxazole, oxazole, thiazole and pyridine, in another embodiment from the series consisting of pyrazole, isoxazole, thiazole and pyridine, in another embodiment from the series consisting of pyrazole, isoxazole and pyridine, in another embodiment from the series consisting of pyrazole, isoxazole and thiazole, which are all unsubstituted or substituted as indicated. In one embodiment, the group Het1 is bonded via a ring carbon atom. In one embodiment, the number of substituents which are optionally present in a group Het1, is 1, 2 or 3, in another embodiment 1 or 2, in another embodiment 1, in another embodiment it is 0. In case a certain group Het1 is optionally substituted by substituents selected from the series consisting of halogen, $(C_1-C_4)$-alkyl and $(C_1-C_4)$-alkyl-O— and no other substitution is specified for this group Het1, in one embodiment such a group Het1 is optionally substituted by substituents selected from the series consisting of halogen and $(C_1-C_4)$-alkyl, and, in another embodiment, a substituent in such a group Het1 which is bonded to a ring nitrogen atom, such as in a pyrrole, pyrazole or imidazole ring, is selected from the series consisting of $(C_1-C_4)$-alkyl.

The heterocyclic group Het2 can be 4-membered, 5-membered, 6-membered, 7-membered, 8-membered, 9-membered or 10-membered. In one embodiment of the invention, a monocyclic group Het2 is 4-membered, 5-membered, 6-membered or 7-membered, and a bicyclic group Het2 is 6-membered, 7-membered, 8-membered, 9-membered or 10-membered. In one embodiment of the invention, Het2 is in any of its occurrences, independently of other occurrences, a monocyclic ring, in another embodiment a 4-membered to 7-membered monocyclic ring, in another embodiment a 4-membered to 6-membered monocyclic ring, in another embodiment a 5-membered or 6-membered monocyclic ring, in another embodiment a bicyclic ring, in another embodiment a 6-membered to 10-membered bicyclic ring, in another embodiment a 7-membered to 10-membered bicyclic ring, in another embodiment a 7-membered to 9-membered bicyclic ring. The two cycles in a bicyclic group Het2, can be fused or form a bridged bicycle or a spirocycle. In one embodiment, the group Het2 is saturated or contains one double bond within the ring, in another embodiment it is saturated. In one embodiment, the further ring heteroatom which is optionally present in a group Het2, is selected from the series consisting of nitrogen and oxygen, in another embodiment it is a nitrogen atom, and in another embodiment it is an oxygen atom. Het2 can be bonded via any ring carbon atom and any ring nitrogen atom which has a free binding position. In one embodiment of the invention, Het2 is bonded in any of its occurrences, independently of its other occurrences, via a ring carbon atom, in another embodiment via a ring nitrogen atom. Examples of heterocyclic groups, from any one or more of which Het2 is selected in one embodiment of the invention, are oxetanyl, azetidinyl, tetrahydrofuranyl, tetrahydrothiophenyl, pyrrolidinyl, tetrahydropyranyl, tetrahydrothiopyranyl, piperidinyl, azepanyl, morpholinyl, thiomorpholinyl, piperazinyl and 3-azabicyclo[3.1.0]hexyl, which in one embodiment are bonded via a ring carbon atom and, for example, are the residues oxetan-3-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-2-yl, pyrrolidin-3-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, piperidin-2-yl, piperidin-3-yl, piperidin-4-yl and 3-azabicyclo[3.1.0]hex-6-yl.

If one or both of the numbers p and q is 0 (zero), one or both of the parenthesized corners of the cycloalkane ring depicted in formula I are not present, and the ring carbon atom carrying the groups R2 and R3 is bonded via a single bond to one or both of the ring carbons which are adjacent to the atom carrying the oxygen atom which links the cycloalkane ring to the chroman ring. In one embodiment of the invention, one of the numbers p and q, for example p, is selected from the series consisting of 0 and 1, and the other of the numbers p and q, for example q, is 0. In another embodiment, both of the numbers p and q are 0, and the respective compounds are compounds of the formula Ie. In another embodiment of the invention, one of the numbers p and q is 0 and the other is 1, and the respective compounds are compounds of the formula If. In another embodiment of the invention, both of the numbers p and q are 1, and the respective compounds are compounds of the formula Ig. The groups Ar and R1 to R4 in the compounds of the formulae Ie, If and Ig are defined as in the compounds of the formula I.

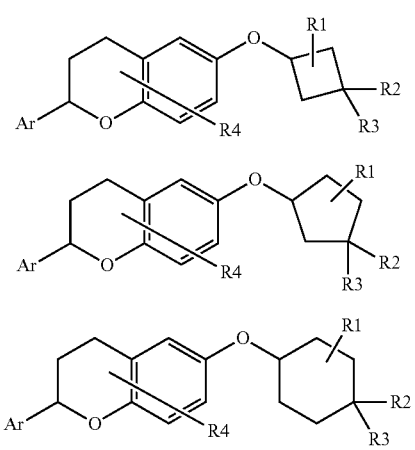

In one embodiment of the invention, the substituents in a phenyl group in any occurrence in a compound of the formula I, independently of any other occurrences, are selected from the series consisting of halogen and $(C_1-C_4)$-alkyl, unless specified otherwise. In one embodiment, the number of substituents in a phenyl group is 1, 2 or 3, in another embodiment 1 or 2, in another embodiment 1, in another embodiment it is 0, unless specified otherwise.

In one embodiment of the invention, the chiral carbon atom in position 2 of the chroman ring in a compound of the formula I is present, or is essentially present, for example with a molar ratio of the two stereoisomers of 98:2, or 99:1, or greater, in uniform configuration, either in R configuration or in S configuration, as is indicated by the wavy wedge in the compound of the formula Ih. In another embodiment of the invention, the chiral carbon atom in position 2 of the chroman ring in a compound of the formula I is present, or is essentially present, for example with a molar ratio of the two stereoisomers of 98:2, or 99:1, or greater, in the configuration depicted in formula Ik, i.e. in the respective compound of the formula I the group Ar is located above the plane which may be assumed to be formed by the chroman ring arranged as depicted in formula Ik, which configuration is R configuration in case all groups R4 are hydrogen. In another embodiment of the invention, the chiral carbon atom in position 2 of the chroman ring in a compound of the formula I is present, or is essentially present, for example with a molar ratio of the two stereoisomers of 98:2, or 99:1, or greater, in the configuration depicted in formula Im, i.e. in the respective compound of the formula I the group Ar is located below the plane which may be assumed to be formed by the chroman ring arranged as depicted in formula Im, which configuration is S configuration in case all groups R4 are hydrogen.

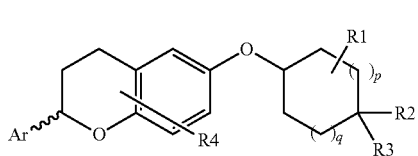

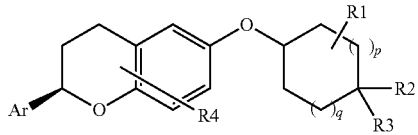

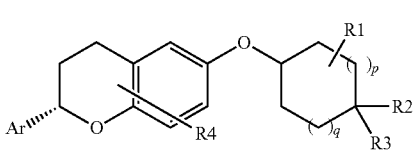

The groups Ar, R1 to R4 and the numbers p and q in the compounds of the formulae Ih, Ik and Im are defined as in the compounds of the formula I.

In one embodiment of the invention, the group R2 and the oxygen atom, which links the cycloalkane ring depicted in formula I to the chroman ring, are in cis position with respect to one another, i.e. they are located on the same side of the plane, for example above the plane, which may be assumed to be formed by the cycloalkane ring arranged as depicted in formula In, and the respective compounds are compounds of the formula In. In another embodiment of the invention, the group R2 and the oxygen atom, which links the cycloalkane ring depicted in formula I to the chroman ring, are in trans position with respect to one another, i.e. they are located on opposite sides of the plane which may be assumed to be formed by the cycloalkane ring arranged as depicted in formula Io, and the respective compounds are compounds of the formula Io.

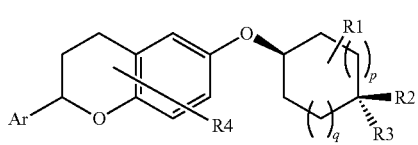

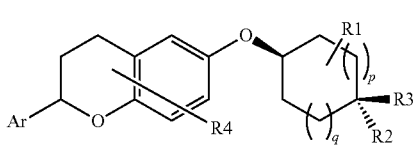

A subject of the invention are all compounds of the formula I wherein any one or more structural elements such as groups, residues, substituents, numbers and stereochemical configurations are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention.

As an example of compounds of the invention which with respect to any structural elements are defined as in specified embodiments of the invention or definitions of such elements, compounds of the formula I may be mentioned, wherein Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_3-C_7)$-cycloalkyl-$(C_1-C_4)$-alkyl-, HO—, $(C_1-C_6)$-alkyl-O—, $(C_3-C_7)$-cycloalkyl-O— and $(C_3-C_7)$-cycloalkyl-$(C_1-C_4)$-alkyl-O;

R1 is hydrogen or one or more identical or different substituents selected from the series consisting of fluorine and $(C_1-C_4)$-alkyl;

R2 is selected from the series consisting of $(C_1-C_6)$-alkyl, HO—, $(C_1-C_6)$-alkyl-O—, $(C_1-C_6)$-alkyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, wherein $(C_1-C_6)$-alkyl is unsubstituted or substituted by one or more identical or different substituents R20;

R3 is selected from the series consisting of hydrogen and $(C_1-C_6)$-alkyl, wherein $(C_1-C_6)$-alkyl is unsubstituted or substituted by one or two identical or different substituents selected from the series consisting of $(C_3-C_7)$-cycloalkyl and phenyl;

or the groups R2 and R3 together are oxo;

R4 is hydrogen or one or more identical or different substituents selected from the series consisting of halogen, $(C_1-C_4)$-alkyl and $(C_1-C_4)$-alkyl-O—;

R5 and R6 are independently of one another selected from the series consisting of hydrogen, $(C_1-C_6)$-alkyl, $(C_2-C_6)$-alkenyl, $(C_3-C_7)$-cycloalkyl, Het1 and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, and Het1 is unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of $(C_1-C_6)$-alkyl, $(C_3-C_7)$-cycloalkyl, phenyl, Het1 and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, and phenyl and Het1 all are unsubstituted or substituted by one or more identical or different substituents R22;

R8 is selected from the series consisting of hydrogen and $(C_1-C_4)$-alkyl;

R9 is selected from the series consisting of $(C_1-C_6)$-alkyl and $(C_3-C_7)$-cycloalkyl;

R10 is selected from the series consisting of hydrogen, $(C_1-C_6)$-alkyl and $(C_3-C_7)$-cycloalkyl;

R20 is selected from the series consisting of R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, $(C_1-C_6)$-alkyl-S(O)$_n$—, R31-N(R32)-, R33-C(O)—N(R32)-, $(C_1-C_6)$-alkyl-S(O)$_2$—N(R32)- and R31-N(R32)-C(O)—;

R22 is selected from the series consisting of halogen, $(C_1-C_4)$-alkyl, HO—$(C_1-C_4)$-alkyl-, $(C_3-C_7)$-cycloalkyl, HO—, oxo, $(C_1-C_6)$-alkyl-O—, $(C_3-C_7)$-cycloalkyl-O—, HO—S(O)$_2$—O—, (HO)$_2$P(O)—O—, $(C_1-C_6)$-alkyl-S(O)$_n$—, R31-N(R32)-, R33-C(O)—N(R32)-, R33-O—C(O)—N(R32)-, $(C_1-C_6)$-alkyl-S(O)$_2$—N(R32)-, NC—, R33-C(O)— and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R30 and R33 are independently of one another selected from the series consisting of $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R31 and R32 are independently of one another selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R34 is selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

Het1 is a 5-membered or 6-membered, monocyclic, aromatic heterocycle which comprises 1, 2 or 3 identical or different ring heteroatoms selected from the series consisting of nitrogen, oxygen and sulfur, and which is unsubstituted or substituted by one or more identical or different substituents selected from the series consisting of halogen, $(C_1-C_4)$-alkyl and $(C_1-C_4)$-alkyl-O—, unless specified otherwise;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, $(C_1-C_4)$-alkyl and $(C_1-C_4)$-alkyl-O—, unless specified otherwise;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_3-C_7)$-cycloalkyl-$(C_1-C_4)$-alkyl-, HO—, $(C_1-C_6)$-alkyl-O—, $(C_3-C_7)$-cycloalkyl-O— and $(C_3-C_7)$-cycloalkyl-$(C_1-C_4)$-alkyl-O—;

R1 is hydrogen or one or more identical or different substituents selected from the series consisting of fluorine and $(C_1-C_4)$-alkyl;

R2 is selected from the series consisting of $(C_1-C_6)$-alkyl, HO—, $(C_1-C_6)$-alkyl-O—, R5-N(R6)-, R7-C(O)—N(R8)-, R9-N(R10)-C(O)—N(R8)- and R5-N(R6)-C(O)—, wherein $(C_1-C_6)$-alkyl is unsubstituted or substituted by one or more identical or different substituents R20;

R3 is selected from the series consisting of hydrogen and $(C_1-C_6)$-alkyl, wherein $(C_1-C_6)$-alkyl is unsubstituted or substituted by one or two identical or different substituents selected from the series consisting of $(C_3-C_7)$-cycloalkyl and phenyl;

or the groups R2 and R3 together are oxo;

R4 is hydrogen or one or more identical or different substituents selected from the series consisting of halogen, $(C_1-C_4)$-alkyl and $(C_1-C_4)$-alkyl-O—;

R5 and R6 are independently of one another selected from the series consisting of hydrogen, $(C_1-C_6)$-alkyl, $(C_3-C_7)$-cycloalkyl and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of $(C_1-C_6)$-alkyl, $(C_3-C_7)$-cycloalkyl and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21;

R8 is selected from the series consisting of hydrogen and $(C_1-C_4)$-alkyl;

R9 is selected from the series consisting of $(C_1-C_6)$-alkyl and $(C_3-C_7)$-cycloalkyl;

R10 is selected from the series consisting of hydrogen, $(C_1-C_6)$-alkyl and $(C_3-C_7)$-cycloalkyl-;

R20 is selected from the series consisting of R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, $(C_1-C_6)$-alkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, $(C_1-C_6)$-alkyl-O—, $(C_3-C_7)$-cycloalkyl-O—, HO—S(O)$_2$—O—, (HO)$_2$P(O)—O—, $(C_1-C_6)$-alkyl-S(O)$_n$—, R31-N(R32)-, R33-C(O)—N(R32)- and R31-N(R32)-C(O)—;

R22 is selected from the series consisting of halogen, $(C_1-C_4)$-alkyl, HO—$(C_1-C_4)$-alkyl-, $(C_3-C_7)$-cycloalkyl, HO—, $(C_1-C_6)$-alkyl-O—, $(C_3-C_7)$-cycloalkyl-O—, HO—S(O)$_2$—O—, (HO)$_2$P(O)—O—, $(C_1-C_6)$-alkyl-S(O)$_n$—, R31-N(R32)-, R33-C(O)—N(R32)-, NC—, R33-C(O)— and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R30 and R33 are independently of one another selected from the series consisting of $(C_1-C_6)$-alkyl, $(C_3-C_7)$-cycloalkyl and $(C_3-C_7)$-cycloalkyl-$(C_1-C_4)$-alkyl-;

R31 and R32 are independently of one another selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

R34 is selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, $(C_1-C_4)$-alkyl and $(C_1-C_4)$-alkyl-O—, unless specified otherwise;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_1-C_6)$-alkyl-O— and $(C_3-C_7)$-cycloalkyl-O—;

R1 is hydrogen or one or more identical or different substituents selected from the series consisting of fluorine and $(C_1-C_4)$-alkyl;

R2 is selected from the series consisting of $(C_1-C_6)$-alkyl, HO—, R5-N(R6)-, R7-C(O)—N(R8)- and R5-N(R6)-C(O)—, wherein $(C_1-C_6)$-alkyl is unsubstituted or substituted by one or more identical or different substituents R20;

R3 is hydrogen;

R4 is hydrogen or one or more identical or different substituents selected from the series consisting of halogen and $(C_1-C_4)$-alkyl;

one of the groups R5 and R6 is selected from the series consisting of hydrogen and $(C_1-C_6)$-alkyl, and the other of the groups R5 and R6 is selected from the series consisting of $(C_1-C_6)$-alkyl, $(C_3-C_7)$-cycloalkyl and Het2, wherein $(C_1-C_6)$-alkyl all are unsubstituted or substituted by one or more identical or different substituents R20, and $(C_3-C_7)$-cycloalkyl and Het2 all are unsubstituted or substituted by one or more identical or different substituents R21;

R7 is selected from the series consisting of $(C_1-C_6)$-alkyl, $(C_3-C_7)$-cycloalkyl and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21;

R8 is selected from the series consisting of hydrogen and $(C_1-C_4)$-alkyl;

R20 is selected from the series consisting of R24, fluorine, HO—, $(C_1-C_6)$-alkyl-O—, $(C_3-C_7)$-cycloalkyl-O—, HO—S$(O)_2$—O—, $(HO)_2P(O)$—O—, $(C_1-C_6)$-alkyl-S$(O)_n$—, R31-N(R32)-, R33-C(O)—N(R32)-, $(C_1-C_6)$-alkyl-S$(O)_2$—N(R32)-, R31-N(R32)-C(O)— and R31-N(R32)-S$(O)_2$—;

R21 is selected from the series consisting of $(C_1-C_4)$-alkyl, HO—$(C_1-C_4)$-alkyl-, R31-N(R32)-$(C_1-C_4)$-alkyl-, fluorine, HO—, $(C_1-C_6)$-alkyl-O—, $(C_3-C_7)$-cycloalkyl-O—, HO—S$(O)_2$—O—, $(HO)_2P(O)$—O—, R31-N(R32)-, R33-C(O)—N(R32)- and R31-N(R32)-C(O)—;

R22 is selected from the series consisting of halogen, $(C_1-C_4)$-alkyl, HO—$(C_1-C_4)$-alkyl-, $(C_3-C_7)$-cycloalkyl, HO—, $(C_1-C_6)$-alkyl-O—, $(C_3-C_7)$-cycloalkyl-O—, HO—S$(O)_2$—O—, $(HO)_2P(O)$—O—, $(C_1-C_6)$-alkyl-S$(O)_n$—, R31-N(R32)-, R33-C(O)—N(R32)- and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R33 is selected from the series consisting of $(C_1-C_6)$-alkyl;

R31 and R32 are independently of one another selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are 1;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

As another such example, compounds of the formula I may be mentioned, wherein

Ar is phenyl which is unsubstituted or substituted by one or two identical or different substituents R0;

R0 is selected from the series consisting of halogen, $(C_1-C_6)$-alkyl and $(C_1-C_6)$-alkyl-O—;

R1 is hydrogen;

R2 is R5-N(R6)-C(O)—;

R3 is hydrogen;

R4 is hydrogen;

one of the groups R5 and R6 is selected from the series consisting of hydrogen and $(C_1-C_6)$-alkyl, and the other of the groups R5 and R6 is selected from the series consisting of $(C_1-C_6)$-alkyl, $(C_3-C_7)$-cycloalkyl and Het2, wherein $(C_1-C_6)$-alkyl all are unsubstituted or substituted by one or more identical or different substituents R20, and $(C_3-C_7)$-cycloalkyl and Het2 all are unsubstituted or substituted by one or more identical or different substituents R21;

R20 is selected from the series consisting of R24, fluorine, HO—, $(C_1-C_6)$-alkyl-O—, $(C_3-C_7)$-cycloalkyl-O—, HO—S$(O)_2$—O—, $(HO)_2P(O)$—O—, $(C_1-C_6)$-alkyl-S$(O)_n$—, R31-N(R32)-, R33-C(O)—N(R32)-, $(C_1-C_6)$-alkyl-S$(O)_2$—N(R32)- and R31-N(R32)-C(O)—;

R21 is selected from the series consisting of $(C_1-C_4)$-alkyl, HO—$(C_1-C_4)$-alkyl-, R31-N(R32)-$(C_1-C_4)$-alkyl-, fluorine, HO—, $(C_1-C_6)$-alkyl-O—, $(C_3-C_7)$-cycloalkyl-O—, HO—S$(O)_2$—O—, $(HO)_2P(O)$—O—, R31-N(R32)-, R33-C(O)—N(R32)- and R31-N(R32)-C(O)—;

R22 is selected from the series consisting of halogen, $(C_1-C_4)$-alkyl, HO—$(C_1-C_4)$-alkyl-, $(C_3-C_7)$-cycloalkyl, HO—, $(C_1-C_6)$-alkyl-O—, $(C_3-C_7)$-cycloalkyl-O—, HO—S$(O)_2$—O—, $(HO)_2P(O)$—O—, $(C_1-C_6)$-alkyl-S$(O)_n$—, R31-N(R32)-, R33-C(O)—N(R32)- and R31-N(R32)-C(O)—;

R24 is a 3-membered to 7-membered, monocyclic ring which is saturated, partially unsaturated or aromatic and comprises 0, 1 or 2 identical or different ring heteroatoms selected from the series consisting of nitrogen, oxygen and sulfur, and which is unsubstituted or substituted by one or more identical or different substituents R22;

R33 is selected from the series consisting of $(C_1-C_6)$-alkyl;

R31 and R32 are independently of one another selected from the series consisting of hydrogen and $(C_1-C_6)$-alkyl;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are 1;

wherein all cycloalkyl groups, independently of any other substituents which can be present on a cycloalkyl, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents;

in any of their stereoisomeric forms or a mixture of stereoisomeric forms in any ratio, and the pharmaceutically acceptable salt thereof.

A subject of the invention also is a compound of the formula I which is selected from any of the specific compounds of the formula I which are disclosed herein, or is any one of the specific compounds of the formula I which are disclosed herein, irrespective thereof whether they are disclosed as a free compound and/or as a specific salt, or a pharmaceutically acceptable salt thereof, wherein the compound of the formula I is a subject of the invention in any of its stereoisomeric forms or a mixture of stereoisomeric forms in any ratio as well as any specific salts and stereoisomeric forms disclosed herein. For example, a subject of the invention is a compound of the formula I which is selected from the series consisting of:

trans-4-(2-o-Tolyl-chroman-6-yloxy)-cyclohexylamine,
N-(Isoxazol-5-ylmethyl)-4-(2-o-tolyl-chroman-6-yloxy)-cyclohexanecarboxamide,
2-Amino-N-[trans-4-((S)-2-phenyl-chroman-6-yloxy)-cyclohexyl]-acetamide,
4-(2-o-Tolyl-chroman-6-yloxy)-N-(1,3,5-trimethylpyrazol-4-ylmethyl)-cyclohexylamine,
(S)—N-[trans-4-(2-Phenyl-chroman-6-yloxy)-cyclohexyl]-pyrrolidine-2-carboxamide,
trans-4-((R)-2-o-tolyl-chroman-6-yloxy)-cyclohexanecarboxylic acid (2-hydroxy-ethyl)-amide,
trans-4-((S)-2-o-tolyl-chroman-6-yloxy)-cyclohexanecarboxylic acid (2-hydroxy-ethyl)-amide,
cis-4-((R)-2-o-tolyl-chroman-6-yloxy)-cyclohexanecarboxylic acid (2-hydroxy-ethyl)-amide,
cis-4-((S)-2-o-tolyl-chroman-6-yloxy)-cyclohexanecarboxylic acid (2-hydroxy-ethyl)-amide, and
Phosphoric acid mono-(2-{[trans-4-((S)-2-o-tolyl-chroman-6-yloxy)-cyclohexanecarbonyl]-amino}-ethyl) ester disodium salt, or which is any one of these compounds, and its pharmaceutically acceptable salts, wherein the compound of the formula I is a subject of the invention in any of its stereoisomeric forms or a mixture of stereoisomeric forms in any ratio, unless a specific stereoisomeric form is specified with respect to any carbon atoms in the respective compound.

Another subject of the present invention are processes for the preparation of the compounds of the formula I which are outlined below and by which the compounds of the formula I and intermediates occurring in the course of their synthesis are obtainable. For example, one such process relates to the synthesis of compounds of the formula I from chroman-6-ols of the formula II and cycloalkanols of the formula III, and includes the formation of the ether linkage between the cycloalkane ring and the chroman ring to give compounds of the formula IV and, depending on the meaning of the groups X and Y in the compound of the formula III and the groups R2 and R3 in the final compound of the formula I, the subsequent conversion of the groups X and Y into the groups R2 and R3 and/or other conversions of groups.

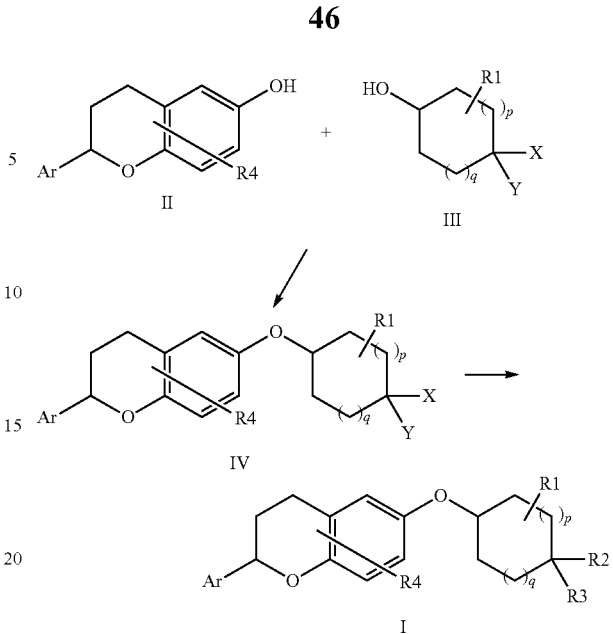

The groups Ar, R1 and R4 and the numbers p and q in the compounds of the formulae II, III and IV are defined as in the compounds of the formula I, and additionally can functional groups be present in protected form or in the form of a precursor group which is subsequently converted into the final group. One or both of the groups X and Y in the compounds of the formulae III and IV can be the groups R2 and R3 which are present in the final compound of the formula I, and thus in certain cases the compound of the formula IV already be the compound of the formula I, or one or both of the groups X and Y can be protected forms or precursor groups of the groups R2 and R3 or starting groups for the formation of the groups R2 and R3. For example, in case the groups R2 and R3 in the compound of the formula I do not interfere with the formation of the ether linkage, such as in case R2 is hydrogen, or alkyl which may be unsubstituted or substituted by indifferent substituents, or alkyl-O—, for example, and/or R3 is hydrogen, or alkyl which may be unsubstituted or substituted by indifferent substituents, the groups X and Y in the compound of the formula III may already have the meaning of the respective groups R2 and R3. For the synthesis of compounds of the formula I in which R2 is HO—, alkyl-O—, alkyl-C(O)—O—, phenyl-C(O)—O— or Het1-C(O)—O—, and R3 is hydrogen or alkyl, or R2 and R3 together are oxo, compounds of the formula III may be employed in which X is a protected hydroxy group and Y is hydrogen or alkyl, or X and Y together are a protected oxo group, and the obtained compounds of the formula IV deprotected and subjected to a variety of further reactions. Likewise, for the synthesis of compounds of the formula I in which R2 is R5-N(R6)-, R7-C(O)—N(R8)-, R7-S(O)$_2$—N(R8)- or R9-N(R10)-C(O)—N(R8)-, compounds of the formula III may be employed in which X is a protected amino group and Y is hydrogen or alkyl, and the obtained compounds of the formula IV deprotected and subjected to a variety of further reactions. For the synthesis of compounds of the formula I in which R2 is an amide group R5-N(R6)-C(O)—, compounds of the formula III may be employed in which X is an ester group such as alkyl-O—C(O)— and Y is hydrogen or alkyl, and the obtained compounds of the formula IV either directly or via the respective carboxylic acids converted in the amide compounds of the formula I. More details on such synthesis strategies are given below and in the examples. A wide range of suitable starting cycloalkanols of the formula III are commercially available or can be prepared according to, or analogously to, procedures described in the literature, as applies likewise to the other starting compounds employed in the syntheses of the compounds of the formula I.

The reaction of the compounds of the formulae II and III, i.e. the formation of the ether linkage, is conveniently performed by means of the well-known Mitsunobu reaction in the presence of a tertiary phosphine, such as a triarylphosphine like triphenylphosphine or a trialkylphosphine like tributylphosphine, and an azodicarboxylic acid derivative, such an azodicarboxylic acid diester like diethyl azodicarboxylate (DEAD) and diisopropyl azodicarboxylate (DIAD) or an azodicarboxylic acid diamide like azodicarboxylic acid dipiperidide (ADDP). The Mitsunobu reaction, which proceeds with inversion of the configuration at the carbon atom in the compound of the formula III which carries the hydroxy group depicted in formula III, is performed under anhydrous conditions in an inert solvent such as a hydrocarbon like benzene and toluene, a chlorinated hydrocarbon like dichloromethane or chloroform, an ether like diethyl ether, tetrahydrofuran (THF) or dioxane, a nitrile like acetonitrile, or an amide like dimethylformamide (DMF), generally at temperatures from about −50° C. to about 100° C., in particular from about 0° C. to about 30° C. More details are found in the various literature articles about the Mitsunobu reaction, such as the review articles by O. Mitsunobu, Synthesis (1981): 1-28; D. L. Hughes, Organic Reactions 42 (1992): 335-656; K. C. Kumara Swamy et al., Chemical Reviews 109 (2009): 2551-2651.

As an example of the syntheses of types of compounds of the formula I from compounds of the formulae II and III via the compounds of the formula IV mentioned above, in the following scheme the synthesis of the compounds of the formula Id is illustrated, i.e. compounds of the formula I in which R2 is R5-N(R6)-C(O)—.

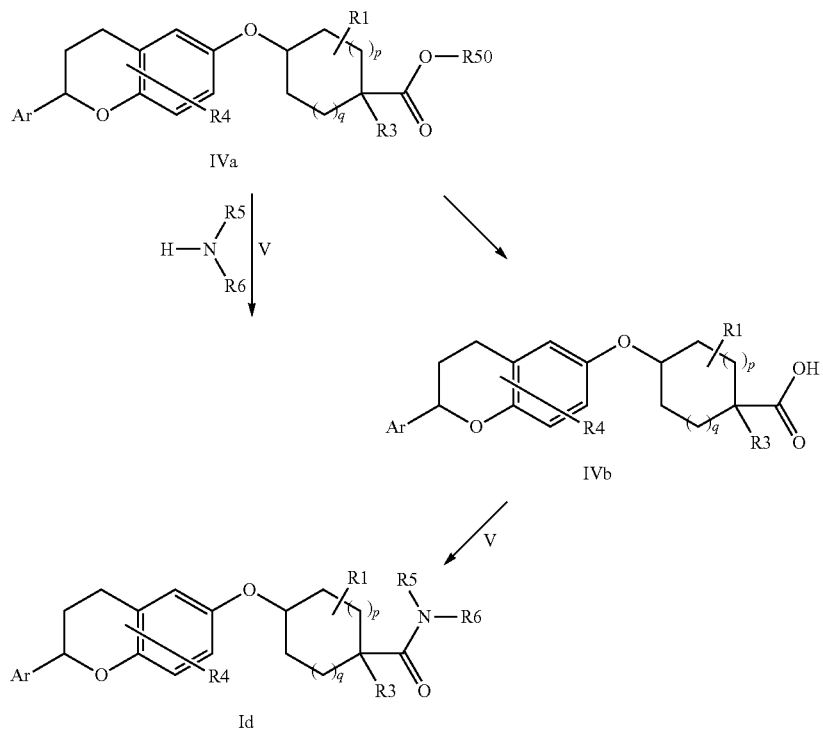

As mentioned above, compounds of the formula III in which X is an ester group, can be reacted with compounds of the formula II to give compounds of the formula IV, such as the compounds of the formula IVa in which R50 is $(C_1-C_4)$-alkyl, for example. The compounds of the formula IVa, in particular compounds of the formula IVa in which R50 is $(C_1-C_2)$-alkyl, can be reacted with amines of the formula V under standard conditions for the aminolysis of esters, for example in a solvent such as a hydrocarbon like toluene, a chlorinated hydrocarbon like dichloromethane, 1,2-dichloroethane or chlorobenzene or an ether like THF, dioxane or 1,2-dimethoxyethane (DME) at temperatures from about 20° C. to about 120° C., to give compounds of the formula Id. Compounds of the formula IVa can also be transformed into compounds of the formula Id in a convenient manner by first converting the compound of the formula IVa into the respective carboxylic acid of the formula IVb, or a salt thereof, and reacting the compound of the formula IVb or its salt with an amine of the formula V under standard conditions for the formation of amides from carboxylic acids. The groups Ar, R1, R3, R4, R5 and R6 and the numbers p and q in the compounds of the formulae IVa, IVb and V are defined as in the compounds of the formula I, and additionally can functional groups be present in protected form or in the form of a precursor group which is subsequently converted into the final group.

Compounds of the formula IVa can be converted into compounds of the formula IVb by treatment with an acid or base, for example by treatment with an alkali metal hydroxide such as lithium hydroxide, sodium hydroxide or potassium hydroxide in a solvent such as an ether like THF, dioxane or DME or an alcohol such as methanol or ethanol, or a mixture of solvents, in particular an aqueous solvent or mixture of solvents, or by treatment with hydrochloric acid or trifluoroacetic acid in a solvent such as a chlorinated hydrocarbon like dichloromethane, an ether or an alcohol, in particular in the case of a tert-butyl ester, at temperatures from about 20° C. to about 100° C., followed by standard work-up procedures such as an acidification in case the ester of the formula IVa is hydrolyzed in the presence of a base and a free carboxylic acid of the formula IVb is to be prepared, wherein the detailed conditions depend on the particulars of the specific case, as usual, and are readily chosen by a person skilled in the art. For the reaction with the compound of the formula V, the carboxylic acid group HO—C(O)— in the compound of the formula IVb is generally activated in situ by means of a customary amide coupling reagent or converted into a reactive carboxylic acid derivative which can be prepared in situ or isolated. For example, the compound of the formula IVb can be converted into an acid halide, e.g. by treatment with thionyl chloride, phosphorus pentachloride or oxalyl chloride, or treated with an alkyl chloroformate like ethyl chloroformate or isobutyl chloroformate to give a mixed anhydride. Customary coupling reagents which can be employed, are propanephosphonic anhydride, N,N'-carbonyldiazoles like N,N'-carbonyldiimidazole (CDI), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxybenzotriazole (HOBT) or 1-hydroxy-7-azabenzotriazole (HOAT), uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), and phosphonium-based coupling reagents like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP). The reaction of the activated compound of the formula IVb or a reactive derivative of the compound of the formula IVb is generally carried out in an inert solvent, for example a hydrocarbon like toluene, a chlorinated hydrocarbon like dichloromethane, an ether like THF, dioxane or DME, an ester like ethyl acetate or butyl acetate, a nitrile like acetonitrile, an amide like DMF or N-methylpyrrolidin-2-one (NMP), or water, or a mixture of solvents, at temperatures from about −10° C. to about 100° C., in particular at temperatures from about 0° C. to about 60° C. Favorably, the reaction is carried out in the presence of a base such as a tertiary amine, like triethylamine, ethyldiisopropylamine, N-methylmorpholine or pyridine, or an inorganic base such as an alkali metal hydroxide, carbonate or hydrogencarbonate, like sodium hydroxide, potassium hydroxide, sodium carbonate or sodium hydrogencarbonate.

As another example, in the following scheme the synthesis of compounds of the formula I in which R2 and R3 together are oxo, i.e. compounds of the formula Ip, and their use in the synthesis of further compounds of the formula I is illustrated.

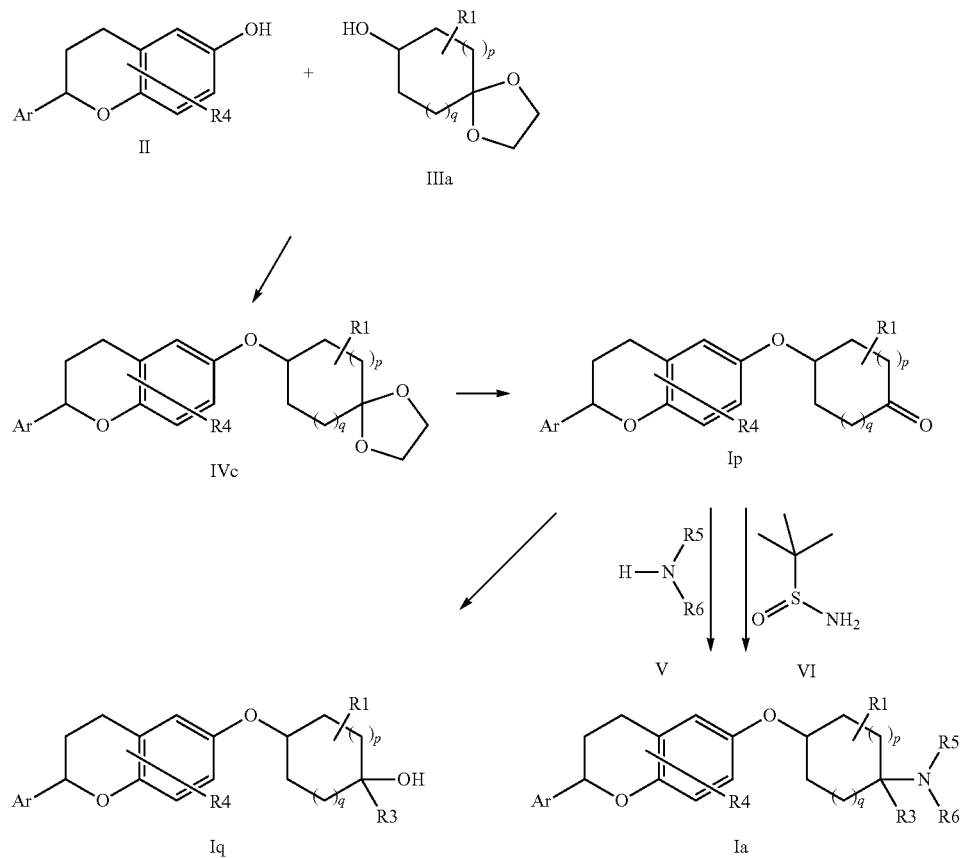

Compounds of the formula II can be reacted with compounds of the formula III in which the groups X and Y together are a divalent 1,2-ethylenedioxy group (—O—CH$_2$—CH$_2$—O—), i.e. 1,4-dioxaspirocycloalkanols of the formula IIIa, which are a protected form of the respective hydroxycycloalkanones in which the oxo group is ketalized with ethylene glycol. The obtained compounds of the formula IVc can be deprotected under standard conditions, for example by treatment with hydrochloric acid at temperatures from about 20° C. from about 30° C., to give the respective ketones, i.e. the compounds of the formula Ip, which already are final compounds of the formula I. The compounds of the formula Ip can readily be transformed into further compounds of the formula I under standard conditions. For example, they can be converted into compounds of the formula I in which R2 is HO—, i.e. compounds of the formula Iq, by reduction with a complex hydride reducing compounds of the formula Ip can be converted into compounds of the formula Ia in which R3 is an optionally substituted alkyl group and R5 and R6 are hydrogen, which compounds can be further modified at the nitrogen atom, for example alkylated in a reductive amination reaction, or acylated or sulfonylated, under standard conditions. The groups Ar, R1 and R4 and the numbers p and q in the compounds of the formulae IIIa and IVc are defined as in the compounds of the formula I, and additionally can functional groups be present in protected form or in the form of a precursor group which is subsequently converted into the final group.

As another example, in the following scheme the conversion of compounds of the formula IV in which the group X is a protected amino group and the group Y is the group R3, for example hydrogen, into compounds of the formula I is illustrated.

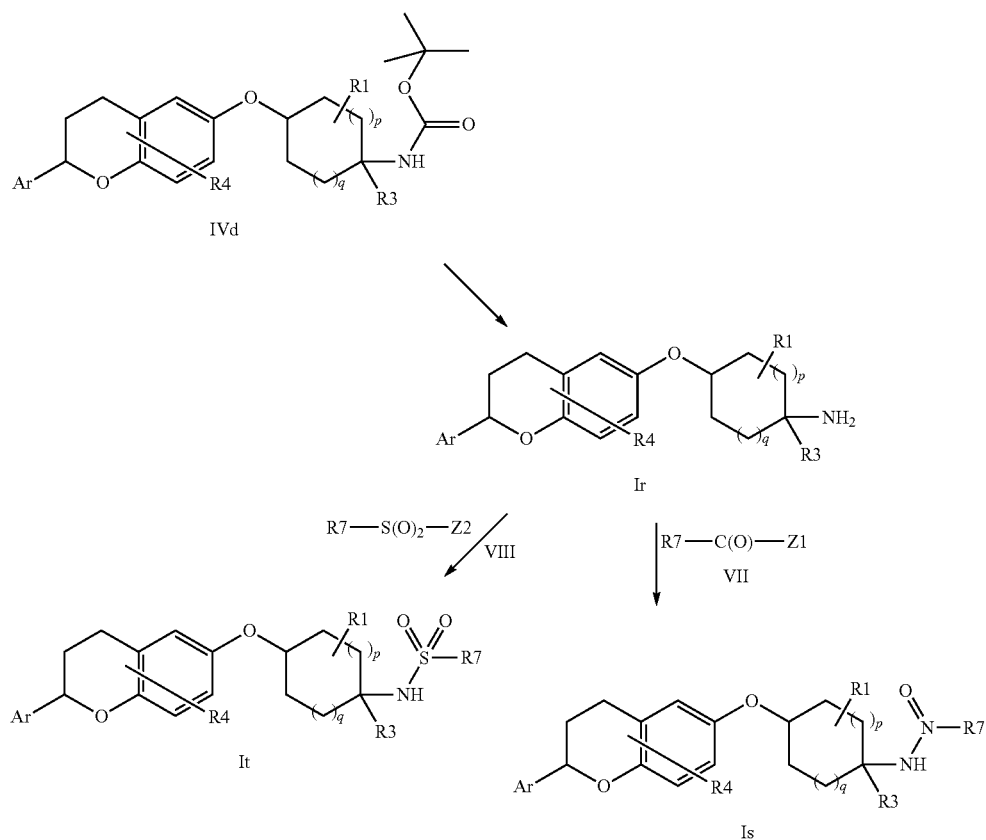

agent such as sodium borohydride to give compounds of the formula Iq in which R3 is hydrogen, or by treatment with a Grignard reagent to give compounds of the formula Iq in which R3 is an optionally substituted alkyl group. The compounds of the formula Ip can also be reacted with amines of the formula V, in particular amines in which at least one of the groups R5 and R6 is different from hydrogen, in a reductive amination reaction, for example with a complex borohydride as reducing agent such as sodium cyanoborohydride or sodium triacetoxyborohydride, to give compounds of the formula I in which R2 is the group R5-N(R6)-, i.e. compounds of the formula Ia, and R3 is hydrogen. By reaction with tert-butylsulfinamide of the formula VI and subsequently with a Grignard reagent the Compounds of the formula IVd, which can be obtained from compounds of the formula II and readily available aminocycloalkanols of the formula III which are protected at the nitrogen atom by a tert-butyloxy (Boc) group, can be deprotected by treatment with an acid, for example trifluoroacetic acid, at temperatures from about 20° C. to about 30° C. to give compounds of the formula Ir, which already are final compounds of the formula I. The compounds of the formula Ir can readily be transformed into further compounds of the formula I, for example acylated with compounds of the formula VII and sulfonylated with compounds of the formula VIII to give compounds of the formula I in which R2 is the group R7-C(O)—NH— and the group R7-S(O)$_2$—NH—, respectively, and R8 is hydrogen, i.e.

compounds of the formulae Is and It. The compounds of the formula Ir can also alkylated at the amino group, for example in a reductive amination reaction, to give corresponding compounds of the formula Ir in which the nitrogen atom carries one or two alkyl groups, and the latter compounds carrying one alkyl group acylated with compounds of the formula VII and sulfonylated with compounds of the formula VIII to give corresponding compounds of the formulae Is and It in which R8 is alkyl. The groups Ar, R1, R3, R4 and R7 and the numbers p and q in the compounds of the formulae IVd, VII and VIII are defined as in the compounds of the formula I, and additionally can functional groups be present in protected form or in the form of a precursor group which is subsequently converted into the final group. The groups Z1 and Z2 in the compounds of the formulae VII and VIII are nucleophilically substitutable leaving groups, in particular chlorine, in which latter case the compounds of the formulae VII and VIII are carboxylic acid chlorides and sulfonic acid chlorides. The groups Z1 and Z2 can also be a hydroxy group, in which case the compounds of the formulae VII and VIII are carboxylic acids and sulfonic acids which are generally activated in situ by means of a customary amide coupling reagent or converted into a reactive carboxylic acid derivative, such as the compound in which Z1 or Z2 is chlorine, for the reaction with the compound of the formula Ir. The explanations on activating agents and reaction conditions given above with respect to the reaction of the compounds of the formula IVb with the compounds of the formula V to give carboxamides apply correspondingly to the reaction of the compounds of the formulae VII and VIII with the compounds of the formula Ir to give carboxamides and sulfonamides.

For obtaining further compounds of the formula I, various transformations of functional groups can be carried out under standard conditions in compounds of the formula I obtained as described above, or in intermediates or starting compounds in the synthesis of the compounds of the formula I. For example, a hydroxy group can be reacted with a carboxylic acid or a reactive derivative thereof in a similar manner as described above for the reaction of a carboxylic acid with an amine, to give a carboxylic acid ester. Etherifications of hydroxy groups can be performed by alkylation with the respective halogen compound, for example a bromide or iodide, in the presence of a base such an alkali metal hydride like sodium hydride or an alkali metal carbonate like potassium carbonate or cesium carbonate in an inert solvent such as an amide like DMF or NMP or a ketone like acetone or butan-2-one, or with the respective alcohol under the conditions of the Mitsunobu reaction in the presence of a phosphine like triphenylphosphine or tributylphosphine and an azodicarboxylic acid derivative like diethyl azodicarboxylate or diisopropyl azodicarboxylate. By reaction with an isocyanate, a hydroxy group can be converted into an N-substituted carbamic acid ester. By treatment with a suitable halogenating agent, a hydroxy group can be converted into a halide. By treatment with sulfur trioxide in the presence of pyridine, a hydroxy group can be converted into the sulfuric acid mono ester. By treatment with a suitable phosphoramidite, such as dibenzyl N,N-diisopropyl-phosphoramidite, diallyl N,N-diisopropylphosphoramidite or di-tert-butyl N,N-diisopropyl-phosphoramidite of the formula (isopropyl)$_2$N—P(O—R55)$_2$, in which R55 is benzyl, allyl or tert-butyl, for example, in the presence of tetrazole and subsequent oxidation, for example with a peracid like 3-chloro-perbenzoic acid, a hydroxy group can be converted into its phosphoric acid ester dibenzyl ester, phosphoric acid ester diallyl ester and phosphoric acid ester di-tert-butyl ester, respectively, which can be cleaved to the phosphoric acid mono ester of the hydroxy group, i.e. the compound which contains the group $(HO)_2P(O)$— attached to the oxygen atom of the hydroxy group, by catalytic hydrogenation in the presence of a palladium catalyst in the case of the dibenzyl ester, by a palladium-catalyzed nucleophilic substitution in the case of the diallyl ester, and by treatment with an acid such as trifluoroacetic acid in the case of the di-tert-butyl ester. By treatment with chloromethyl chloroformate and subsequently with silver dibenzylphosphate, a hydroxy group can be converted into the carbonic acid ester dibenzyloxyphosphoryloxymethyl ester, which can be cleaved to the carbonic acid ester phosphonooxymethyl ester of the hydroxy group. i.e. the compound which contains the group $(HO)_2P(O)$—O—$CH_2$—O—C(O)— attached to the oxygen atom of the hydroxy group, by catalytic hydrogenation in the presence of a palladium catalyst (cf. WO 2010/039474). A halogen atom can be replaced with a variety of groups in a substitution reaction which may also be a transition-metal catalyzed reaction. An amino group can be modified under standard conditions for alkylation, for example by reaction with a halogen compound or by reductive amination of a carbonyl compound, or for acylation or sulfonylation, for example by reaction with an activated carboxylic acid or a carboxylic acid derivative like an acid chloride or anhydride. A carboxylic acid ester group can be hydrolyzed under acidic or basic conditions to give a carboxylic acid. A carboxylic acid group can be activated or converted into a reactive derivative as outlined above and reacted with an alcohol or an amine or ammonia to give an ester or amide. A primary amide can be dehydrated to give a nitrile. A sulfur atom in an alkyl-S— group or in a heterocyclic ring can be oxidized with a peroxide like hydrogen peroxide or a peracid to give a sulfoxide moiety (S(O)) or a sulfone moiety $(S(O)_2)$. A carboxylic acid group, carboxylic acid ester group and a ketone group can be reduced to an alcohol, for example with a complex hydride such al lithium aluminium hydride, lithium borohydride or sodium borohydride. A hydroxy group can be oxidized to an oxo group by means of pyridinium chlorochromate or the Dess-Martin periodinane reagent, for example. All such reactions in the preparation of the compounds of the formula I are known per se and can be carried out in a manner familiar to a person skilled in the art according to, or analogously, to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein.

The chroman-6-ols of the formula II which are employed in the synthesis of the compounds of the formula IV described above, can be obtained by various processes. In one of them, an acetophenone of the formula IX, which is substituted in the benzene ring by a hydroxy group and a group G1 and can additionally be substituted in the benzene ring and the acetyl group by substituents R4, is condensed with an aldehyde of the formula X in the presence of a base to give a chroman-4-one of the formula XII and/or a chalcone of the formula XI, and an obtained chalcone of the formula XI subsequently cyclized to the chroman-4-one of the formula XII.

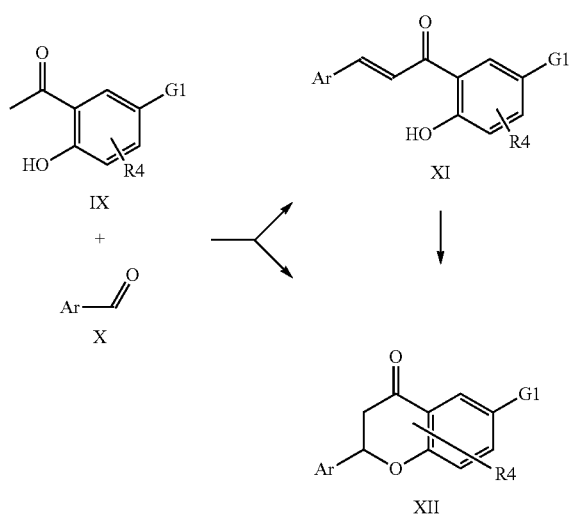

The groups Ar and R4 in the compounds of the formulae IX, X, XI and XII are defined as in the compounds of the formula I, and additionally can functional groups be present in protected form or in the form of a precursor group which is subsequently converted into the final group. The group G1 in the compounds of the formulae IX, XI and XII is a hydroxy group or bromine. When performing the reaction of the compounds of the formulae IX and X in the presence of an alkali metal hydroxide such as potassium hydroxide as the base in a solvent such as an alcohol like methanol or ethanol at temperatures from about 30° C. to about 70° C., the obtained product is the chalcone of the formula XI. When performing the reaction of the compounds of the formulae IX and X in the presence of a salt of a weak acid such as ammonium acetate, for example, in a solvent such as acetic acid at temperatures from about 100° C. to about 120° C., the obtained product is a mixture of the chalcone of the formula XI and chroman-4-one of the formula XII. The compound of the formula XI, as well as a mixture of the compounds of the formulae XI and XII, can be employed in the cyclization reaction to give the compound of the formula XII, which can be carried out by treating the starting material with an acid like hydrochloric acid or with an amine like ethyldiisopropylamine and potassium fluoride, in a solvent such as an alcohol like methanol or ethanol at temperatures from about 60° C. to about 100° C.

The oxo group in the ring position 4 of the compounds of the formula XII is then reduced to a $CH_2$ group to give the compounds of the formula XIV, favorably stepwise via the 4-hydroxy-chroman derivatives of the formula XIII.

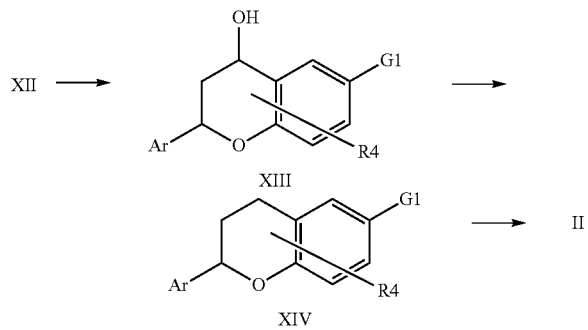

The groups Ar and R4 in the compounds of the formulae XIII and XIV are defined as in the compounds of the formula I, and additionally can functional groups be present in protected form or in the form of a precursor group which is subsequently converted into the final group. The group G1 in the compounds of the formulae XIII and XIV is a hydroxy group or bromine. The reduction of the compounds of the formula XII to the compounds of the formula XIII can be carried out under standard conditions for the reduction of a ketone to an alcohol, for example by means of a complex hydride as reducing agent, or a borane derivative, such as the borane-tetrahydrofuran complex in a solvent such as an ether like THF or dioxane, at temperatures from about 30° C. to about 80° C. The reduction of the compounds of the formula XIII to the compounds of the formula XIV can be performed, for example, by treatment with a silane reducing agent such as a trialkylsilane like triethylsilane and an acid such as trifluoroacetic acid in a solvent such as a chlorinated hydrocarbon like dichloromethane at temperatures from about 0° C. to about 40° C. In case the group G1 in the compound of the formula XIII and its precursor compounds is a hydroxy group, the obtained compound of the formula XIV already is a compound of the formula II. In case the group G1 in the obtained compound of the formula XIV is bromine, it can be converted into a hydroxy group by metalation of the compound of the formula XIV with a organolithium compound such as butyllithium and treatment with a trialkyl borate such as triisopropyl borate in a solvent such as a hydrocarbon like heptane or cyclohexane or an ether like THF or dioxane at temperatures from about −80° C. to about 0° C., followed by oxidative cleavage, for example by means of hydrogen peroxide in the presence of a base such as sodium hydroxide.

Further processes for the preparation of chroman-6-ols of the formula II involve a cyclization of a 3-hydroxypropyl-substituted benzene derivative of the formula XV, which is substituted in the benzene ring by two suitable groups G2 and G3 and can additionally be substituted in the benzene ring and the propyl group by substituents R4, to give a chroman derivative of the formula XVI, in which the group G3 is then converted into the hydroxy group present in the compounds of the formula II.

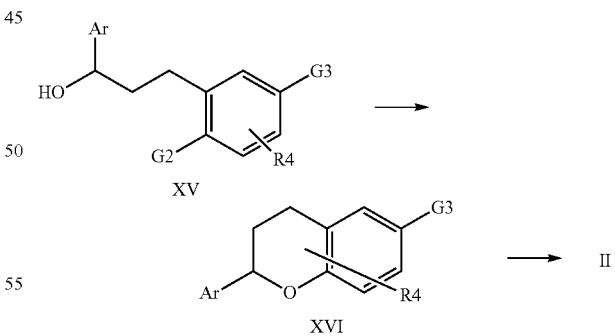

The groups Ar and R4 in the compounds of the formulae XV and XVI are defined as in the compounds of the formula I, and additionally can functional groups be present in protected form or in the form of a precursor group which is subsequently converted into the final group. The group G2 in the compounds of the formula XV can be a hydroxy group or a nucleophilically substitutable leaving group, for example fluorine. The group G3 in the compounds of the formulae XV and XVI can be bromine or $(C_1-C_4)$-alkyl-O— such as methoxy, for example. In case G3 is bromine, the conversion of the group G3 in the compound of the formula XVI into the hydroxy group in the compound of the formula II can be performed as described above for the conversion of the compounds of the formula XIV into the compounds of the formula II. In case G3 is ($C_1$-$C_4$)-alkyl-O—, the conversion into the hydroxy group can be performed according to standard procedures for ether cleavage, for example by treatment with boron tribromide in a chlorinated hydrocarbon such as dichloromethane at temperatures from about −20° C. to about 10° C. in the case of a methoxy group. In case the group G2 is a hydroxy group, the cyclization of the compound of the formula XV to the compound of the formula XVI can conveniently be performed under the conditions of the Mitsunobu reaction by treatment with a phosphine such as triphenylphosphine or tributylphosphine and an azodicarboxylic acid derivative such as diethyl azodicarboxylate or diisopropyl azodicarboxylate in a solvent such as an ether like THF or dioxane at temperatures from about 0° to about 30° C. In case the benzene ring carrying G2 in the compound of the formula XV is susceptible to a nucleophilic aromatic substitution and G2 is a leaving group such as fluorine, the cyclization can be performed by treatment of the compound of the formula XV with a base which enhances the nucleophilicity of the hydroxy group in position 3 of the propyl group, for example an alkali metal amide or an alkali metal hydride like sodium hydride, in an inert solvent such as an ether like THF or dioxane or an amide like DMF or NMP at temperatures from about −20° C. to about 100° C.

By cyclization of compounds of the formula XV also individual stereoisomeric forms of the compounds of the formula XVI and II, and finally of compounds of the formula I, can conveniently be prepared in which the chiral carbon atom in position 2 of the chroman ring is present either in R configuration or in S configuration. For the synthesis of such individual stereoisomers, which can otherwise be obtained, for example, by chromatographic resolution on a chiral phase of a mixture of the stereoisomers of the final compounds of the formula I or at any stage of the synthesis, the individual stereoisomeric forms of the 3-hydroxypropyl-substituted benzene of the formula XV are employed, i.e. the compounds of the formula XVa. Depending on the cyclization reaction and the conditions chosen, the cyclization can proceed with retention or inversion of the configuration of the chiral carbon atom to give the individual stereoisomeric forms of the compounds of the formula XVI, i.e. the compounds of the formula XVIa, which can be reacted further to the individual stereoisomeric forms compounds of the formulae II and I. In the compounds of the formulae XVa and XVIa are the groups Ar, R4, G2 and G3 defined as in the compounds of the formula XV and XVI, respectively, and the depicted chiral carbon atom is present, or is essentially present, either in R configuration or in S configuration, as is indicated by the wavy wedge.

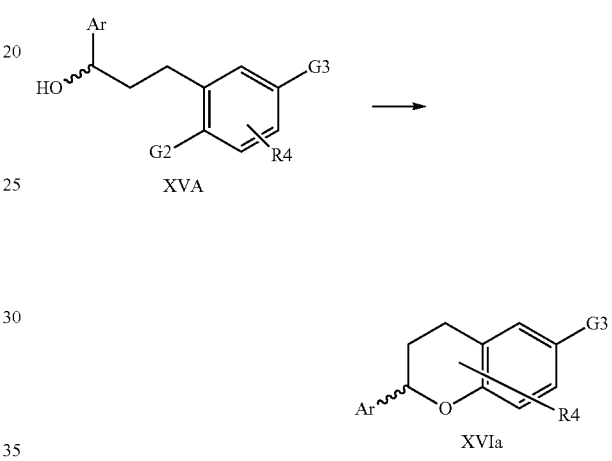

One embodiment of the present invention thus relates to a process for the preparation of a compound of the formula I,

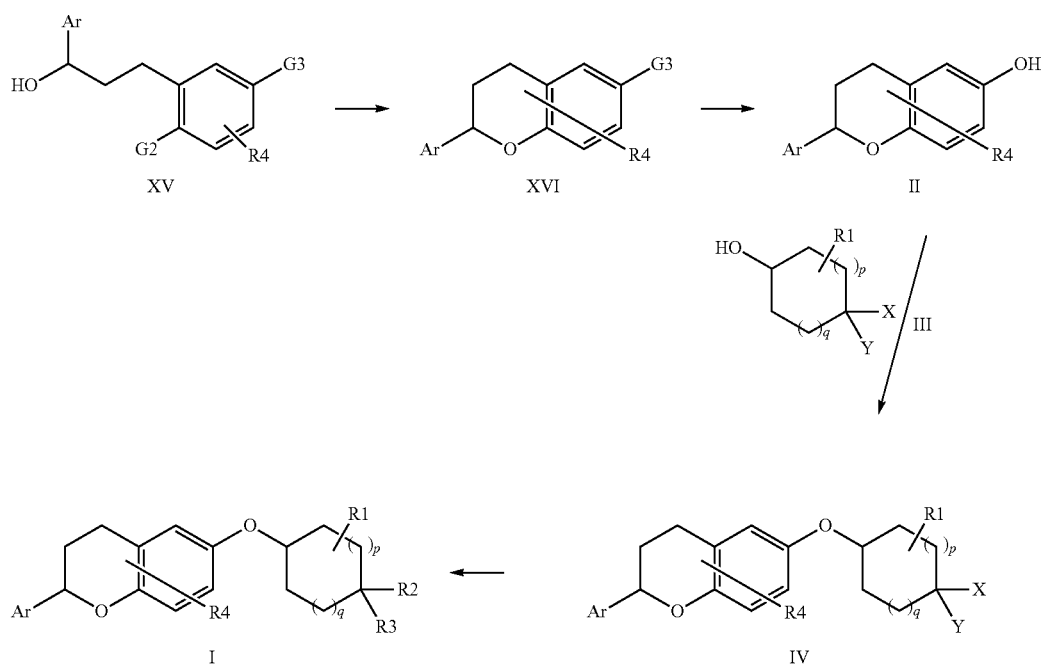

which comprises cyclizing a compound of the formula XV to a compound of the formula XVI, converting the compound of the formula XVI into a compound of the formula II, reacting the compound of the formula II with a compound of the formula III to give a compound of the formula IV, and converting the compound of the formula IV into a compound of the formula I.

Another embodiment of the present invention relates to the process described afore, in which the chiral carbon atom carrying the group Ar in the compounds of the formulae II, IV, XV and XVI is present, or is essentially present, in uniform configuration, either in R configuration or in S configuration, i.e. to a process for the preparation of a compound of the formula Ih, the formulae IIa and IVe are the groups Ar, R1, R4, X and Y and the numbers p and q defined as in the compounds of the formula II and IV, respectively.

The compounds of the formula XV, including the stereoisomeric forms of the formula XVa, which are employed in the cyclization reaction to the compounds of the formulae XVI and XVIa described above, can be obtained according

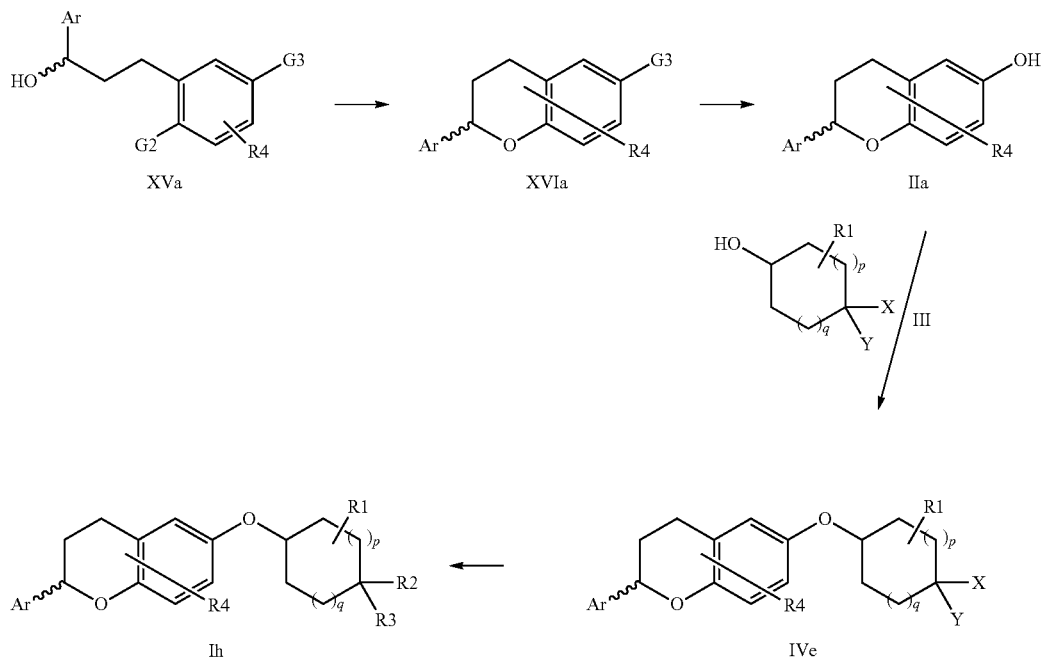

which comprises cyclizing a compound of the formula XVa to a compound of the formula XVIa, converting the compound of the formula XVIa into a compound of the formula IIa, reacting the compound of the formula IIa with a compound of the formula III to give a compound of the formula IVe, and converting the compound of the formula IVe into a compound of the formula Ih. In the compounds of to, or analogously to, various processes which are described in the literature. For example, a 3-oxo-propionic acid ester of the formula XVII can be alkylated with a benzyl halide of the formula XVIII to give a 3-oxo-propyl-substituted benzene derivative of the formula XIX, in which the ketone group is then reduced to the alcohol group to give a compound of the formula XV.

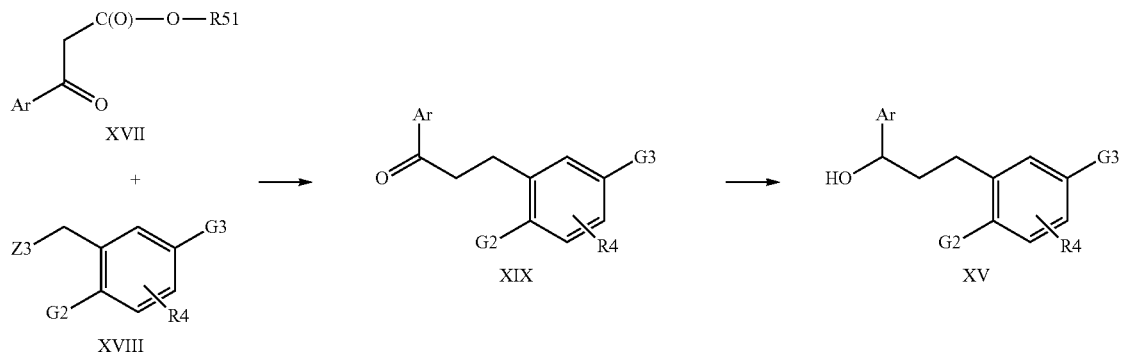

The groups Ar and R4 in the compounds of the formulae XVII, XVIII and XIX are defined as in the compounds of the formula I, and additionally can functional groups be present in protected form or in the form of a precursor group which is subsequently converted into the final group. In the preparation of compounds of the formula XV according to this process, the group G2 in the compounds of the formulae XVIII and XIX is in particular a nucleophilically substitutable leaving group, for example fluorine, and the group G3 in the compounds of the formulae XVIII and XIX in particular is bromine. The group R51 in the compounds of the formula XVII is $(C_1-C_4)$-alkyl, for example methyl or ethyl. The group Z3 in the compounds of the formula XVIII is a nucleophilically substitutable leaving group, for example chlorine or bromine. The reaction of the compounds of the formulae XVII and XVIII to give the compounds of the formula XIX is performed in an inert solvent such as an ether like THF, dioxane or DME in the presence of base such as an alkali metal alkoxide or an alkali metal hydride, for example sodium hydride, at temperatures from about 0° C. to about 50° C. By treatment of the obtained benzylated 3-oxo-propionic acid ester with an acid, for example hydrochloric acid in an aqueous solvent such as an ether like dioxane or an acid like acetic acid or a mixture of solvents at temperatures from about 60° C. to about 120° C. the ester moiety is then saponified and decarboxylated to give the ketone of the formula XIX. For the reduction of the ketone moiety in the compounds of the formula XIX to the compounds of the formula XV, various reducing agents can be employed, for example complex metal hydride such as sodium borohydride or lithium borohydride in a solvent such as an ether or an alcohol. In an asymmetric reduction reaction, by employing a chiral reducing agent, for example an enantiomeric form of a chiral complex metal hydride or a chiral borane, such as an alpha-pinene-based organoborane like B-chloro-diisopinocampheylborane, which is commonly abbreviated as $(-)$-$Ipc_2BCl$ or $(-)$-DipCl, and $(+)$-$Ipc_2BCl$ or $(+)$-DipCl, respectively, in an inert solvent such as an ether like THF or dioxane at temperatures from about $-40°$ C. to about 30° C., conveniently the individual stereoisomeric forms of the compounds of the formula XV can be obtained, i.e. compounds of the formula XVa, which can be cyclized to the enantiomeric forms of the compounds of the formula XVI, i.e. the compounds of the formula XVIa, as described above.

In another process for the preparation of compounds of the formula XV, an indan-1-one of the formula XX is subjected to a ring enlargement to give a chroman-2-one of the formula XXI, in which the lactone moiety can be reduced to an aldehyde moiety which is present in the form of the cyclic hemiacetal of the formula XXII and which can be reacted with a suitable organometal compound of the formula XXIII.

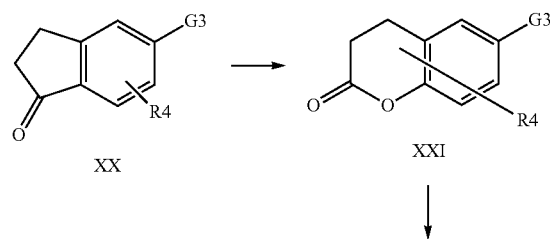

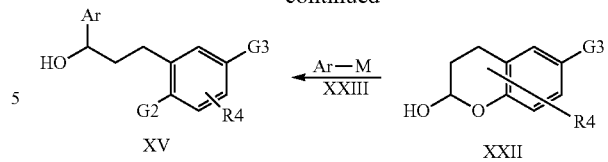

The groups Ar and R4 in the compounds of the formulae XX, XXI, XXII and XXIII are defined as in the compounds of the formula I, and additionally can functional groups be present in protected form or in the form of a precursor group which is subsequently converted into the final group. In the preparation of compounds of the formula XV according to this process, the group G3 in the compounds of the formulae XX, XXI and XXII is in particular a $(C_1-C_4)$-alkyl-O— group. The group M in the compounds of the formula XXIII is a metal or a metal equivalent, for example lithium. The conversion of the compound of the formula XX into the compound of the formula XXI can be performed by treatment with a peracid such as 3-chloro-perbenzoic acid in a solvent such as a chlorinated hydrocarbon like dichloromethane at temperatures from about $-10°$ C. to about 30° C. For the reduction of the lactone moiety in the compound of the formula XXI to the masked aldehyde moiety in the compound of the formula XXII, a complex metal reducing agent can be used, such as diisobutylaluminum hydride, in a solvent such as a hydrocarbon like cyclohexane or toluene or a chlorinated hydrocarbon like dichloromethane or an ether like THF or dioxane, or a mixture of solvents, at temperatures from about $-80°$ C. to about 30° C. For the subsequent step, the compound of the formula XXIII is generally prepared in situ from a suitable respective benzene or halogen-substituted benzene by metalation, for example with an organolithium compound like butyllithium or a lithium amide like lithium diisopropylamide or lithium 2,2,6,6-tetramethylpiperidide, and reacted with the compound of the formula XXII in an inert solvent such as a hydrocarbon like heptane or cyclohexane or an ether like THF or a mixture of solvents at temperatures from about $-80°$ C. to about 30° C.

As already indicated, it can be advantageous or necessary in all reactions which are carried out in the course of the preparation of the compounds of the formula I to temporarily protect functional groups or have them initially present in the form of precursor groups, and later deprotect them or convert them into the desired groups. Appropriate synthesis strategies and protective groups and precursor groups which are suitable for the respective case, are known to the person skilled in the art and can be found in P. G. M. Wuts and T. W. Greene, Greene's Protective Groups in Organic Synthesis, 4. ed. (2007), John Wiley & Sons, for example. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trifluoroacetic acid, acyl protective groups, for example ester and amides of hydroxy compounds and amino compounds, which can be cleaved again by acidic or basic hydrolysis, or alkoxycarbonyl protective groups, for example tert-butoxycarbonyl derivatives of amino compounds, which can be cleaved again by treatment with trifluoroacetic acid. Examples of precursors which may be mentioned are halogen atoms which can be replaced by many other groups, or nitro groups which can be converted, for example by catalytic hydrogenation, into amino groups which can be diazotized and converted into a large number of groups.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the final compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. Also for the characterization of the product, customary methods are used such as NMR, IR and mass spectroscopy.

Another subject of the present invention are the novel starting compounds and intermediates occurring in the synthesis of the compounds of the formula I, including the compounds of the formulae II, IIa, III, IIIa, IV, IVa, IVb, IVc, IVd, IVe, V, VI, VII, VIII, IX, X, XI, XII, XIII, XIV, XV, XVa, XVI, XVIa, XVII, XVIII, XIX, XX, XXI, XXII and XXIII, wherein the groups Ar, R1 to R7, R50, R51, G1, G2, G3, M, X, Y and Z1 to Z3 and the numbers p and q are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the sodium-calcium exchanger (NCX), especially the sodium-calcium exchanger of subtype 1 (NCX1), as can be demonstrated in the pharmacological tests described below and in other pharmacological tests which are known to a person skilled in the art, for example in animal models in which the effect on heart function can be determined ex vivo or in vivo. The compounds of the formula I and their pharmaceutically acceptable salts therefore are valuable pharmaceutical active compounds. The compounds of the formula I and their pharmaceutically acceptable salts can be used for the treatment of heart failure, including acute and chronic congestive heart failure (CHF), systolic heart failure, diastolic heart failure, heart failure with preserved ejection fraction, diabetic heart failure and decompensated heart failure and the management of heart failure in combination with a device, cardiac arrhythmias including atrial arrhythmias, atrial fibrillation, atrial fibrillation in CHF patients, ventricular arrhythmias, ventricular tachycardia, monomorphic ventricular tachycardia, polymorphic ventricular tachycardia, Torsade-de-pointes tachycardia and ventricular arrhythmias in CHF patients, stroke, dementia including Alzheimer's Disease, hypertension, cardiac ischemia, renal failure, shock including hemodynamic shock, cardiogenic shock and septic shock, age-related disorders, and diseases which are caused secondarily by an NCX-related damage, for example. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to cardiac arrhythmias or cardiac decompensation, by means of the prophylactic or preventive medicinal treatment the occurrence or re-occurrence of arrhythmias or decompensation can be prevented or their extent and sequelae decreased. The treatment of diseases can occur both in acute cases and in chronic cases. The compounds of the formula I and their pharmaceutically acceptable salts can further be used in various disorders in order to achieve an improvement of the perfusion of heart, brain and kidney, and in general in disorders in which intracellular calcium homeostasis is disturbed, or the NCX is activated in an undesired manner, or an inhibition of the NCX is intended by the physician for improving the patient's condition, wherein the compounds of the formula I and their pharmaceutically acceptable salts can also be employed in cases where only a certain partial inhibition of the NCX is intended, for example by use of a low dosage.

The compounds of the formula I and their pharmaceutically acceptable salts can therefore be used in animals, in particular in mammals and specifically in humans, as a pharmaceutical or medicament on their own, in mixtures with one another, or in the form of pharmaceutical compositions. A subject of the present invention also are the compounds of the formula I and their pharmaceutically acceptable salts for use as a pharmaceutical. A subject of the present invention also are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutical active compounds. A subject of the present invention also are the compounds of the formula I and their pharmaceutically acceptable salts for use as an anti-arrhythmic. A subject of the present invention also are the compounds of the formula I and their pharmaceutically acceptable salts for use in the treatment of the diseases mentioned above or below, including the treatment of any one of the mentioned diseases, for example heart failure, cardiac arrhythmias, stroke, dementia, hypertension, cardiac ischemia, renal failure, shock, age-related disorders or diseases which are caused secondarily by an NCX-related damage, wherein treatment of diseases comprises their therapy and prophylaxis as mentioned above, or for use as an inhibitor of the NCX. A subject of the present invention also are the use of the compounds of the formula I and their pharmaceutically acceptable salts for the manufacture of a medicament for the treatment of the diseases mentioned above or below, including the treatment of any one of the mentioned diseases, for example heart failure, cardiac arrhythmias, stroke, dementia, hypertension, cardiac ischemia, renal failure, shock, age-related disorders or diseases which are caused secondarily by an NCX-related damages, wherein treatment of diseases comprises their therapy and prophylaxis as mentioned above, or a medicament for inhibition of the NCX. A subject of the present invention also are methods for the treatment of the diseases mentioned above or below, including the treatment of any one of the mentioned diseases, for example heart failure, cardiac arrhythmias, stroke, dementia, hypertension, cardiac ischemia, renal failure, shock, age-related disorders or diseases which are caused secondarily by an NCX-related damage, wherein treatment of diseases comprises their therapy and prophylaxis as mentioned above, and a method for inhibiting the NCX, which comprise administering an efficacious amount of at least one compound of the formula I and/or a pharmaceutically acceptable salt thereof to a human or an animal which is in need thereof. The compounds of the formula I and their pharmaceutically acceptable salts, and pharmaceutical compositions and medicaments comprising them, can be administered enterally, for example by oral or rectal administration, parenterally, for example by intravenous, intramuscular or subcutaneous injection or infusion, or by another type of administration such as topical, percutaneous, transcutaneous, nasal, pharyngeal or inhalative administration, the preferred form of administration depending on the particulars of the specific case. The compounds of the formula I and their pharmaceutically acceptable salts can also be used in combination with other pharmaceutical active compounds.

The pharmaceutical compositions and medicaments according to the invention normally contain from about 0.5 to about 90 percent by weight of a compound or compounds of the formula I or pharmaceutically acceptable salts thereof, and an amount of active ingredient of the formula I and/or its pharmaceutically acceptable salt which in general is from about 0.1 mg to about 1 g, in particular from about 0.2 mg to about 500 mg, for example from about 1 mg to about 300 mg, per dose unit. Depending on the kind of the pharmaceutical composition and other particulars of the specific case, the amount may deviate from the indicated ones. The production of the pharmaceutical compositions and medicaments can be carried out in a manner known per se and familiar to the person skilled in the art. For this, the compounds of the formula I and/or their pharmaceutically acceptable salts are mixed together with one or more solid or liquid vehicles and/or excipients, if desired also in combination with one or more other pharmaceutical active compounds, and brought into a suitable form for dosage and administration, which can then be used in human medicine or veterinary medicine.

As vehicles, which may also be looked upon as diluents or solvents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, gel formers, thickeners, stabilizers, disintegrants, wetting agents, emulsifiers, dispersants, antifoaming agents, salts, buffer substances, colorants, flavorings and antioxidants may be mentioned. Examples of vehicles and excipients are water, physiological saline, vegetable oils such as sunflower oil, animal oils such as fish liver oil, waxes, alcohols such as ethanol, isopropanol, 1,2-propanediol, glycerol, polyols, polyethylene glycols, polyvinylpyrrolidone, gelatin, gum arabic, cellulose, carbohydrates such as glucose, lactose or starch like corn starch, magnesium carbonate, potassium phosphate, sodium chloride, stearic acid and its salts such as magnesium stearate, talc, lanolin, petroleum jelly, or mixtures thereof, for example mixtures of water or saline with one or more organic solvents such as mixtures of water with alcohols.

For oral and rectal use, pharmaceutical forms such as, for example, tablets, coated tablets, sugar-coated tablets, granules, hard and soft gelatin capsules, suppositories, solutions, including oily, alcoholic or aqueous solutions, or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Pharmaceutical formulations such as, for example, aerosols and sprays may comprise solutions, suspensions or emulsions of the active ingredient in a pharmaceutically acceptable solvent, such as ethanol or water, or a mixture of such solvents. The formulation may also comprise other pharmaceutical excipients such as surfactants, emulsifiers and stabilizers, and a propellant gas. Such a pharmaceutical form normally comprises the active ingredient in a concentration from about 0.1 to about 10%, in particular from about 0.3 to about 3% by weight.

As usual, the dosage of the compounds of the formula I and the frequency of administration depend on the circumstances of the specific case and is adjusted by the physician according to the customary rules and procedures. It depends, for example, on the compound of the formula I administered and its potency and duration of action, on the nature and severity of the individual syndrome, on the gender, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in vitro diagnoses of biological samples, if an inhibition of the NCX is intended. The compounds of the formula I and their salts can also be used as intermediates for the preparation of further pharmaceutical active substances.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the workup such as evaporation or lyophilization conditions. In the names of the example compounds and the structural formulae such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. $^1$H-NMR spectra were recorded at 500 MHz in $D_6$-DMSO as solvent at 298 K, unless specified otherwise. In the NMR characterization, the chemical shift δ (in ppm), the number of hydrogen atoms (H) and the multiplicity (s: singlet, d: doublet, dd: double doublet, t: triplet, m: multiplet; br: broad) of the peaks as determined on printouts are given. In the MS characterization, in general the mass number (m/z) of the peak of the molecular ion [M], e.g. [M$^+$], or of a related ion such as the ion [M+1], e.g. [(M+1)$^+$], i.e. the protonated molecular ion [(M+H)$^+$] ([MH$^+$]), or the ion [M−1], e.g. [(M−1)$^−$], i.e. the deprotonated molecular ion [(M−H)$^−$], which was formed depending on the ionization method used, is given. Generally, the ionization method was electrospray ionization (ESI$^+$). The UV wavelength for HPLC detection generally was 220 nm. The particulars of the LC/MS methods used are as follows. "ACN" means acetonitrile, "TFA" means trifluoroacetic acid, and "FA" means "formic acid.

Method A

Column: Waters UPLC BEH C18, 1.7 μm, 2.1×50 mm; temperature: 55° C.; flow rate: 0.9 ml/min; eluent A: water+ 0.1% FA; eluent B: ACN+0.08% FA; gradient: 95% A+5% B (0 min) to 5% A+95% B (1.1 min) to 5% A+95% B (1.7 min) to 95% A+5% B (1.8 min) to 95% A+5% B (2.0 min)

Method B

Column: Waters XBridge C18, 2.5 μm, 4.6×50 mm; temperature: 30° C.; flow rate: 1.3 ml/min; eluent A: water+ 0.1% FA; eluent B: ACN+0.1% FA; gradient: 97% A+3% B (0 min) to 40% A+60% B (3.5 min) to 2% A+98% B (4.0 min) to 2% A+98% B (5.0 min) to 97% A+3% B (6.5 min)

Method C

Column: Waters Atlantis T3 C18, 3 μm, 3×100 mm; temperature: 55° C.; flow rate: 1.0 ml/min; eluent A: water+ 0.05% TFA; eluent B: ACN+0.05% TFA; gradient: 95% A+5% B (0 min) to 5% A+95% B (5.0 min) to 95% A+5% B (7.0 min)

Method D

Column: Waters Atlantis T3 C18, 3 μm, 3×50 mm; temperature: 55° C.; flow rate: 0.6 ml/min; eluent A: water+ 0.05% TFA; eluent B: ACN+0.05% TFA; gradient: 95% A+5% B (0 min) to 5% A+95% B (4.0 min) to 2% A+98% B (6.5 min) to 95% A+5% B (9.0 min)

Method E

Waters UPLC BEH C18, 1.7 μm, 2.1×50 mm; temperature: 55° C.; flow rate: 0.9 ml/min; eluent A: water+0.05% FA; eluent B: ACN+0.035% FA; gradient: 95% A+5% B (0 min) to 5% A+95% B (1.1 min) to 5% A+95% B (1.7 min) to 95% A+5% B (1.8 min) to 95% A+5% B (2.0 min)

Method F

Waters UPLC BEH C18, 1.7 μm, 2.1×50 mm; temperature: 55° C.; flow rate: 0.9 ml/min; eluent A: water+0.05% FA; eluent B: ACN+0.035% FA; gradient: 95% A+5% B (0 min) to 5% A+95% B (1.1 min) to 5% A+95% B (1.7 min) to 95% A+5% B (1.9 min) to 95% A+5% B (2.0 min)

EXEMPLARY SYNTHESIS EXAMPLES

Example A (E)-1-(5-Bromo-2-hydroxy-phenyl)-3-o-tolyl-propenone and 6-bromo-2-o-tolyl-chroman-4-one

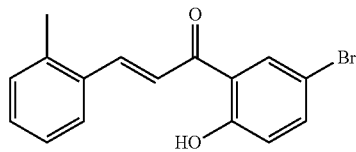

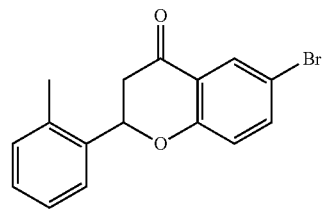

To a solution of o-tolylaldehyde (4.1 g, 33.7 mmol, 1.1 eq) and 5-bromo-2-hydroxy-acetophenone (6.9 g, 32.1 mmol) at room temperature in ethanol (100 ml) powdered potassium hydroxide (5.2 g, 93 mmol, 5 eq) was added and the suspension was stirred at 50° C. for 3 h while a red solution formed. The solution was allowed to reach room temperature and poured on ice. The aqueous mixture was adjusted to pH <7 using aqueous hydrochloric acid. The resulting yellow suspension was stirred till a yellow solid formed, and the precipitate filtered, washed with water and dried. The yellow (E)-1-(5-bromo-2-hydroxy-phenyl)-3-o-tolyl-propenone (9.6 g, 94%) was used in the cyclization reaction without further purification.

To a solution of (E)-1-(5-bromo-2-hydroxy-phenyl)-3-o-tolyl-propenone (9.6 g, 30.3 mmol) in ethanol (130 ml) concentrated aqueous hydrochloric acid was added (1.5 ml). The solution was heated to reflux for 5 h. Afterwards the solution was cooled to room temperature and the solvents was removed under reduced pressure. The resulting red 6-bromo-2-o-tolyl-chroman-4-one (9.5 g, 100%) was used in the next step without further purification.

According to the described procedure, also the following chromanones were synthesized:

6-Bromo-2-(5-fluoro-2-methyl-phenyl)-chroman-4-one

6-Bromo-2-(2,6-dimethyl-phenyl)chroman-4-one 2-(3-Fluoro-2-methoxy-phenyl)-6-hydroxy-chroman-4-one 6-Hydroxy-7-methyl-2-o-tolyl-chroman-4-one 2-(2-Fluoro-3-methoxy-phenyl)-6-hydroxy-chroman-4-one 6-Hydroxy-3-methyl-2-phenyl-chroman-4-one 2-(2-Fluoro-phenyl)-6-hydroxy-chroman-4-one 2-(3-Fluoro-2-methyl-phenyl)-6-hydroxy-chroman-4-one

Example B

6-Bromo-2-o-tolyl-chroman-4-ol and 6-bromo-2-o-tolyl-chroman

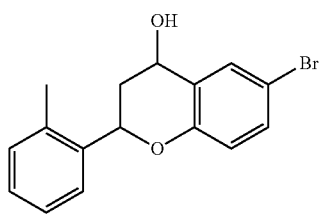

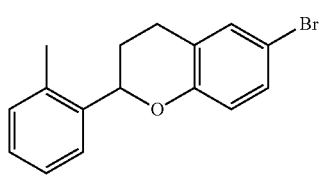

To a solution of 6-bromo-2-o-tolyl-chroman-4-one (11.0 g, 34.7 mmol) in tetrahydrofuran (100 ml) at room temperature a solution of borane tetrahydrofuran adduct (1M in tetrahydrofuran, 86.7 ml, 2.5 eq) was added dropwise. The solution was heated to reflux for 1 h, cooled to room temperature and added with caution to a mixture of ice water and 1N aqueous hydrochloric acid. The aqueous layer was extracted with dichloromethane, and the combined organic layers washed with water, dried with sodium sulfate and filtered and the solvent removed under reduced pressure. 6-Bromo-2-o-tolyl-chroman-4-ol was obtained as a yellow oil (11.1 g, 100%) and used in the reduction to the chroman without further purification.

To a solution of 6-bromo-2-o-tolyl-chroman-4-ol (11.9 g, 37.3 mmol) in dichloromethane (130 ml) at 0° C. triethylsilane (29.6 g, 255 mmol, 6.8 eq) and trifluoroacetic acid (75 ml, 27 eq) were added. The solution was stirred at room temperature for 2.5 h. The solvent was removed under reduced pressure and the residue separated between water and ethyl acetate. The aqueous layer was extracted with ethyl acetate and the combined organic layers washed with water and saturated aqueous solution of sodium hydrogencarbonate, dried with sodium sulfate and filtered, and the solvent removed under reduced pressure. The crude product was purified by column chromatography (silica gel; ethyl acetate/heptane gradient). 6-Bromo-2-o-tolyl-chroman was obtained as a pale yellow oil (7.10 g, 63%).

According to the described procedure, also the following chroman derivatives were synthesized:

7-Methyl-2-o-tolyl-chroman-6-ol

6-Bromo-2-(2,6-dimethyl-phenyl)chroman 2-(2-Fluoro-3-methoxy-phenyl)-chroman-6-ol 6-Bromo-2-(5-fluoro-2-methyl-phenyl)-chroman 2-(3-Fluoro-2-methoxy-phenyl)-chroman-6-ol 2-(2-Fluoro-phenyl)-chroman-6-ol 2-(3-Fluoro-2-methyl-phenyl)-chroman-6-ol 3-Methyl-2-phenyl-chroman-6-ol

Example C

(S)-6-Bromo-2-o-tolyl-chroman

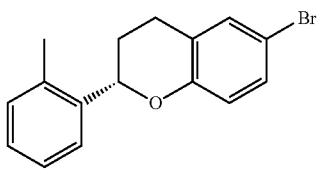 [SMILES: Cc1ccccc1[C@@H]1CCc2cc(Br)ccc2O1]

a) 3-(5-Bromo-2-fluoro-phenyl)-1-o-tolyl-propan-1-one

Sodium hydride (60% in oil, 2.1 g, 52 mmol) and methyl 3-oxo-3-o-tolylpropanoate (10 g, 52 mmol) were suspended in tetrahydrofuran and 4-bromo-2-(bromomethyl)-1-fluorobenzene (15.3 g, 57 mmol) was added. After complete conversion, the mixture was quenched with ice and a saturated solution of ammonium chloride and extracted with n-heptane. The combined organic layers were washed once with a saturated solution of ammonium chloride, water and brine. The organic layer was dried over magnesium sulfate and evaporated to dryness. The obtained yellow oil was dissolved in 25 ml of acetic acid, 25 ml of concentrated hydrochloric acid and 20 ml of 1,4-dioxane and heated under reflux for 4 h until LC/MS showed consumption of the starting material. 50 ml of water and 100 ml of tert-butyl methyl ether were added and the product was extracted. The combined organic layers were washed once with saturated solution of ammonium chloride, water and brine. The organic layer was dried over magnesium sulfate and evaporated to dryness. The residue was purified by column chromatography (silica gel, heptane/ethyl acetate gradient) to give 11.2 g of 3-(5-bromo-2-fluoro-phenyl)-1-o-tolyl-propan-1-one as a colorless oil.

b) (S)-3-(5-Bromo-2-fluoro-phenyl)-1-o-tolyl-propan-1-ol 1 3-(5-Bromo-2-fluoro-phenyl)-1-o-tolyl-propan-1-one (14 g, 43.6 mmol) was diluted with 20 ml of dry tetrahydrofuran and added dropwise to a solution of (−)-B-chlorodiisopinocampheyl-borane ((−)-DipCl, 27.96 g, 87.2 mmol) in 100 ml of dry tetrahydrofuran while maintaining the temperature between −30° C. and −25° C. After 6 h, LC/MS showed complete conversion of the starting material. The cold mixture was quenched with 10 ml of methanol and 10 g of sodium hydrogencarbonate and allowed to come to room temperature. The solvents were removed in vacuum and the obtained yellow oil was dissolved in 200 ml of ethyl acetate and a saturated solution of ammonium chloride. The phases were separated and the organic layer was washed once with 50 ml of brine, dried over magnesium sulfate and evaporates to give 45 g of a yellow oil. This oil was purified by column chromatography (silica gel, heptane/ethyl acetate gradient) to give 11.2 g of (S)-3-(5-bromo-2-fluoro-phenyl)-1-o-tolyl-propan-1-ol as a colorless oil.

Ratio of enantiomers (HPLC; column: Chiralcel OJ-H, 250×4.6 mm; eluent heptane/ethyl acetate/methanol 20:1:1): (S):(R)=99.4:0.6 c) (S)-6-Bromo-2-o-tolyl-chroman 3-(5-Bromo-2-fluoro-phenyl)-1-o-tolyl-propan-1-ol (10.5 g) was dissolved in 10 ml of dry N-methylpyrrolidin-2-one, and the solution was added dropwise to a suspension of sodium hydride (60% in oil, 1.56 g, 39 mmol) in 20 ml of dry N-methylpyrrolidin-2-one at 60° C. After complete addition the mixture was stirred at 60° C. to reach complete consumption of the starting material after 12 h. Then the mixture was quenched on ice and a saturated solution of ammonium chloride and extracted with n-heptane. The combined organic layers were washed once with a saturated solution of ammonium chloride, water and brine. The organic layer was dried over magnesium sulfate and evaporated to give 12 g of a clear oil. This oil was purified by column chromatography (silica gel, heptane/ethyl acetate gradient) to give 7.7 g of (S)-6-bromo-2-o-tolyl-chroman as a colorless oil.

Example D 2-o-Tolyl-chroman-6-ol

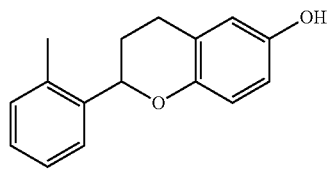 [SMILES: Cc1ccccc1C1CCc2cc(O)ccc2O1]

To a solution of 6-bromo-2-o-tolyl-chroman (1 g, 3.3 mmol) in tetrahydrofuran (3 ml) at −78° C. n-butyllithium (2.2 M in cyclohexane, 1.8 ml, 1.2 eq) was slowly added and the mixture kept at −78° C. for 30 min. Triisopropyl borate (1.9 g, 2.3 ml, 9.9 mmol, 3 eq) was added and stirring was continued at the same temperature for 1 h. The cold solution was poured in a solution of ethanol (1.1 ml), water (3.0 ml) and aqueous sodium hydroxide (8 M, 1.6 ml). To this solution hydrogen peroxide (aqueous 35%, 0.9 ml, 3.1 eq) was slowly added while the temperature was kept <30° C. Stirring at room temperature was continued for 15 min, the suspension was cooled to 0° C. and adjusted to pH <7 using aqueous hydrochloric acid. To the resulting solution a saturated aqueous solution of sodium sulfite (4 ml) was added and the aqueous layer extracted with ethyl acetate. The combined organic layers were dried with sodium sulfate and filtered, and the solvent removed under reduced pressure. The crude product was purified by column chromatography (silica gel; ethyl acetate/heptane gradient). 2-o-Tolyl-chroman-6-ol was obtained as a pale yellow solid (480 mg, 60%).

According to the described procedure, also the following chromanols were synthesized:
2-(5-Fluoro-2-methyl-phenyl)-chroman-6-ol
2-(2,6-Dimethyl-phenyl)-chroman-6-ol
(S)-2-o-Tolyl-chroman-6-ol Example E 5-Chloro-2-phenyl-chroman-6-ol

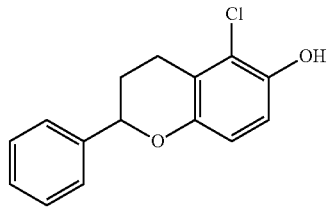 [SMILES: Oc1ccc2c(c1Cl)CCC(c1ccccc1)O2]

To a suspension of 200 mg of 2-phenyl-chroman-6-ol (0.88 mmol) and 142 mg of iron(III) chloride (0.88 mmol) in 15 ml of acetonitrile at room temperature 118 mg of N-chlorosuccinimide (0.88 mmol) were added in one portion and stirring was continued for 16 h. The volatile components were removed under reduced pressure. The resulting residue was purified by reversed phase HPLC. 127 mg of the title compound were obtained as a pale yellow solid (55%).

Example F

[4-trans-(2-o-Tolyl-chroman-6-yloxy)-cyclohexyl]-carbamic acid tert-butyl ester

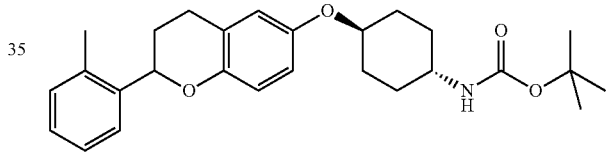

6.5 g (27 mmol) 2-o-tolyl-chroman-6-ol, 8.16 g (31.1 mmol) triphenylphosphine and 6.7 g (31.1 mmol) tert-butyl cis-4-hydroxycyclohexylcarbamate were dissolved in 50 ml dry tetrahydrofuran. 6.5 ml (31.1 mmol) diisopropyl azodicarboxylate were added to the solution and the reaction mixture was stirred at room temperature for 48 h. The solvent was removed by evaporation and the resulting oil was purified by chromatography over silica gel using heptane/ethyl acetate 4:1 as the eluent. The product fractions were collected and evaporated to yield 6 g of the title compound.

$^1$H-NMR (400 MHz): δ (ppm)=1.29-1.33 (4H, m), 1.38 (9H, s), 1.79 (2H, m), 1.82 (1H, m), 2.12 (1H, m), 2.35 (3H, s), 2.73 (1H, dd), 3.02 (1H, m), 3.28 (1H, m), 4.13 (1H, m), 5.17 (1H, dd), 6.69 (1H), 6.74 (1H), 6.79 (1H), 7.21 (3H), 7.43 (1H).

According to the described procedure, also the following compounds were synthesized:
6-(1,4-Dioxa-spiro[4.5]dec-8-yloxy)-2-o-tolyl-chroman
[cis-4-(2-o-Tolyl-chroman-6-yloxy)-cyclohexylmethyl]-carbamic acid tert-butyl ester
4-(2-o-Tolyl-chroman-6-yloxy)-cyclohexanecarboxylic acid ethyl ester
cis-4-(2-o-Tolyl-chroman-6-yloxy)-cyclohexanecarboxylic acid ethyl ester
trans-4-((S)-2-o-Tolyl-chroman-6-yloxy)-cyclohexanecarboxylic acid ethyl ester trans-4-(2-o-Tolyl-chroman-6-yloxy)-cyclohexanecarboxylic acid ethyl ester
[cis-4-(2-Phenyl-chroman-6-yloxy)-cyclohexyl]-carbamic acid tert-butyl ester
[trans-4-(2-Phenyl-chroman-6-yloxy)-cyclohexyl]-carbamic acid tert-butyl ester
[cis-4-(2-Phenyl-chroman-6-yloxy)-cyclohexylmethyl]-carbamic acid tert-butyl ester
{1-[1-Ethyl-4-(2-phenyl-chroman-6-yloxy)-cyclohexyl]-propyl}-carbamic acid tert-butyl ester
6-(1,4-Dioxa-spiro[4.5]dec-8-yloxy)-2-phenyl-chroman
cis-4-(2-Phenyl-chroman-6-yloxy)-cyclohexanecarboxylic acid ethyl ester
4-(2-Phenyl-chroman-6-yloxy)-cyclohexanecarboxylic acid ethyl ester
[4-(2-Phenyl-chroman-6-yloxy)-1-propyl-cyclohexyl]-carbamic acid tert-butyl ester
4-[2-(2,6-Dimethyl-phenyl)-chroman-6-yloxy]-cyclohexanecarboxylic acid ethyl ester
{trans-4-[2-(2,6-Dimethyl-phenyl)-chroman-6-yloxy]-cyclohexyl}-carbamic acid tert-butyl ester
2-(2,6-Dimethyl-phenyl)-6-(1,4-dioxa-spiro[4.5]dec-8-yloxy)-chroman
4-[2-(3-Fluoro-2-methyl-phenyl)-chroman-6-yloxy]-cyclohexanecarboxylic acid ethyl ester
6-(1,4-Dioxa-spiro[4.5]dec-8-yloxy)-2-(3-fluoro-2-methyl-phenyl)-chroman
6-(1,4-Dioxa-spiro[4.5]dec-8-yloxy)-2-(2-fluoro-phenyl)chroman
4-[2-(2-Fluoro-phenyl)-chroman-6-yloxy]-cyclohexanecarboxylic acid ethyl ester
{trans-4-[2-(5-Fluoro-2-methyl-phenyl)-chroman-6-yloxy]-cyclohexyl}-carbamic acid tert-butyl ester
{trans-4-[2-(2-Fluoro-phenyl)-chroman-6-yloxy]-cyclohexyl}-carbamic acid tert-butyl ester
4-(7-Methyl-2-o-tolyl-chroman-6-yloxy)-cyclohexanecarboxylic acid ethyl ester
4-(5-Chloro-2-phenyl-chroman-6-yloxy)-cyclohexanecarboxylic acid ethyl ester
4-[2-(2-Fluoro-3-methoxy-phenyl)-chroman-6-yloxy]-cyclohexanecarboxylic acid ethyl ester
4-(3-Methyl-2-phenyl-chroman-6-yloxy)-cyclohexanecarboxylic acid ethyl ester
4-[2-(3-Fluoro-2-methoxy-phenyl)-chroman-6-yloxy]-cyclohexanecarboxylic acid ethyl ester Example G trans-4-(2-o-Tolyl-chroman-6-yloxy)-cyclohexylamine hydrochloride

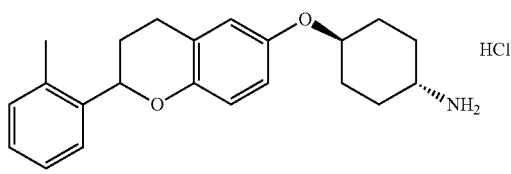 [SMILES: Cc1ccccc1C1CCc2cc(O[C@H]3CC[C@H](N)CC3)ccc2O1 ; Cl]

6 g (13.7 mmol) of [trans-4-(2-o-tolyl-chroman-6-yloxy)-cyclohexyl]-carbamic acid tert-butyl ester were dissolved in 50 ml of 1,4-dioxane and 25 ml of 2N hydrogen chloride in diethyl ether. The diethyl ether was removed by evaporation and the remaining solution was refluxed until no starting material could be detected by RP-HPLC. The resulting suspension was cooled to 0° C. and the crystals were collected by filtration, washed once with cold methyl tert-butyl ether and dried in vacuum at 25° C. to yield 3.6 g of the title compound.

$^1$H-NMR (400 MHz): δ (ppm)=1.42 (4H, m), 1.88 (1H, m), 1.95 (2H, m), 2.08 (3H, m), 2.35 (3H, s), 2.73 (1H, dd), 3.02 (2H, m), 4.13 (1H, m), 5.17 (1H, dd), 6.74 (2H), 6.79 (1H), 7.21 (3H), 7.43 (1H), 8.08 (3H, s).

According to the described procedure, also the following compounds were synthesized:
cis-4-(2-Phenyl-chroman-6-yloxy)-cyclohexylamine
trans-4-(2-Phenyl-chroman-6-yloxy)-cyclohexylamine
[cis-4-(2-Phenyl-chroman-6-yloxy)-cyclohexylmethyl]amine
4-(2-Phenyl-chroman-6-yloxy)-1-propyl-cyclohexylamine
1-[1-Ethyl-4-(2-phenyl-chroman-6-yloxy)-cyclohexyl]-propylamine
[cis-4-(2-o-Tolyl-chroman-6-yloxy)-cyclohexylmethyl]amine
trans-4-[2-(2,6-Dimethyl-phenyl)-chroman-6-yloxy]-cyclohexylamine
trans-4-[2-(2-Fluoro-phenyl)chroman-6-yloxy]-cyclohexylamine
trans-4-[2-(5-Fluoro-2-methyl-phenyl)-chroman-6-yloxy]-cyclohexylamine Example H trans-4-((S)-2-o-Tolyl-chroman-6-yloxy)-cyclohexanecarboxylic acid

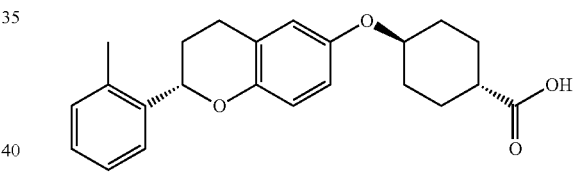

0.75 g (1.9 mmol) of trans-4-((S)-2-o-tolyl-chroman-6-yloxy)-cyclohexanecarboxylic acid ethyl ester was dissolved in 10 ml of tetrahydrofuran. 94 mg (3.9 mmol) lithium hydroxide (dissolved in 2 ml of water) were added. The solution was stirred at room temperature overnight until no starting material could be detected by RP-HPLC. The solution was diluted with methyl tert-butyl ether, and 2N hydrochloric acid was added until a pH of 2. After phase separation, the organic layer was dried over magnesium sulfate and the solvent was evaporated. The resulting product crystallized on standing to yield 0.65 g of the title compound.

$^1$H-NMR (400 MHz): δ (ppm)=1.36 (2H, m), 1.48 (2H, m), 1.85-2.11 (6H, m), 2.35 (3H, s), 2.38 (1H, m), 2.73 (1H, dd), 3.02 (1H, m), 4.18 (1H, m), 5.17 (1H, dd), 6.72 (3H), 7.21 (3H), 7.43 (1H), 12.10 (1H, s).

According to the described procedure, also the following compounds were synthesized:
cis-4-(2-Phenyl-chroman-6-yloxy)-cyclohexanecarboxylic acid
4-(2-Phenyl-chroman-6-yloxy)-cyclohexanecarboxylic acid
4-(7-Methyl-2-o-tolyl-chroman-6-yloxy)-cyclohexanecarboxylic acid
4-(5-Chloro-2-phenyl-chroman-6-yloxy)-cyclohexanecarboxylic acid 4-[2-(2-Fluoro-3-methoxy-phenyl)-chroman-6-yloxy]-cyclohexanecarboxylic acid
4-(3-Methyl-2-phenyl-chroman-6-yloxy)-cyclohexanecarboxylic acid
4-[2-(3-Fluoro-2-methoxy-phenyl)-chroman-6-yloxy]-cyclohexanecarboxylic acid
4-(2-o-Tolyl-chroman-6-yloxy)-cyclohexanecarboxylic acid
trans-4-(2-o-Tolyl-chroman-6-yloxy)-cyclohexanecarboxylic acid
cis-4-(2-o-Tolyl-chroman-6-yloxy)-cyclohexanecarboxylic acid
4-[2-(2,6-Dimethyl-phenyl)-chroman-6-yloxy]-cyclohexanecarboxylic acid
4-[2-(3-Fluoro-2-methyl-phenyl)-chroman-6-yloxy]-cyclohexanecarboxylic acid
4-[2-(2-Fluoro-phenyl)-chroman-6-yloxy]-cyclohexanecarboxylic acid Example J 4-(2-Phenyl-chroman-6-yloxy)-cyclohexanone

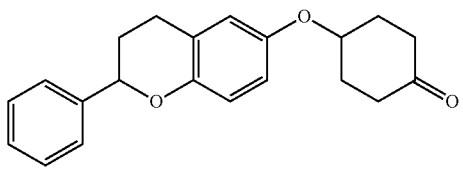 [SMILES: O=C1CCC(Oc2ccc3c(c2)CCC(c2ccccc2)O3)CC1]

430 mg of 6-(1,4-dioxa-spiro[4.5]dec-8-yloxy)-2-phenyl-chroman were dissolved at room temperature in 5 ml of tetrahydrofuran. 5 ml of 10% aqueous hydrochloric acid were added and stirring at room temperature was continued for 16 h. The reaction mixture was diluted with ethyl acetate and the organic layer washed with saturated aqueous solution of sodium hydrogencarbonate. The organic layer was dried with sodium sulfate and filtered, and the volatile components removed under reduced pressure. 357 mg of the title compound were obtained as a pale yellow solid.

According to the described procedure, also the following compounds were synthesized:
4-(2-o-Tolyl-chroman-6-yloxy)-cyclohexanone
4-[2-(2,6-Dimethyl-phenyl)-chroman-6-yloxy]-cyclohexanone
4-[2-(3-Fluoro-2-methyl-phenyl)-chroman-6-yloxy]-cyclohexanone
4-[2-(2-Fluoro-phenyl)-chroman-6-yloxy]-cyclohexanone Example K

[4-(2-o-Tolyl-chroman-6-yloxy)-cyclohexyl]-(1,3,5-trimethyl-1H-pyrazol-4-ylmethyl)-amine

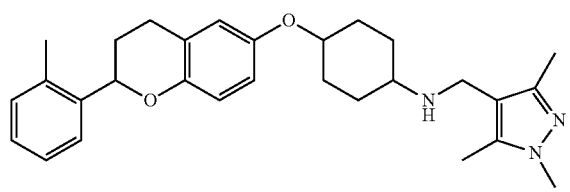 [SMILES: Cc1ccccc1C1CCc2cc(OC3CCC(NCc4c(C)nn(C)c4C)CC3)ccc2O1]

To a solution of 100 mg 4-(2-o-tolyl-chroman-6-yloxy)-cyclohexanone (0.30 mmol) in 2 ml of methanol and 0.15 ml of acetic acid at room temperature 124 mg (1,3,5-trimethyl-1H-pyrazol-4-yl-methyl)amine (0.89 mmol) and 56 mg of sodium cyanoborohydride (0.89 mmol) were added in one portion and stirring at room temperature was continued for 2 h. Volatile components were removed under reduced pressure and the resulting residue dissolved in dichloromethane. The organic layer was washed with aqueous 2N sodium hydroxide solution and saturated aqueous sodium chloride solution. The organic layer was dried with sodium sulfate and filtered, and the solvent removed under reduced pressure. The crude product was purified by reversed phase HPLC. 132 mg of the title compound were isolated.

Example L (Tetrahydrofuran-3-ylmethyl)-[trans-4-(2-o-tolyl-chroman-6-yloxy)-cyclohexyl]-amine and bis-(tetrahydrofuran-3-ylmethyl)-[trans-4-(2-o-tolyl-chroman-6-yloxy)-cyclohexyl]-amine

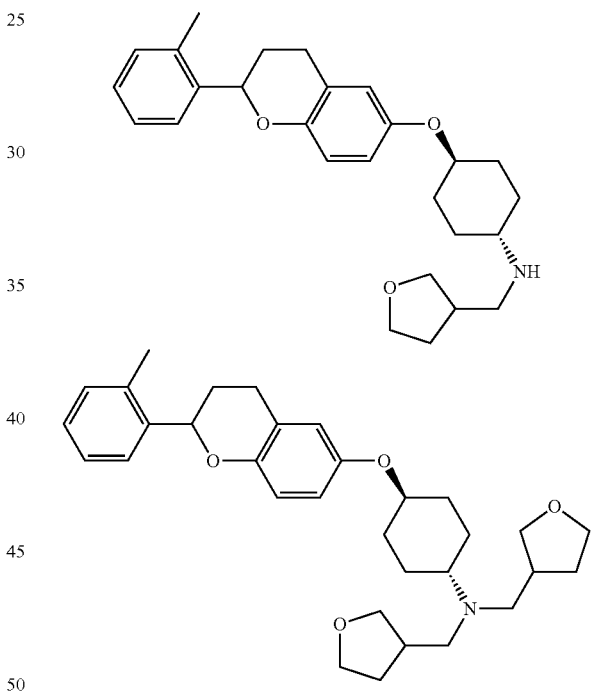

To a solution of 61 mg trans-4-(2-o-tolyl-chroman-6-yloxy)-cyclohexylamine (0.18 mmol) in 3 ml methanol and 0.2 ml of acetic acid at room temperature 39 mg tetrahydrofuran-3-carboxaldehyde (0.20 mmol) in 3 ml of methanol were added, and 12 mg of sodium cyanoborohydride (0.89 mmol (0.20 mmol) were then added in one portion. Stirring at room temperature was continued for 16 h. The solution was diluted with aqueous saturated sodium hydrogencarbonate solution and the aqueous layer extracted with dichloromethane. The combined organic layers were dried with sodium sulfate and filtered, and the solvent removed under reduced pressure. The crude product was purified by RP-HPLC. 23 mg of (tetrahydrofuran-3-ylmethyl)-[trans-4-(2-o-tolyl-chroman-6-yloxy)-cyclohexyl]-amine and 19 mg of bis-(tetrahydrofuran-3-ylmethyl)-[trans-4-(2-o-tolyl-chroman-6-yloxy)-cyclohexyl]-amine were isolated.

Example M ({[cis-4-(2-o-Tolyl-chroman-6-yloxy)-cyclohexylmethyl]-carbamoyl}-methyl)-carbamic acid tert-butyl ester

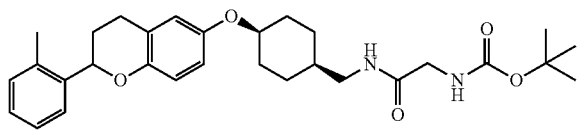 [SMILES: Cc1ccccc1C1CCc2cc(O[C@H]3CC[C@@H](CNC(=O)CNC(=O)OC(C)(C)C)CC3)ccc2O1]

To a suspension of 110 mg of [cis-4-(2-o-tolyl-chroman-6-yloxy)-cyclohexylmethyl]amine hydrochloride (0.28 mmol), 75 mg of N-tert-butoxycarbonylglycine (0.43 mmol), 76 mg of 1-(3-dimethylaminopropyl)-3-ethylcarbodiimide hydrochloride (0.40 mmol) and 54 mg of hydroxybenzotriazole (0.40 mmol) at room temperature in 2 ml of dimethylformamide 0.16 ml of N-methylmorpholine (1.42 mmol) were added and stirring at room temperature was continued for 16 h. The reaction mixture was diluted with water and extracted with ethyl acetate. The combined organic layers were washed with diluted aqueous sodium carbonate solution, dried with sodium sulfate and filtered, and the solvent removed under reduced pressure. The crude product was purified by column chromatography using ethyl acetate/heptane/methanol 5:10:1 as eluent. 95 mg of the title compound were isolated.

Example N

N-[cis-4-(2-Phenyl-chroman-6-yloxy)-cyclohexylmethyl]-methanesulfonamide

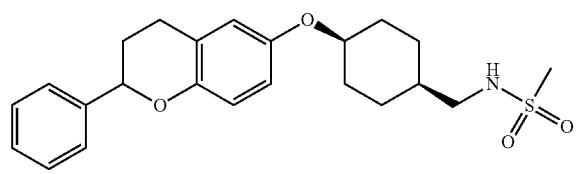 [SMILES: CS(=O)(=O)NC[C@H]1CC[C@@H](Oc2ccc3c(c2)CCC(c2ccccc2)O3)CC1]

To a solution of 150 mg [cis-4-(2-phenyl-chroman-6-yloxy)-cyclohexylmethyl]amine hydrochloride (0.40 mmol) at room temperature in 4 ml of pyridine 47 µl of methanesulfonyl chloride (0.60 mmol) were added and stirring at room temperature was continued for 16 h. The reaction mixture was diluted with water and extracted with dichloromethane The combined organic layers were washed with diluted aqueous hydrochloric acid, dried with sodium sulfate and filtered, and the solvent removed under reduced pressure. The crude product was purified by reversed phase HPLC. 97 mg of the title compound were isolated as a white solid.

Example O 4-(2-o-Tolyl-chroman-6-yloxy)-cyclohexanecarboxylic acid (2-hydroxy-ethyl)-amide

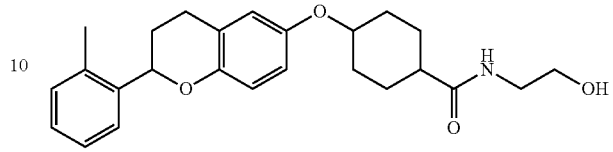

To a solution of 100 mg of 4-(2-o-tolyl-chroman-6-yloxy)-cyclohexanecarboxylic acid (0.40 mmol) at room temperature in 25 ml of dichloromethane 103 mg of 1-(3-dimethylaminopropyl)-3-ethylcarbodiimide hydrochloride (0.54 mmol), 73 mg of hydroxybenzotriazole (0.54 mmol), 0.12 ml of triethylamine (0.88 mmol) and 11 µl of 2-aminoethanol (0.19 mmol) were added, and stirring at room temperature was continued for 16 h. The reaction mixture was diluted with water and extracted with dichloromethane. The combined organic layers were dried with sodium sulfate and filtered, and the solvent removed under reduced pressure. The crude product was purified by reversed phase HPLC. 42 mg of a white solid were isolated which was a mixture of four stereoisomers of the title compound.

The stereoisomers were separated by preparative HPLC on a chiral phase (column: Chiralpak AS-H, 250×30 mm; temperature: 30° C.; flow rate: 40 ml/min; eluent: heptane/ethanol/methanol 20:1:1) to give trans-4-((R)-2-o-tolyl-chroman-6-yloxy)-cyclohexanecarboxylic acid (2-hydroxy-ethyl)-amide, trans-4-((S)-2-o-tolyl-chroman-6-yloxy)-cyclohexanecarboxylic acid (2-hydroxy-ethyl)-amide, stereoisomer 1 of cis-4-(2-o-tolyl-chroman-6-yloxy)-cyclohexanecarboxylic acid (2-hydroxy-ethyl)-amide, and stereoisomer 2 of cis-4-(2-o-tolyl-chroman-6-yloxy)-cyclohexanecarboxylic acid (2-hydroxy-ethyl)-amide. The configuration at the chiral carbon atom in position 2 of the chroman ring of stereoisomers 1 and 2 of cis-4-(2-o-tolyl-chroman-6-yloxy)-cyclohexanecarboxylic acid (2-hydroxy-ethyl)-amide is not known; one of them is cis-4-((R)-2-o-tolyl-chroman-6-yloxy)-cyclohexanecarboxylic acid (2-hydroxy-ethyl)-amide and the other is cis-4-((S)-2-o-tolyl-chroman-6-yloxy)-cyclohexanecarboxylic acid (2-hydroxy-ethyl)-amide.

Example P 4-(2-Phenyl-chroman-6-yloxy)-1-propyl-cyclohexanol

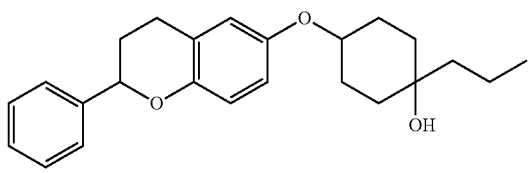 [SMILES: CCCC1(O)CCC(Oc2ccc3c(c2)CCC(c2ccccc2)O3)CC1]

100 mg of 4-(2-phenyl-chroman-6-yloxy)-cyclohexanone were dissolved at room temperature in 5 ml of tetrahydrofuran. A 2M solution of propylmagnesium chloride in diethyl ether (0.31 ml, 2 eq) was added, and stirring at room temperature was continued for 4 h. The reaction was stopped by careful addition of saturated aqueous ammonium chloride solution. The aqueous layer was extracted with methyl tert-butyl ether. The organic layer was dried over sodium sulfate and filtered, and the solvent removed by evaporation. The resulting oil was chromatographed over silica gel using heptane/ethyl acetate 20:1 as the eluent. 54 mg of the title compound were isolated as a pale yellow oil (48%).

Example Q 4-(2-Phenyl-chroman-6-yloxy)-cyclohexanol

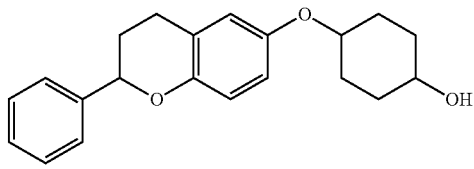 [SMILES: OC1CCC(Oc2ccc3c(c2)CCC(c2ccccc2)O3)CC1]

500 mg of 4-(2-phenyl-chroman-6-yloxy)-cyclohexanone (1.6 mmol) were dissolved at 0° C. in 2.5 ml of ethanol. 30 mg of sodium borohydride (0.78 mmol) were added in portions, and stirring at room temperature was continued for 2 h. The solvent was removed under reduced pressure and the residue separated between saturated aqueous sodium hydrogencarbonate solution and dichloromethane. The aqueous layer was extracted with dichloromethane. The combined organic layers were dried with sodium sulfate and filtered, and volatile components removed under reduced pressure. 500 mg of the title compound were obtained as a pale yellow solid.

Example R

3-Fluoro-isonicotinic acid 4-(2-phenyl-chroman-6-yloxy)-cyclohexyl ester

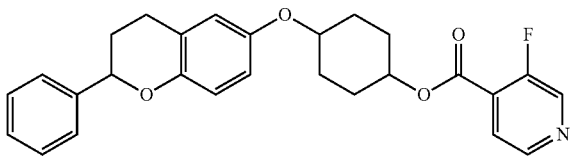 [SMILES: O=C(OC1CCC(Oc2ccc3c(c2)CCC(c2ccccc2)O3)CC1)c1ccncc1F]

To a solution of 158 mg of 3-fluoroisonicotinic acid (1.12 mmol) and 156 µl of triethylamine (1.12 mmol) in 16 ml of dichloromethane at 15° C. 138 µl of pivaloyl chloride (1.12 mmol) were added dropwise. The solution was stirred for 30 min. A solution of 110 mg of 4-(2-phenyl-chroman-6-yloxy)-cyclohexanol (0.34 mmol) in 4 ml of dichloromethane was added and 82 mg of 4-dimethylamino-pyridine (0.68 mmol) were added in one portion. Stirring at room temperature was continued for 16 h. The organic layer was washed with saturated aqueous sodium hydrogencarbonate solution, and the aqueous layer extracted with dichloromethane. The combined organic layers were dried over sodium sulfate and filtered, and the solvent removed by evaporation. The resulting oil was purified by reversed phase HPLC. 104 mg of the title compound were isolated as solid (69%).

Example S

1-Benzyl-4-(2-phenyl-chroman-6-yloxy)-cyclohexylamine

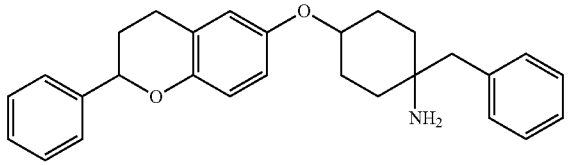 [SMILES: NC1(Cc2ccccc2)CCC(Oc2ccc3c(c2)CCC(c2ccccc2)O3)CC1]

a) To a solution of 352 mg of 4-(2-phenyl-chroman-6-yloxy)-cyclohexanone (1.1 mmol) in 10 ml of tetrahydrofuran at room temperature 0.46 ml of titanium(IV) ethoxide (2.18 mmol) and 139 mg of tert-butylsulfinamide (1.15 mmol) were added and the resulting solution heated to reflux for 16 h. The solution was cooled to 0° C. and 1.09 ml of benzylmagnesium chloride (2M in tetrahydrofuran, 2.18 mmol) were added. The mixture was stirred at room temperature for 16 h and additional 1.09 ml of benzylmagnesium chloride solution were added. After additional 16 h of stirring the reaction was stopped by careful addition of water. The suspension was filtered and the filter cake washed with dichloromethane. The aqueous layer was extracted with dichloromethane. The combined organic layers were dried over sodium sulfate and filtered, and the solvent removed by evaporation. The resulting oil was purified by chromatography over silica gel using a heptane/ethyl acetate gradient (0% ethyl acetate to 25% ethyl acetate). 248 mg of 2-methyl-propane-2-sulfinic acid [1-benzyl-4-(2-phenyl-chroman-6-yloxy)-cyclohexyl]-amide were isolated as a mixture of diastereomers (44%).

b) 120 mg of 2-methyl-propane-2-sulfinic acid [1-benzyl-4-(2-phenyl-chroman-6-yloxy)-cyclohexyl]-amide (0.23 mmol) were dissolved in 2 ml of trifluoroacetic acid in a sealed microwave tube and heated in a microwave reactor for 1 h at 130° C. The solvent was removed under reduced pressure and the resulting residue purified by reversed phase HPLC chromatography. 21 mg of 1-benzyl-4-(2-phenyl-chroman-6-yloxy)-cyclohexylamine were obtained as a solid (17%).

Example T

Phosphoric acid mono-(2-{[trans-4-((S)-2-o-tolyl-chroman-6-yloxy)-cyclohexanecarbonyl]-amino}-ethyl) ester disodium salt a) Phosphoric acid dibenzyl ester (2-{[trans-4-((S)-2-o-tolyl-chroman-6-yloxy)-cyclohexanecarbonyl]-amino}-ethyl) ester To a suspension of trans-4-((S)-2-o-tolyl-chroman-6-yloxy)-cyclohexanecarboxylic acid (2-hydroxy-ethyl)- amide (0.5 g, 1.22 mmol) and tetrazole (102 mg, 1.47 mmol, 1.2 eq) in dichloromethane (7 ml) and acetonitrile (7 ml) at 0° C., dibenzyl-N,N-diisopropylphophoramidite (0.46 g, 1.34 mmol, 1.1 eq) was added and the mixture stirred at 0° C. for 60 min (TLC control). To the resulting solution 3-chloro-perbenzoic acid (65%, 390 mg, 1.47 mmol, 1.2 eq) was added in one portion, and vigorous stirring at 0° C. was continued for 30 min (TLC control). The mixture was diluted with dichloromethane and the organic layer washed with a saturated aqueous solution of sodium hydrogencarbonate and subsequently with a saturated aqueous solution of ammonium chloride. The combined organic layers were dried over sodium sulfate and filtered, and the solvent removed under reduced pressure. The crude product was purified by column chromatography (silica gel, ethyl acetate/methanol gradient). Phosphoric acid dibenzyl ester (2-{[trans-4-((S)-2-o-tolyl-chroman-6-yloxy)-cyclohexanecarbonyl]-amino}-ethyl) ester was obtained as a colorless oil (0.66 g, 81%).

b) Phosphoric acid mono-(2-{[trans-4-((S)-2-o-tolyl-chroman-6-yloxy)-cyclohexanecarbonyl]-amino}-ethyl) ester disodium salt Phosphoric acid dibenzyl ester (2-{[trans-4-((S)-2-o-tolyl-chroman-6-yloxy)-cyclohexanecarbonyl]-amino}-ethyl) ester (0.33 g, 0.49 mmol) was dissolved in methanol (10 ml) and palladium on charcoal was added (10% Pd, 54% water, 0.3 g). The suspension was vigorously stirred for 1.5 h under a hydrogen atmosphere. The mixture was filtered and the filter cake rinsed with methanol. The filtrate was evaporated under reduced pressure and the resulting crude product submitted to preparative reversed phase HPLC purification (water/acetonitrile gradient (+0.1% trifluoroacetic acid)). The obtained phosphoric acid mono-(2-{[trans-4-((S)-2-o-tolyl-chroman-6-yloxy)-cyclohexanecarbonyl]-amino}-ethyl) ester was suspended in water and converted into the disodium salt by addition of 2 equivalents of an aqueous 0.5 N sodium hydroxide solution. The obtained aqueous solution was lyophilized to yield phosphoric acid mono-(2-{[trans-4-((S)-2-o-tolyl-chroman-6-yloxy)-cyclohexanecarbonyl]-amino}-ethyl) ester disodium salt as a white solid (113 mg, 43%).

In analogy to the procedures described above in the synthesis examples, the example compounds of the formula I listed in Table 1 were prepared. In Table 1, "Ex. no." means the number of the example compound; "LC/MS" means the LC/MS method described above which was used in the HPLC and MS characterization of the example compound; "MS" means the mass number (in amu) of the peak of the molecular ion or a related ion such as M+1 in the mass spectrum, in the case of a salt the mass number of the parent compound, i.e. of the free acid or base, unless another ion is specified; "Rt" means the HPLC retention time (in minutes); and "NCX1 rv IC$_{50}$" means the IC$_{50}$ value (in µM (micromol/liter) for inhibition of NCX1 in reverse mode determined in the assay for inhibition of Ca$^{2+}$ influx into cells (reverse mode) described below).

TABLE 1

Example compounds of the formula I

| Ex. no. | Compound name | LC/MS | MS (1) | Rt | NCX1rv IC$_{50}$ |
|---|---|---|---|---|---|
| 1 | [cis-4-(2-Phenylchroman-6-yloxy)cyclohexylmethyl]amine hydrochloride | A | 338.41 | 1.03 | 0.5 |
| 2 | cis-4-(2-Phenylchroman-6-yloxy)cyclohexylamine hydrochloride | B | 324.27 | 3.56 | 1.3 |
| 3 | N-[cis-4-(2-Phenylchroman-6-yloxy)cyclohexylmethyl]methanesulfonamide | A | 416.32 | 1.36 | 0.7 |
| 4 | N-[cis-4-(2-Phenylchroman-6-yloxy)cyclohexylmethyl]acetamide | A | 380.33 | 1.32 | 0.4 |
| 5 | trans-4-(2-Phenylchroman-6-yloxy)cyclohexylamine | C | 365.34 [M + H + CH$_3$CN]$^+$ | 3.81 | 0.3 |
| 6 | N-[cis-4-(2-Phenylchroman-6-yloxy)cyclohexyl]acetamide | A | 366.31 | 1.31 | 0.5 |
| 7 | N-[trans-4-(2-Phenylchroman-6-yloxy)cyclohexyl]acetamide | A | 366.17 | 1.18 | 0.3 |
| 8 | N-[trans-4-(2-Phenylchroman-6-yloxy)cyclohexyl]methanesulfonamide | B | 400.42 [M – H]$^-$ | 4.76 | 30 |
| 9 | trans-4-((R)-2-Phenylchroman-6-yloxy)cyclohexylamine hydrochloride | A | 324.24 | 0.99 | 0.3 |
| 10 | trans-4-((S)-2-Phenylchroman-6-yloxy)cyclohexylamine hydrochloride | A | 324.25 | 0.99 | 0.3 |
| 11 | 1-[1-Ethyl-4-(2-phenylchroman-6-yloxy)-cyclohexyl]propylamine hydrochloride | A | 394.39 | 1.20 | 2.8 |
| 12 | 2-Amino-N-[4-(2-phenylchroman-6-yloxy)cyclohexyl]acetamide hydrochloride | B | 381.33 | 3.62 | 0.2 |
| 13 | N-(Isoxazol-5-ylmethyl)-4-(2-phenylchroman-6-yloxy)-cyclohexanecarboxamide | A | 433.27 | 1.33 | 0.3 |
| 14 | N-(2-Ethyl-2H-pyrazol-3-ylmethyl)-4-(2-phenylchroman-6-yloxy)-cyclohexanecarboxamide | A | 460.34 | 1.34 | 0.4 |
| 15 | 2-[4-(2-Phenylchroman-6-yloxy)cyclohexylamino]ethanol | A | 368.26 | 1.11 | 0.2 |
| 16 | 1,1-Dimethyl-3-[4-(2-phenylchroman-6-yloxy)cyclohexyl]urea | A | 395.25 | 1.33 | 1.3 |
| 17 | 4-(2-Phenylchroman-6-yloxy)-1-propyl-cyclohexylamine hydrochloride | A | 366.25 | 1.16 | 1.0 |
| 18 | trans-4-((S)-2-Phenylchroman-6-yloxy)-N-propyl-cyclohexylamine | B | 366.31 | 3.75 | 0.5 |

TABLE 1-continued

Example compounds of the formula I

| Ex. no. | Compound name | LC/MS | MS (1) | Rt | NCX1rv IC$_{50}$ |
|---|---|---|---|---|---|
| 19 | 2-Methylsulfanyl-N-[trans-4-(2-phenylchroman-6-yloxy)cyclohexyl]acetamide | A | 412.2 | 1.35 | 0.1 |
| 20 | N-[trans-4-(2-Phenylchroman-6-yloxy)cyclohexyl]cyclobutanecarboxamide | B | 406.28 | 4.85 | 0.2 |
| 21 | 3-Methylsulfonyl-N-[trans-4-(2-phenylchroman-6-yloxy)cyclohexyl]propanamide | A | 458.22 | 1.29 | 0.2 |
| 22 | N-[trans-4-(2-Phenylchroman-6-yloxy)cyclohexyl]-2-(trifluoromethylsulfanyl)acetamide | A | 466.23 | 1.40 | 30 |
| 23 | (R)-2-Methoxy-N-[trans-4-(2-phenylchroman-6-yloxy)cyclohexyl]propanamide | A | 410.24 | 1.35 | 0.3 |
| 24 | N-[trans-4-(2-Phenylchroman-6-yloxy)cyclohexyl]-2-pyrazol-1-yl-acetamide | A | 432.26 | 1.32 | 0.3 |
| 25 | 2-(3-Methylisoxazol-5-yl)-N-[trans-4-(2-phenylchroman-6-yloxy)cyclohexyl]acetamide | A | 447.23 | 1.33 | 0.2 |
| 26 | N-[trans-4-(2-Phenylchroman-6-yloxy)cyclohexyl]cyclopropanecarboxamide | A | 392.22 | 1.34 | 0.1 |
| 27 | 2-Cyclopropyl-N-[trans-4-(2-phenylchroman-6-yloxy)cyclohexyl]acetamide | B | 406.28 | 4.81 | 0.2 |
| 28 | 2-(3-Methylpyrazol-1-yl)-N-[trans-4-(2-phenylchroman-6-yloxy)cyclohexyl]acetamide | A | 446.26 | 1.34 | 0.2 |
| 29 | 2-Methyl-N-[trans-4-(2-phenylchroman-6-yloxy)cyclohexyl]thiazole-4-carboxamide | A | 449.21 | 1.40 | 0.3 |
| 30 | 3-Methoxy-N-[trans-4-(2-phenylchroman-6-yloxy)cyclohexyl]propanamide | B | 410.31 | 4.66 | 0.3 |
| 31 | 3-Fluoro-N-[trans-4-(2-phenylchroman-6-yloxy)cyclohexyl]isonicotinamide | A | 447.22 | 1.36 | 0.1 |
| 32 | 2,2-Difluoro-N-[trans-4-(2-phenylchroman-6-yloxy)cyclohexyl]cyclopropanecarboxamide | A | 428.21 | 1.37 | 0.1 |
| 33 | 3,5-Dimethyl-N-[trans-4-(2-phenylchroman-6-yloxy)cyclohexyl]isoxazole-4-carboxamide | B | 447.29 | 4.84 | 30 |
| 34 | trans-4-((S)-2-Phenylchroman-6-yloxy)-N,N-dipropyl-cyclohexylamine | B | 408.34 | 4.06 | 1.3 |
| 35 | N-[trans-4-(2-Phenylchroman-6-yloxy)cyclohexyl]-2-([1,2,4]triazol-1-yl)acetamide | A | 433.23 | 1.27 | 0.1 |
| 36 | N-[trans-4-(2-Phenylchroman-6-yloxy)cyclohexyl]-3-(1,3,5-trimethylpyrazol-4-yl)propanamide | A | 488.59 | 1.29 | 0.3 |
| 37 | 3-(3,5-Dimethyl-1H-pyrazol-4-yl)-N-[trans-4-(2-phenylchroman-6-yloxy)cyclohexyl]propanamide | A | 474.3 | 1.23 | 0.3 |
| 38 | N-[trans-4-(2-Phenylchroman-6-yloxy)cyclohexyl]-3-([1,2,4]triazol-1-yl)propanamide | A | 447.27 | 1.26 | 0.4 |
| 39 | N-[trans-4-(2-Phenylchroman-6-yloxy)cyclohexyl]-3-pyrazol-1-yl-propanamide | A | 446.26 | 1.32 | 0.3 |
| 40 | 2-(2,5-Dimethylthiazol-4-yl)-N-[trans-4-(2-phenylchroman-6-yloxy)cyclohexyl]acetamide | A | 477.25 | 1.36 | 0.3 |
| 41 | 2-(3,5-Dimethylpyrazol-1-yl)-N-[trans-4-(2-phenylchroman-6-yloxy)cyclohexyl]acetamide | A | 460.48 | 1.35 | 0.3 |
| 42 | 3-(5-Methylpyrazol-1-yl)-N-[trans-4-(2-phenylchroman-6-yloxy)cyclohexyl]propanamide | A | 460.03 | 1.33 | 0.2 |
| 43 | 2-(3,5-Dimethyl-1H-pyrazol-4-yl)-N-[trans-4-(2-phenylchroman-6-yloxy)cyclohexyl]acetamide | A | 460.29 | 1.26 | 0.1 |
| 44 | 2-Hydroxy-2-methyl-N-[trans-4-(2-phenylchroman-6-yloxy)cyclohexyl]butanamide | A | 424.24 | 1.34 | 0.3 |
| 45 | 1-Benzyl-4-(2-phenylchroman-6-yloxy)-cyclohexylamine, stereoisomeric mixture 1 | B | 414.28 | 3.47 | 22 |
| 46 | 1-Benzyl-4-(2-phenylchroman-6-yloxy)-cyclohexylamine, stereoisomeric mixture 2 | A | 414.24 | 1.13 | 11 |
| 47 | trans-4-(2-Phenylchroman-6-yloxy)-N-(thiazol-5-ylmethyl)cyclohexylamine | A | 421.2 | 1.13 | 0.4 |
| 48 | N-(3-Methylsulfanylpropyl)-[trans-4-(2-phenylchroman-6-yloxy)]-cyclohexylamine | A | 412.24 | 1.17 | 0.5 |
| 49 | N-(5-Methylisoxazol-3-ylmethyl)-[trans-4-(2-phenylchroman-6-yloxy)]-cyclohexylamine | B | 419.29 | 3.78 | 0.6 |
| 50 | trans-4-(2-Phenylchroman-6-yloxy)-N-(thiophen-3-ylmethyl)cyclohexylamine | A | 420.25 | 1.04 | 0.6 |
| 51 | trans-4-(2-Phenylchroman-6-yloxy)-N-(thiophen-2-ylmethyl)cyclohexylamine | A | 420.18 | 1.17 | 0.6 |
| 52 | N-[(4-Methylthiazol-2-yl)methyl]-[trans-4-(2-phenylchroman-6-yloxy)]-cyclohexylamine | A | 435.23 | 1.16 | 0.5 |
| 53 | N-(Furan-3-ylmethyl)-[trans-4-(2-phenylchroman-6-yloxy)]-cyclohexylamine | A | 404.24 | 1.03 | 0.5 |
| 54 | trans-4-(2-Phenylchroman-6-yloxy)-N-(3,3,3-trifluoropropyl)cyclohexylamine | A | 420.26 | 1.03 | 0.6 |
| 55 | trans-4-(2-Phenylchroman-6-yloxy)-N-(thiazol-2-ylmethyl)cyclohexylamine | A | 421.21 | 1.14 | 0.4 |

TABLE 1-continued

Example compounds of the formula I

| Ex. no. | Compound name | LC/MS | MS (1) | Rt | NCX1rv IC$_{50}$ |
|---|---|---|---|---|---|
| 56 | N-(1,5-Dimethylpyrazol-3-ylmethyl)-[trans-4-(2-phenylchroman-6-yloxy)]-cyclohexylamine | A | 432.28 | 1.15 | 0.5 |
| 57 | N-(3-Methylimidazol-4-ylmethyl)-[trans-4-(2-phenylchroman-6-yloxy)]-cyclohexylamine | A | 418.24 | 1.02 | 0.5 |
| 58 | N-(2,2-Dimethylpropyl)-[trans-4-(2-phenylchroman-6-yloxy)]-cyclohexylamine | A | 394.31 | 1.05 | 0.6 |
| 59 | N-(2-Methylthiazol-4-ylmethyl)-[trans-4-(2-phenylchroman-6-yloxy)]-cyclohexylamine | B | 435.26 | 3.79 | 0.5 |
| 60 | trans-4-(2-Phenylchroman-6-yloxy)-N-(1,3,5-trimethylpyrazol-4-ylmethyl)cyclohexylamine | A | 446.25 | 1.15 | 0.4 |
| 61 | trans-4-(2-Phenylchroman-6-yloxy)-N-(tetrahydrofuran-3-ylmethyl)cyclohexylamine | A | 408.29 | 1.00 | 0.3 |
| 62 | N-(4-Chloro-1-methyl-pyrazol-3-ylmethyl)-[trans-4-(2-phenylchroman-6-yloxy)]-cyclohexylamine | A | 452.21 | 1.17 | 0.6 |
| 63 | N-(Cyclohexylmethyl)-[trans-4-(2-phenylchroman-6-yloxy)]-cyclohexylamine | A | 420.33 | 1.08 | 0.6 |
| 64 | N-(3-Methylsulfanylbutyl)-[trans-4-(2-phenylchroman-6-yloxy)]-cyclohexylamine | A | 426.28 | 1.05 | 0.5 |
| 65 | N-Isobutyl-[trans-4-(2-phenylchroman-6-yloxy)]-cyclohexylamine | A | 380.3 | 1.04 | 0.4 |
| 66 | N-(3-Methyl-1H-pyrazol-4-yl)methyl)-[trans-4-(2-phenylchroman-6-yloxy)]-cyclohexylamine | A | 418.26 | 1.13 | 0.4 |
| 67 | N-(4-Methylthiazol-5-ylmethyl)-[trans-4-(2-phenylchroman-6-yloxy)]-cyclohexylamine | A | 435.23 | 1.14 | 0.4 |
| 68 | N-(1-Ethyl-3-methyl-pyrazol-4-ylmethyl)-[trans-4-(2-phenylchroman-6-yloxy)]-cyclohexylamine | A | 446.29 | 1.15 | 0.3 |
| 69 | N-(5-Chloro-thiophen-2-ylmethyl)-[trans-4-(2-phenylchroman-6-yloxy)]-cyclohexylamine | A | 454.15 | 1.20 | 1.3 |
| 70 | N-(2-methylbutyl)-[trans-4-(2-phenylchroman-6-yloxy)]-cyclohexylamine | A | 394.31 | 1.06 | 0.5 |
| 71 | (S)-2-(Methylamino)-N-[trans-4-(2-phenylchroman-6-yloxy)cyclohexyl]propanamide hydrochloride | B | 409.27 | 3.66 | 0.6 |
| 72 | (R)-2-Amino-N-[trans-4-(2-phenylchroman-6-yloxy)cyclohexyl]propanamide hydrochloride | A | 395.22 | 1.00 | 0.3 |
| 73 | N-[trans-4-((S)-2-Phenylchroman-6-yloxy)cyclohexyl]morpholine-4-sulfonamide | A | 473.18 | 1.36 | 30 |
| 74 | 4-(2-Phenylchroman-6-yloxy)cyclohexanol | A | 325.24 | 1.33 | 0.3 |
| 75 | N-[trans-4-((S)-2-Phenylchroman-6-yloxy)cyclohexyl]-2-(pyridin-4-yl)ethanesulfonamide | A | 493.21 | 1.21 | 1.0 |
| 76 | N-(2-Ethyl-2H-pyrazol-3-ylmethyl)-4-(2-phenylchroman-6-yloxy)-cyclohexylamine | A | 432.28 | 1.15 | 1.0 |
| 77 | 4-(2-Phenylchroman-6-yloxy)cyclohexanone | A | 323.15 | 1.37 | 0.4 |
| 78 | [4-(2-Phenylchroman-6-yloxy)cyclohexyl] acetate | B | | | 0.6 |
| 79 | [trans-4-(2-Phenylchroman-6-yloxy)]-N,N-bis(thiophen-3-ylmethyl)cyclohexylamine | A | 516.23 | | 11 |
| 80 | N,N-Bis(cyclopropylmethyl)-[trans-4-(2-phenylchroman-6-yloxy)]-cyclohexylamine | A | 432.34 | 1.07 | 0.5 |
| 81 | N,N-Bis(4-chloro-1-methyl-pyrazol-3-ylmethyl)-[trans-4-(2-phenylchroman-6-yloxy)]-cyclohexylamine | A | 580.23 | 1.23 | 4.0 |
| 82 | N,N-Bis(5-methylisoxazol-3-ylmethyl)-[trans-4-(2-phenylchroman-6-yloxy)]-cyclohexylamine | A | 514.3 | 1.43 | 3.8 |
| 83 | [trans-4-(2-Phenylchroman-6-yloxy)]-N,N-bis(thiazol-5-ylmethyl)cyclohexylamine | A | 518.2 | 1.40 | 1.4 |
| 84 | N,N-Bis(1-methylpyrazol-3-ylmethyl)-[trans-4-(2-phenylchroman-6-yloxy)]-cyclohexylamine | B | 512.26 | 3.86 | 0.8 |
| 85 | N,N-Bis(furan-3-ylmethyl)-[trans-4-(2-phenylchroman-6-yloxy)]-cyclohexylamine | A | 484.27 | 1.20 | 0.8 |
| 86 | N,N-Bis(2-methylthiazol-4-ylmethyl)-[trans-4-(2-phenylchroman-6-yloxy)]-cyclohexylamine | B | 546.17 | | 0.8 |
| 87 | N,N-Bis(1,5-dimethylpyrazol-3-ylmethyl)-[trans-4-(2-phenylchroman-6-yloxy)]-cyclohexylamine | A | 540.34 | 1.20 | 1.3 |
| 88 | N,N-Bis(2-methylbutyl)-[trans-4-(2-phenylchroman-6-yloxy)]-cyclohexylamine | A | | | 2.5 |
| 89 | 3-Fluoro-isonicotinic acid 4-(2-phenyl-chroman-6-yloxy)-cyclohexyl ester | A | 448.26 | 1.46 | 0.4 |
| 90 | 4-(2-Phenylchroman-6-yloxy)-1-propyl-cyclohexanol | A | | | 0.2 |
| 91 | Methyl 2-{[cis-4-(2-phenylchroman-6-yloxy)cyclohexanecarbonyl]amino}acetate, stereoisomer 1 (2) | A | 424.23 | 1.33 | 0.4 |
| 92 | Methyl 2-[[cis-4-[2-phenylchroman-6-yloxy]cyclohexanecarbonyl]amino]acetate, stereoisomer 2 (2) | A | 424.22 | 1.33 | 0.1 |

TABLE 1-continued

Example compounds of the formula I

| Ex. no. | Compound name | LC/ MS | MS (1) | Rt | NCX1rv IC$_{50}$ |
|---|---|---|---|---|---|
| 93 | N-(2-Ethyl-2H-pyrazol-3-ylmethyl)-[cis-4-(2-phenylchroman-6-yloxy)]-cyclohexanecarboxamide, stereoisomer 1 (2) | A | 460.32 | 1.34 | 0.3 |
| 94 | N-(2-Ethyl-2H-pyrazol-3-ylmethyl)-[cis-4-(2-phenylchroman-6-yloxy)]-cyclohexanecarboxamide, stereoisomer 2 (2) | A | 460.3 | 1.34 | 1.6 |
| 95 | N-(5-Methyl-[1,2,4]oxadiazol-3-ylmethyl)-[4-cis-(2-phenylchroman-6-yloxy)]-cyclohexanecarboxamide, stereoisomer 1 (2) | A | 448.23 | 1.32 | 0.2 |
| 96 | N-(5-Methyl-[1,2,4]oxadiazol-3-ylmethyl)-[4-cis-(2-phenylchroman-6-yloxy)]-cyclohexanecarboxamide, stereoisomer 2 (2) | A | 448.27 | 1.33 | 0.4 |
| 97 | N-(5-Methyl-[1,2,4]oxadiazol-3-ylmethyl)-4-(2-phenylchroman-6-yloxy)-cyclohexylamine | B | 420.28 | 3.63 | 0.5 |
| 98 | N-Isopentyl-4-(2-phenylchroman-6-yloxy)-cyclohexylamine | A | 394.31 | 1.19 | 0.6 |
| 99 | N-(2-Hydroxyethyl)-4-((R)-2-phenylchroman-6-yloxy)-cyclohexanecarboxamide | B | 396.26 | 4.38 | 0.3 |
| 100 | 2-{(2-Methylbutyl)-[4-(2-phenylchroman-6-yloxy)cyclohexyl]amino}ethanol | A | 438.34 | 1.18 | 1.4 |
| 101 | N-(2-Methylbutyl)-4-(2-phenylchroman-6-yloxy)-cyclohexylamine | A | 394.31 | 1.19 | 0.9 |
| 102 | N-(2-Hydroxyethyl)-4-((S)-2-phenylchroman-6-yloxy)-cyclohexanecarboxamide | E | 395.83 | 1.13 | 1.1 |
| 103 | N-(Furan-3-ylmethyl)-4-(2-phenylchroman-6-yloxy)-cyclohexylamine | A | 404.23 | 1.16 | 0.8 |
| 104 | 4-(2-Phenylchroman-6-yloxy)-N-(1,3,5-trimethylpyrazol-4-ylmethyl)cyclohexylamine | A | 446.3 | 1.15 | 0.8 |
| 105 | N-Cyclohexyl-4-(2-phenylchroman-6-yloxy)-cyclohexylamine | F | 406.29 | 1.06 | 1.1 |
| 106 | N-(1-Methylbutyl)-4-(2-phenylchroman-6-yloxy)-cyclohexylamine | F | 394.29 | 1.06 | 0.8 |
| 107 | N-Isohexyl-4-(2-phenylchroman-6-yloxy)-cyclohexylamine | F | 408.3 | 1.08 | 0.8 |
| 108 | N-Butyl-4-(2-phenylchroman-6-yloxy)-cyclohexylamine | F | 380.27 | 1.04 | 0.6 |
| 109 | N-(1,2-Dimethylpropyl)-4-(2-phenylchroman-6-yloxy)-cyclohexylamine | F | 394.29 | 1.05 | 1.0 |
| 110 | N-(2-Methoxy-1-methyl-ethyl)-4-(2-phenylchroman-6-yloxy)-cyclohexylamine | F | 396.27 | 1.03 | 1.3 |
| 111 | N-(2-Methylsulfanylethyl)-4-(2-phenylchroman-6-yloxy)-cyclohexylamine | F | 398.24 | 1.03 | 0.6 |
| 112 | N-(3-Ethoxypropyl)-4-(2-phenylchroman-6-yloxy)-cyclohexylamine | F | 410.29 | 1.05 | 0.9 |
| 113 | 4-(2-Phenylchroman-6-yloxy)-N-propyl-cyclohexylamine | F | 366.25 | 1.02 | 0.5 |
| 114 | N-(3-Methylpentyl)-4-(2-phenylchroman-6-yloxy)-cyclohexylamine | F | 408.3 | 1.08 | 0.7 |
| 115 | N-(3-Methoxy-2,2-dimethyl-propyl)-4-(2-phenylchroman-6-yloxy)-cyclohexylamine | F | 424.29 | 1.07 | 1.0 |
| 116 | 4-(2-Phenylchroman-6-yloxy)-N-(3-tetrahydrofuran-3-ylpropyl)cyclohexylamine | F | 436.31 | 1.03 | 0.6 |
| 117 | N-(2-Cyclohexylsulfanylethyl)-4-(2-phenylchroman-6-yloxy)-cyclohexylamine | F | 466.3 | 1.11 | 3.7 |
| 118 | N-(1-Isopropylpiperidin-4-ylmethyl)-4-(2-phenylchroman-6-yloxy)-cyclohexylamine | E | 463.44 | 0.89 | 2.1 |
| 119 | N-(2-Isopropylsulfanylethyl)-4-(2-phenylchroman-6-yloxy)-cyclohexylamine | F | 426.27 | 1.07 | 1.1 |
| 120 | 4-(2-Phenylchroman-6-yloxy)-N-(2-tetrahydropyran-4-ylethyl)cyclohexylamine | F | 436.31 | 1.03 | 0.8 |
| 121 | N-(3-Methoxypropyl)-4-(2-phenylchroman-6-yloxy)-cyclohexylamine | F | 396.28 | 1.02 | 0.7 |
| 122 | N-(3-tert-Butoxypropyl)-4-(2-phenylchroman-6-yloxy)-cyclohexylamine | F | 438.32 | 1.08 | 1.2 |
| 123 | N-Cyclopropyl-4-(2-phenylchroman-6-yloxy)-cyclohexylamine | F | 364.25 | 1.02 | 1.0 |
| 124 | 4-(2-Phenylchroman-6-yloxy)-N-(1-propylcyclopropyl)cyclohexylamine | F | 406.29 | 1.07 | 2.4 |
| 125 | N-[4-(2-Phenylchroman-6-yloxy)cyclohexyl]tetrahydropyran-4-ylamine | F | 408.27 | 1.00 | 1.9 |
| 126 | N-[3-Cyclopentoxypropyl]-4-(2-phenylchroman-6-yloxy)-cyclohexylamine | F | 450.31 | 1.09 | 1.6 |
| 127 | N-(3,3-Dimethylbutyl)-4-(2-phenylchroman-6-yloxy)-cyclohexylamine | F | 408.31 | 1.08 | 1.1 |

TABLE 1-continued

Example compounds of the formula I

| Ex. no. | Compound name | LC/ MS | MS (1) | Rt | NCX1rv IC$_{50}$ |
|---|---|---|---|---|---|
| 128 | N1,N1-Dimethyl-N2-[4-(2-phenylchroman-6-yloxy)cyclohexyl]propane-1,2-diamine | E | 409.35 | 0.91 | 1.7 |
| 129 | 4-(2-Phenylchroman-6-yloxy)-N-(tetrahydrofuran-2-ylmethyl)cyclohexylamine | F | 408.28 | 1.03 | 0.7 |
| 130 | N-(3-Methylbutyl)-4-(2-phenylchroman-6-yloxy)-cyclohexylamine | F | 412.25 | 1.05 | 0.8 |
| 131 | N-(2-Ethylsulfanylethyl)-4-(2-phenylchroman-6-yloxy)-cyclohexylamine | F | 382.26 | 1.01 | 0.6 |
| 132 | N-(2-Methoxyethyl)-4-(2-phenylchroman-6-yloxy)-cyclohexylamine | F | 410.29 | 1.05 | 0.7 |
| 133 | N-[1-(Methoxymethyl)propyl]-4-(2-phenylchroman-6-yloxy)-cyclohexylamine | F | 424.3 | 1.06 | 1.0 |
| 134 | N-(3-Isopropoxypropyl)-4-(2-phenylchroman-6-yloxy)-cyclohexylamine | F | 424.31 | 1.06 | 1.1 |
| 135 | N-(2-tert-Butoxyethyl)-4-(2-phenylchroman-6-yloxy)-cyclohexylamine | E | 477.47 | 0.90 | 0.8 |
| 136 | N-[2-(1-Isopropylpiperidin-4-yl)ethyl]-4-(2-phenylchroman-6-yloxy)-cyclohexylamine | E | 421.39 | 0.88 | 1.8 |
| 137 | 4-(2-Phenylchroman-6-yloxy)-N-(2-pyrrolidin-1-ylethyl)cyclohexylamine | E | 485.35 | 1.00 | 1.3 |
| 138 | N-[2-(1,1-Dioxo-thiomorpholin-4-yl)ethyl]-4-(2-phenylchroman-6-yloxy)-cyclohexylamine | E | 453.35 | 0.99 | 0.6 |
| 139 | 4-(2-Phenylchroman-6-yloxy)-N-(2-thiomorpholin-4-ylethyl)cyclohexylamine | F | 396.27 | 1.03 | 1.0 |
| 140 | N-((S)-2-Methoxy-1-methyl-ethyl)-4-(2-phenylchroman-6-yloxy)-cyclohexylamine | F | 408.31 | 1.08 | 1.4 |
| 141 | N-(1,3-Dimethylbutyl)-4-(2-phenylchroman-6-yloxy)-cyclohexylamine | F | 378.26 | 1.03 | 1.0 |
| 142 | N-Cyclobutyl-4-(2-phenylchroman-6-yloxy)-cyclohexylamine | F | 392.28 | 1.04 | 0.6 |
| 143 | N-Cyclopentyl-4-(2-phenylchroman-6-yloxy)-cyclohexylamine | F | 394.29 | 1.07 | 0.8 |
| 144 | N-Pentyl-4-(2-phenylchroman-6-yloxy)-cyclohexylamine | E | 435.39 | 0.89 | 0.6 |
| 145 | 4-(2-Phenylchroman-6-yloxy)-N-(2-piperidin-1-ylethyl)cyclohexylamine | F | 420.31 | 1.08 | 2.1 |
| 146 | (trans-4-Methyl-cyclohexyl)-[4-(2-phenyl-chroman-6-yloxy)-cyclohexyl]-amine | F | 442.23 | 0.99 | 2.0 |
| 147 | 1,1-Dioxo-N-[4-(2-phenylchroman-6-yloxy)cyclohexyl]-tetrahydrothiophen-3-ylamine | F | 378.27 | 1.04 | 0.7 |
| 148 | N-But-3-enyl-4-(2-phenylchroman-6-yloxy)-cyclohexylamine | F | 366.26 | 1.02 | 0.9 |
| 149 | N-Isopropyl-4-(2-phenylchroman-6-yloxy)-cyclohexylamine | B | 364.32 | 3.68 | 1.4 |
| 150 | N-(3-Hydroxypropyl)-4-(2-phenylchroman-6-yloxy)-cyclohexanecarboxamide | A | 424.32 | 1.34 | 0.9 |
| 151 | N-(2-Hydroxy-1,1-dimethyl-ethyl)-4-(2-phenylchroman-6-yloxy)-cyclohexanecarboxamide | A | 408.37 | 1.22 | 1.3 |
| 152 | N-(3,3-Dimethylbutyl)-4-(2-phenylchroman-6-yloxy)-cyclohexylamine | E | 394.25 | 1.02 | 1.4 |
| 153 | N-{trans-4-[2-(o-Tolyl)chroman-6-yloxy]cyclohexyl}-3-pyrazol-1-yl-propanamide | E | 460.31 | 1.22 | 1.2 |
| 154 | (Tetrahydrofuran-3-ylmethyl)-[trans-4-(2-o-tolyl-chroman-6-yloxy)-cyclohexyl]-amine | E | 422.33 | 1.02 | 2.2 |
| 155 | Bis-(tetrahydrofuran-3-ylmethyl)-[trans-4-(2-o-tolyl-chroman-6-yloxy)-cyclohexyl]-amine | E | 506.39 | 1.04 | 5.3 |
| 156 | trans-4-[2-(o-Tolyl)chroman-6-yloxy]cyclohexylamine hydrochloride | E | 338.32 | 0.99 | 0.6 |
| 157 | N,N-Bis(2-hydroxyethyl)-4-(2-phenylchroman-6-yloxy)-cyclohexanecarboxamide | A | | | 2.0 |
| 158 | N-(Isoxazol-5-ylmethyl)-4-[2-(o-tolyl)chroman-6-yloxy]-cyclohexanecarboxamide | E | 447.28 | 1.22 | 0.4 |
| 159 | 2-Amino-N-[trans-4-((S)-2-phenylchroman-6-yloxy)cyclohexyl]acetamide hydrochloride | A | 381.35 | 1.12 | 0.2 |
| 160 | 2-Amino-N-[trans-4-((R)-2-phenylchroman-6-yloxy)cyclohexyl]acetamide hydrochloride | A | 381.38 | 1.12 | 1.1 |
| 161 | N-(2,2-Dimethylpropyl)-4-(2-phenylchroman-6-yloxy)-cyclohexylamine | E | | | 1.3 |
| 162 | N-(2,2-Dimethylpropyl)-4-(2-phenylchroman-6-yloxy)-cyclohexylamine | B | | | 2.3 |
| 163 | 1-Methyl-4-(2-phenylchroman-6-yloxy)-cyclohexanol | B | 677.57 [2M + H]$^+$ | 4.84 | 0.6 |
| 164 | 4-[2-(2,6-Dimethylphenyl)chroman-6-yloxy]-N-(1,3,5-trimethylpyrazol-4-ylmethyl)cyclohexylamine | A | 474.53 | 1.19 | 9.4 |

TABLE 1-continued

Example compounds of the formula I

| Ex. no. | Compound name | LC/MS | MS (1) | Rt | NCX1rv IC$_{50}$ |
|---|---|---|---|---|---|
| 165 | 4-[2-(2,6-Dimethylphenyl)chroman-6-yloxy]-N-(3-methylsulfanylbutyl)cyclohexylamine | A | 454.5 | 1.22 | 10 |
| 166 | 4-[2-(2,6-Dimethylphenyl)chroman-6-yloxy]-N-(2-hydroxyethyl)cyclohexanecarboxamide | A | 424.44 | 1.32 | 6.2 |
| 167 | 4-[2-(2,6-Dimethylphenyl)chroman-6-yloxy]-N-(isoxazol-5-ylmethyl)cyclohexanecarboxamide | A | 461.42 | 1.38 | 7.7 |
| 168 | trans-4-[2-(2,6-Dimethylphenyl)chroman-6-yloxy]cyclohexylamine hydrochloride | A | 352.35 | 1.16 | 4.0 |
| 169 | 4-[2-(2-Fluorophenyl)chroman-6-yloxy]-N-(1,3,5-trimethylpyrazol-4-ylmethyl)cyclohexylamine | E | 464.44 | 1.04 | 2.5 |
| 170 | 4-[2-(2-Fluorophenyl)chroman-6-yloxy]-N-(3-methylsulfanylbutyl)cyclohexylamine | B | 444.43 | 3.87 | 4.6 |
| 171 | trans-4-[2-(2,6-Dimethylphenyl)chroman-6-yloxy]-N-(tetrahydrofuran-3-ylmethyl)cyclohexylamine | A | 436.33 | 1.17 | 8.3 |
| 172 | N-[trans-4-[2-(2,6-Dimethylphenyl)chroman-6-yloxy]cyclohexyl]-3-pyrazol-1-yl-propanamide | A | 474.31 | 1.37 | 7.1 |
| 173 | 4-[2-(2-Fluorophenyl)chroman-6-yloxy]-N-(2-hydroxyethyl)cyclohexanecarboxamide | A | 414.23 | 1.27 | 0.7 |
| 174 | 4-[2-(2-Fluorophenyl)chroman-6-yloxy]-N-(isoxazol-5-ylmethyl)cyclohexanecarboxamide | A | 451.24 | 1.33 | 0.6 |
| 175 | N-(3-Methylsulfanylbutyl)-4-[2-(o-tolyl)chroman-6-yloxy]-cyclohexylamine | B | 440.46 | 4.06 | 3.5 |
| 176 | trans-4-[2-(2-Fluorophenyl)chroman-6-yloxy]cyclohexylamine hydrochloride | E | 342.22 | 1.00 | 1.3 |
| 177 | [4-(2-o-Tolyl-chroman-6-yloxy)-cyclohexyl]-(1,3,5-trimethylpyrazol-4-ylmethyl)-amine | A | 460.34 | 1.16 | 3.2 |
| 178 | trans-4-[2-(2-Fluorophenyl)chroman-6-yloxy]-N-(tetrahydrofuran-3-ylmethyl)cyclohexylamine | B | 426.48 | 3.63 | 1.6 |
| 179 | N-[trans-4-[2-(2-Fluorophenyl)chroman-6-yloxy]cyclohexyl]-3-pyrazol-1-yl-propanamide | A | 464.27 | 1.30 | 1.2 |
| 180 | (S)-N-[trans-4-(2-Phenylchroman-6-yloxy)cyclohexyl]pyrrolidine-2-carboxamide hydrochloride | A | 421.3 | 1.14 | 0.8 |
| 181 | (S)-2-Amino-3-hydroxy-N-[trans-4-(2-phenylchroman-6-yloxy)cyclohexyl]propanamide hydrochloride | A | 411.27 | 1.11 | 0.3 |
| 182 | N-[trans-4-(2-Phenylchroman-6-yloxy)cyclohexyl]-2-pyrrolidin-1-yl-acetamide | A | 435.29 | 1.14 | 0.3 |
| 183 | N-(2-Ethyl-2H-pyrazol-3-ylmethyl)-4-[2-(2-fluorophenyl)chroman-6-yloxy]-cyclohexanecarboxamide | A | 478.34 | 1.32 | 10 |
| 184 | N-(2-Chloro-pyridin-4-ylmethyl)-4-[2-(2-fluorophenyl)chroman-6-yloxy]-cyclohexanecarboxamide | A | 495.3 | 1.35 | 1.3 |
| 185 | 2-Amino-N-{cis-4-[2-(o-tolyl)chroman-6-yloxy]cyclohexylmethyl}acetamide hydrochloride | A | 409.26 | 1.15 | 0.6 |
| 186 | 2-Amino-N-{trans-4-[2-(5-fluoro-2-methyl-phenyl)chroman-6-yloxy]cyclohexyl}acetamide | A | 413.26 | 1.14 | 0.4 |
| 187 | 4-[2-(o-Tolyl)chroman-6-yloxy]-N-(tetrahydrofuran-2-ylmethyl)cyclohexylamine | E | 422.34 | 1.05 | 99% (3) |
| 188 | N-(2-Methoxy-1-methyl-ethyl)-4-[2-(o-tolyl)chroman-6-yloxy]-cyclohexylamine | E | 410.32 | 1.05 | 96% (3) |
| 189 | N-(2-Methoxyethyl)-4-[2-(o-tolyl)chroman-6-yloxy]-cyclohexylamine | E | 396.29 | 1.03 | 100% (3) |
| 190 | N-(3-Isopropoxypropyl)-4-[2-(o-tolyl)chroman-6-yloxy]-cyclohexylamine | E | 438.37 | 1.08 | 93% (3) |
| 191 | N-(2-Ethylsulfanylethyl)-4-[2-(o-tolyl)chroman-6-yloxy]-cyclohexylamine | E | 426.3 | 1.07 | 95% (3) |
| 192 | N-(2-Methylsulfanylethyl)-4-[2-(o-tolyl)chroman-6-yloxy]-cyclohexylamine | E | 412.28 | 1.05 | 98% (3) |
| 193 | N-(3-Methoxypropyl)-4-[2-(o-tolyl)chroman-6-yloxy]-cyclohexylamine | E | 410.31 | 1.04 | 99% (3) |
| 194 | N-(2-Isopropylsulfanylethyl)-4-[2-(o-tolyl)chroman-6-yloxy]-cyclohexylamine | E | 440.33 | 1.08 | 85% (3) |
| 195 | N-[1-(Methoxymethyl)propyl]-4-[2-(o-tolyl)chroman-6-yloxy]-cyclohexylamine | E | 424.36 | 1.06 | 96% (3) |
| 196 | 4-[2-(o-Tolyl)chroman-6-yloxy]-N-(2-tetrahydropyran-4-ylethyl)cyclohexylamine | E | 450.39 | 1.05 | 97% (3) |
| 197 | N-{4-[2-(o-Tolyl)chroman-6-yloxy]cyclohexyl}tetrahydropyran-4-ylamine | E | 422.36 | 1.03 | 96% (3) |
| 198 | 4-[2-(o-Tolyl)chroman-6-yloxy]-N-(3-tetrahydrofuran-3-ylpropyl)cyclohexylamine | E | 450.35 | 1.05 | 97% (3) |
| 199 | N-[3-Cyclopentoxypropyl)-4-[2-(o-tolyl)chroman-6-yloxy]-cyclohexylamine | E | 464.42 | 1.10 | 71% (3) |

TABLE 1-continued

Example compounds of the formula I

| Ex. no. | Compound name | LC/ MS | MS (1) | Rt | NCX1rv IC$_{50}$ |
|---|---|---|---|---|---|
| 200 | N-(3-Methoxy-2,2-dimethyl-propyl)-4-[2-(o-tolyl)chroman-6-yloxy]-cyclohexylamine | E | 438.46 | 1.08 | 94% (3) |
| 201 | N-(3-Ethoxypropyl)-4-[2-(o-tolyl)chroman-6-yloxy]-cyclohexylamine | E | 424.33 | 1.06 | 98% (3) |
| 202 | N-(2-Morpholin-4-ylethyl)-4-[2-(o-tolyl)chroman-6-yloxy]-cyclohexylamine | E | 451.36 | 1.00 | 1.9 |
| 203 | N-Cyclopropyl-4-[2-(o-tolyl)chroman-6-yloxy]-cyclohexylamine | E | 378.28 | 1.04 | 1.5 |
| 204 | N-Cyclopentyl-4-[2-(o-tolyl)chroman-6-yloxy]-cyclohexylamine | E | 406.33 | 1.06 | 1.9 |
| 205 | 4-[2-(o-Tolyl)chroman-6-yloxy]-N-propyl-cyclohexylamine | B | 380.35 | 3.84 | 1.5 |
| 206 | N-[4-[2-(o-Tolyl)chroman-6-yloxy]cyclohexyl]-1,1-dioxo-tetrahydrothiophen-3-ylamine | E | 456.26 | 1.02 | 1.1 |
| 207 | N-((S)-2-Methoxy-1-methyl-ethyl)-4-[2-(o-tolyl)chroman-6-yloxy]-cyclohexylamine | E | 410.32 | 1.05 | 1.5 |
| 208 | 4-[2-(o-Tolyl)chroman-6-yloxy]-N-(tetrahydropyran-4-ylmethyl)cyclohexylamine | E | 436.33 | 1.03 | 3.0 |
| 209 | 4-[2-(o-Tolyl)chroman-6-yloxy]-N-(2-thiomorpholin-4-ylethyl)cyclohexylamine | E | 467.33 | 1.02 | 3.2 |
| 210 | N-{4-[2-(2-Fluorophenyl)chroman-6-yloxy]cyclohexyl}-1,1-dioxo-tetrahydrothiophen-3-ylamine | E | 460.2 | 1.00 | 1.1 |
| 211 | 4-[2-(2-Fluorophenyl)chroman-6-yloxy]-N-(3-methoxy-2,2-dimethyl-propyl)cyclohexylamine | E | 442.33 | 1.07 | 2.2 |
| 212 | N-Cyclopropyl-4-[2-(2-fluorophenyl)chroman-6-yloxy]-cyclohexylamine | E | 382.23 | 1.02 | 1.7 |
| 213 | 4-[2-(2-Fluorophenyl)chroman-6-yloxy]-N-propyl-cyclohexylamine | E | 384.26 | 1.03 | 1.4 |
| 214 | 4-[2-(2-Fluorophenyl)chroman-6-yloxy]-N-(2-methoxyethyl)cyclohexylamine | E | 400.24 | 1.02 | 1.6 |
| 215 | 4-[2-(2-Fluorophenyl)chroman-6-yloxy]-N-(3-methoxypropyl)cyclohexylamine | E | 414.27 | 1.03 | 2.8 |
| 216 | 4-[2-(2-Fluorophenyl)chroman-6-yloxy]-N-(tetrahydrofuran-2-ylmethyl)cyclohexylamine | E | 426.27 | 1.03 | 1.7 |
| 217 | N-(2-Ethylsulfanylethyl)-4-[2-(2-fluorophenyl)chroman-6-yloxy]-cyclohexylamine | E | 430.27 | 1.05 | 2.3 |
| 218 | N-Cyclopentyl-4-[2-(2-fluorophenyl)chroman-6-yloxy]-cyclohexylamine | E | 410.27 | 1.05 | 2.8 |
| 219 | 4-[2-(2-Fluorophenyl)chroman-6-yloxy]-N-(2-methoxy-1-methyl-ethyl)cyclohexylamine | E | 414.29 | 1.03 | 2.4 |
| 220 | 4-[2-(2-Fluorophenyl)chroman-6-yloxy]-N-(2-tetrahydropyran-4-ylethyl)cyclohexylamine | E | 454.32 | 1.03 | 2.4 |
| 221 | 4-[2-(2-Fluorophenyl)chroman-6-yloxy]-N-((S)-2-methoxy-1-methyl-ethyl)cyclohexylamine | E | 414.29 | 1.03 | 2.3 |
| 222 | 4-[2-(2-Fluorophenyl)chroman-6-yloxy]-N-[1-(methoxymethyl)propyl]cyclohexylamine | E | 428.32 | 1.05 | 3.1 |
| 223 | N-(3-Ethoxypropyl)-4-[2-(2-fluorophenyl)chroman-6-yloxy]-cyclohexylamine | E | 428.32 | 1.05 | 3.1 |
| 224 | 4-[2-(2-Fluorophenyl)chroman-6-yloxy]-N-(2-morpholin-4-ylethyl)cyclohexylamine | E | 455.34 | 0.98 | 3.5 |
| 225 | 4-[2-(2-Fluorophenyl)chroman-6-yloxy]-N-(3-isopropoxypropyl)cyclohexylamine | B | 442.41 | 3.97 | 3.9 |
| 226 | 4-[2-(2-Fluorophenyl)chroman-6-yloxy]-N-(2-methylsulfanylethyl)cyclohexylamine | E | 416.26 | 1.03 | 2.4 |
| 227 | 4-[2-(2-Fluorophenyl)chroman-6-yloxy]-N-(2-thiomorpholin-4-ylethyl)cyclohexylamine | E | 471.3 | 1.00 | 4.3 |
| 228 | 4-[2-(2-Fluorophenyl)chroman-6-yloxy]-N-(3-tetrahydrofuran-3-ylpropyl)cyclohexylamine | E | 454.32 | 1.03 | 2.2 |
| 229 | N-(3-Cyclopentoxypropyl)-4-[2-(2-fluorophenyl)chroman-6-yloxy]-cyclohexylamine | E | 468.35 | 1.09 | 6.0 |
| 230 | N-Butyl-4-[2-(2-fluorophenyl)chroman-6-yloxy]-cyclohexylamine | E | 398.29 | 1.05 | 2.9 |
| 231 | N-{4-[2-(2-Fluorophenyl)chroman-6-yloxy]cyclohexyl}tetrahydropyran-4-ylamine | E | 426.28 | 1.01 | 4.1 |
| 232 | 4-[2-(2-Fluorophenyl)chroman-6-yloxy]-N-(2-isopropylsulfanylethyl)cyclohexylamine | E | 444.29 | 1.07 | 5.9 |
| 233 | 2-(3,5-Dimethylpyrazol-1-yl)-N-{trans-4-[2-(2-fluorophenyl)chroman-6-yloxy]cyclohexyl}acetamide | E | 478.32 | 1.23 | 30 |
| 234 | 3-(3,5-Dimethyl-1H-pyrazol-4-yl)-N-{trans-4-[2-(2-fluorophenyl)chroman-6-yloxy]cyclohexyl}propanamide | E | 492.33 | 1.12 | 0.1 |
| 235 | 2-(3,5-Dimethyl-1H-pyrazol-4-yl)-N-{trans-4-[2-(2-fluorophenyl)chroman-6-yloxy]cyclohexyl}acetamide | E | 478.3 | 1.14 | 1.5 |

TABLE 1-continued

Example compounds of the formula I

| Ex. no. | Compound name | LC/ MS | MS (1) | Rt | NCX1rv IC$_{50}$ |
|---|---|---|---|---|---|
| 236 | N-{trans-4-[2-(2-Fluorophenyl)chroman-6-yloxy]cyclohexyl}-2-pyrazol-1-yl-acetamide | E | 450.29 | 1.20 | 0.1 |
| 237 | N-{trans-4-[2-(2-Fluorophenyl)chroman-6-yloxy]cyclohexyl}-3-([1,2,4]triazol-1-yl)propanamide | E | 465.29 | 1.15 | 0.2 |
| 238 | N-{trans-4-[2-(2-Fluorophenyl)chroman-6-yloxy]cyclohexyl}-2-hydroxy-2-methyl-butanamide | E | 442.24 | 1.23 | 0.1 |
| 239 | N-{trans-4-[2-(2-Fluorophenyl)chroman-6-yloxy]cyclohexyl}cyclopropanecarboxamide | E | 410.25 | 1.23 | 0.1 |
| 240 | 3,3,3-Trifluoro-N-{trans-4-[2-(2-fluoro-phenyl)chroman-6-yloxy]cyclohexyl}propanamide | E | 452.21 | 1.25 | 0.1 |
| 241 | N-{trans-4-[2-(2-Fluorophenyl)chroman-6-yloxy]cyclohexyl}-2-methylsulfanyl-acetamide | E | 430.22 | 1.24 | 0.04 |
| 242 | N-{trans-4-[2-(2-Fluorophenyl)chroman-6-yloxy]cyclohexyl}-3,5-dimethyl-isoxazole-4-carboxamide | E | 465.25 | 1.25 | 0.5 |
| 243 | N-{trans-4-[2-(2-Fluorophenyl)chroman-6-yloxy]cyclohexyl}-3-methoxy-propanamide | E | 428.23 | 1.20 | 0.7 |
| 244 | N-{[trans-4-[2-(2-Fluorophenyl)chroman-6-yloxy]cyclohexyl}cyclobutanecarboxamide | E | 424.27 | 1.26 | 0.1 |
| 245 | 2-(2,5-Dimethylthiazol-4-yl)-N-{trans-4-[2-(2-fluorophenyl)chroman-6-yloxy]cyclohexyl}acetamide | E | 495.37 | 1.25 | 0.3 |
| 246 | 3-Fluoro-N-{trans-4-[2-(2-fluorophenyl)chroman-6-yloxy]cyclohexyl}pyridine-4-carboxamide | E | 465.25 | 1.24 | 0.1 |
| 247 | N-{trans-4-[2-(2-Fluorophenyl)chroman-6-yloxy]cyclohexyl}-2-methyl-thiazole-4-carboxamide | E | 467.25 | 1.28 | 0.3 |
| 248 | N-{trans-4-[2-(2-Fluorophenyl)chroman-6-yloxy]cyclohexyl}-3-(3-methyl-[1,2,4]oxadiazol-5-yl)propanamide | E | 480.26 | 1.21 | 0.2 |
| 249 | N-{trans-4-[2-(2-Fluorophenyl)chroman-6-yloxy]cyclohexyl}-2-(3-methylisoxazol-5-yl)acetamide | E | 465.25 | 1.22 | 1.1 |
| 250 | N-{trans-4-[2-(2-Fluorophenyl)chroman-6-yloxy]cyclohexyl}-2-(3-methylpyrazol-1-yl)acetamide | E | 464.3 | 1.22 | 0.8 |
| 251 | 2,2-Difluoro-N-{trans-4-[2-(2-fluorophenyl)chroman-6-yloxy]cyclohexyl}cyclopropanecarboxamide | E | 446.24 | 1.25 | 5.0 |
| 252 | 2-Cyclopropyl-N-{trans-4-[2-(2-fluoro-phenyl)chroman-6-yloxy]cyclohexyl}acetamide | E | 424.29 | 1.24 | 0.3 |
| 253 | N-{trans-4-[2-(2-Fluorophenyl)chroman-6-yloxy]cyclohexyl}-3-pyrazol-1-yl-propanamide | E | 464.3 | 1.20 | 0.3 |
| 254 | N-{trans-4-[2-(2-Fluorophenyl)chroman-6-yloxy]cyclohexyl}-3-(1,3,5-trimethylpyrazol-4-yl)propanamide | E | 506.34 | 1.17 | 0.3 |
| 255 | (R)-N-{trans-4-[2-(2-Fluorophenyl)chroman-6-yloxy]cyclohexyl}-2-methoxy-propanamide | E | 428.27 | 1.24 | 0.2 |
| 256 | N-{trans-4-[2-(2-Fluorophenyl)chroman-6-yloxy]cyclohexyl}-2-([1,2,4]triazol-1-yl)acetamide | E | 451.27 | 1.16 | 0.1 |
| 257 | N-{trans-4-[2-(2-Fluorophenyl)chroman-6-yloxy]cyclohexyl}-3-(5-methylpyrazol-1-yl)propanamide | E | 478.31 | 1.22 | 0.2 |
| 258 | 3-(1,5-Dimethylpyrazol-4-yl)-N-{trans-4-[2-(2-fluorophenyl)chroman-6-yloxy]cyclohexyl}propanamide | B | 492.38 | 4.64 | 0.2 |
| 259 | N-{trans-4-[2-(2-Fluorophenyl)chroman-6-yloxy]cyclohexyl}-3-methylsulfonyl-propanamide | E | 476.21 | 1.17 | 0.1 |
| 260 | N-{trans-4-[2-(2-Fluorophenyl)chroman-6-yloxy]cyclohexyl}-2-(trifluoromethylsulfanyl)acetamide | E | 484.2 | 1.28 | 0.4 |
| 261 | N-{trans-4-[2-(2-Fluorophenyl)chroman-6-yloxy]cyclohexyl}-5-methyl-1H-pyrazole-3-carboxamide | E | 450.26 | 1.20 | 0.3 |
| 262 | 4-[2-(3-Fluoro-2-methyl-phenyl)chroman-6-yloxy]-N-(2-hydroxyethyl)cyclohexanecarboxamide | A | 428.18 | 1.29 | 0.2 |
| 263 | 4-[2-(3-Fluoro-2-methyl-phenyl)chroman-6-yloxy]-N-(isoxazol-5-ylmethyl)cyclohexanecarboxamide | A | 465.17 | 1.35 | 0.1 |
| 264 | N-[2-Hydroxy-1-(hydroxymethyl)ethyl]-4-[2-(o-tolyl)chroman-6-yloxy]-cyclohexanecarboxamide | A | 440.19 | 1.25 | 0.2 |
| 265 | cis-4-[2-(o-Tolyl)chroman-6-yloxy]-N-(pyridin-2-yl)cyclohexanecarboxamide | A | 443.2 | 1.38 | 0.4 |
| 266 | trans-4-[2-(o-Tolyl)chroman-6-yloxy]-N-(pyridin-2-yl)cyclohexanecarboxamide | A | 443.2 | 1.39 | 0.3 |

TABLE 1-continued

Example compounds of the formula I

| Ex. no. | Compound name | LC/MS | MS (1) | Rt | NCX1rv IC$_{50}$ |
|---|---|---|---|---|---|
| 267 | trans-4-((R)-2-o-tolyl-chroman-6-yloxy)-cyclohexanecarboxylic acid (2-hydroxy-ethyl)-amide | A | 410.2 | 1.28 | 0.2 |
| 268 | trans-4-((S)-2-o-tolyl-chroman-6-yloxy)-cyclohexanecarboxylic acid (2-hydroxy-ethyl)-amide | E | 410.3 | 1.16 | 0.15 |
| 269 | cis-4-(2-o-tolyl-chroman-6-yloxy)-cyclohexanecarboxylic acid (2-hydroxy-ethyl)-amide, stereoisomer 1 (2) | A | 410.2 | 1.28 | 0.4 |
| 270 | cis-4-(2-o-tolyl-chroman-6-yloxy)-cyclohexanecarboxylic acid (2-hydroxy-ethyl)-amide, stereoisomer 2 (2) | A | 410.2 | 1.28 | 0.1 |
| 271 | 2-{trans-4-[2-(o-Tolyl)chroman-6-yloxy]cyclohexylamino}acetic acid | A | 396.17 | 1.17 | 0.8 |
| 272 | N-Carbamoylmethyl-4-[2-(3-fluoro-2-methyl-phenyl)chroman-6-yloxy]-cyclohexanecarboxamide | A | 441.16 | 1.27 | 0.4 |
| 273 | N-Dimethylcarbamoylmethyl-4-[2-(3-fluoro-2-methyl-phenyl)chroman-6-yloxy]-cyclohexanecarboxamide | A | 469.19 | 1.32 | 0.6 |
| 274 | N-[2-(Dimethylsulfamoyl)ethyl]-4-[2-(3-fluoro-2-methyl-phenyl)chroman-6-yloxy]-cyclohexanecarboxamide | A | 519.18 | 1.35 | 0.6 |
| 275 | 4-[2-(3-Fluoro-2-methyl-phenyl)chroman-6-yloxy]-N-[2-(methylsulfamoyl)ethyl]cyclohexane-carboxamide | A | 505.16 | 1.32 | 0.4 |
| 276 | 4-[2-(3-Fluoro-2-methyl-phenyl)chroman-6-yloxy]-N-(2-hydroxypropyl)cyclohexanecarboxamide | A | 442.19 | 1.31 | 0.6 |
| 277 | 4-[2-(3-Fluoro-2-methyl-phenyl)chroman-6-yloxy]-N-[2-(methanesulfonamido)ethyl]cyclohexane-carboxamide | D | 505 | 4.42 | 0.3 |
| 278 | 2-Hydroxy-N-[trans-4-(2-phenylchroman-6-yloxy)cyclohexyl]acetamide | A | 382.18 | 1.26 | 0.2 |
| 279 | 4-[2-(3-Fluoro-2-methyl-phenyl)chroman-6-yloxy]-N-(2-hydroxycyclopentyl)cyclohexane-carboxamide, stereoisomer 1 (2) | A | 468.24 | 1.34 | 0.7 |
| 280 | 4-[2-(3-Fluoro-2-methyl-phenyl)chroman-6-yloxy]-N-(2-hydroxycyclopentyl)cyclohexane-carboxamide, stereoisomer 2 (2) | A | 512.36 [M − H + HCO$_2$H]$^-$ | 1.37 | 0.1 |
| 281 | 4-[2-(3-Fluoro-2-methyl-phenyl)chroman-6-yloxy]-N-methylcarbamoylmethyl-cyclohexane-carboxamide | A | 455.21 | 1.29 | 0.5 |
| 282 | 4-[2-(3-Fluoro-2-methyl-phenyl)chroman-6-yloxy]-N-(3-methylsulfanylbutyl)cyclohexanecarboxamide | E | 486.16 | 1.42 | 0.4 |
| 283 | N-(2-Ethyl-2H-pyrazol-3-ylmethyl)-4-[2-(3-fluoro-2-methyl-phenyl)chroman-6-yloxy]-cyclohexanecarboxamide | E | 492.19 | 1.36 | 0.6 |
| 284 | 4-[2-(3-Fluoro-2-methyl-phenyl)chroman-6-yloxy]-N-{[(1S,2R)-2-hydroxycyclohexyl]methyl}cyclo-hexanecarboxamide | E | 496.19 | 1.39 | 0.8 |
| 285 | 4-[2-(3-Fluoro-2-methyl-phenyl)chroman-6-yloxy]-N-[(1S,2S)-2-hydroxycyclohexyl]cyclohexane-carboxamide, stereoisomeric mixture 1 | E | 482.17 | 1.36 | 0.5 |
| 286 | 4-[2-(3-Fluoro-2-methyl-phenyl)chroman-6-yloxy]-N-[(1S,2S)-2-hydroxycyclohexyl]cyclohexane-carboxamide, stereoisomeric mixture 2 | E | 482.18 | 1.36 | 0.5 |
| 287 | 4-[2-(3-Fluoro-2-methyl-phenyl)chroman-6-yloxy]-N-[(1S,2S)-2-hydroxycyclohexyl]cyclohexane-carboxamide, stereoisomeric mixture 3 | E | 482.18 | 1.38 | 0.1 |
| 288 | N-(2-Hydroxyethyl)-4-[7-methyl-2-(o-tolyl)chroman-6-yloxy]-cyclohexanecarboxamide | E | 424.13 | 1.35 | 1.9 |
| 289 | N-(Isoxazol-5-ylmethyl)-4-[7-methyl-2-(o-tolyl)chroman-6-yloxy]-cyclohexanecarboxamide | E | 461.12 | 1.41 | 1.3 |
| 290 | N-[2-Ethyl-2H-pyrazol-3-ylmethyl]-4-[7-methyl-2-(o-tolyl)chroman-6-yloxy]-cyclohexanecarboxamide | E | 488.17 | 1.41 | 1.5 |
| 291 | 4-(5-Chloro-2-phenyl-chroman-6-yloxy)-N-(2-hydroxyethyl)cyclohexanecarboxamide | E | 430.09 | 1.30 | 1.1 |
| 292 | 4-(5-Chloro-2-phenyl-chroman-6-yloxy)-N-(isoxazol-5-ylmethyl)cyclohexanecarboxamide | E | 467.1 | 1.36 | 1.9 |
| 293 | 4-(5-Chloro-2-phenyl-chroman-6-yloxy)-N-[(2-ethyl-2H-pyrazol-3-yl)methyl]cyclohexanecarboxamide | E | 494.12 | 1.36 | 4.7 |
| 294 | 4-[2-(2-Fluoro-3-methoxy-phenyl)chroman-6-yloxy]-N-(2-hydroxyethyl)cyclohexanecarboxamide | B | 444.23 | 4.28 | 1.3 |

TABLE 1-continued

Example compounds of the formula I

| Ex. no. | Compound name | LC/ MS | MS (1) | Rt | NCX1rv IC$_{50}$ |
|---|---|---|---|---|---|
| 295 | 4-[2-(2-Fluoro-3-methoxy-phenyl)chroman-6-yloxy]-N-(isoxazol-5-ylmethyl)cyclohexanecarboxamide | B | 481.18 | 4.68 | 1.1 |
| 296 | N-(2-Ethyl-2H-pyrazol-3-ylmethyl)-4-[2-(2-fluoro-3-methoxy-phenyl)chroman-6-yloxy]-cyclohexanecarboxamide | E | 508.2 | 1.30 | 0.9 |
| 297 | N-(2-Ethyl-2H-pyrazol-3-ylmethyl)-4-(3-methyl-2-phenyl-chroman-6-yloxy)-cyclohexanecarboxamide | E | 474.22 | 1.34 | 0.5 |
| 298 | N-(Isoxazol-5-ylmethyl)-4-(3-methyl-2-phenyl-chroman-6-yloxy)-cyclohexanecarboxamide | E | 447.15 | 1.34 | 1.4 |
| 299 | N-(2-Hydroxyethyl)-4-(3-methyl-2-phenyl-chroman-6-yloxy)-cyclohexanecarboxamide | E | 410.15 | 1.28 | 1.9 |
| 300 | N-(2-Ethyl-2H-pyrazol-3-ylmethyl)-4-[2-(3-fluoro-2-methoxy-phenyl)chroman-6-yloxy]-cyclohexanecarboxamide | E | 508.18 | 1.34 | 0.4 |
| 301 | 4-[2-(3-Fluoro-2-methoxy-phenyl)chroman-6-yloxy]-N-(isoxazol-5-ylmethyl)cyclohexanecarboxamide | E | 481.12 | 1.33 | 0.2 |
| 302 | 4-[2-(3-Fluoro-2-methoxy-phenyl)chroman-6-yloxy]-N-(2-hydroxyethyl)cyclohexanecarboxamide | E | 444.14 | 1.27 | 0.4 |
| 303 | Phosphoric acid mono-(2-{[trans-4-((S)-2-o-tolyl-chroman-6-yloxy)-cyclohexanecarbonyl]-amino}-ethyl) ester disodium salt | E | 490.28 | 1.22 | 0.1 |
| 304 | (1R,3R)-3-(2-Phenylchroman-6-yloxy)cyclopentylamine hydrochloride | A | 310.18 | 0.96 | 0.6 |
| 305 | [3-(2-Phenylchroman-6-yloxy)cyclopentylmethyl]amine hydrochloride | E | 323.97 | 0.98 | 1.5 |
| 306 | cis-3-(2-Phenylchroman-6-yloxy)cyclobutylamine hydrochloride | E | 296.3 | 0.96 | 1.6 |

(1) Observed ion [M + H]$^+$, unless specified otherwise
(2) In case a compound has been obtained as stereoisomer 1 and stereoisomer 2, one of them has R configuration, and the other S configuration, with respect to position 2 in the chroman ring
(3) Inhibition in % at 10 µM; IC$_{50}$ value not determined Exemplary NMR data of example compounds.

Example No. 156

$^1$H-NMR (400 MHz): δ (ppm)=1.41 (4H, m), 1.98 (3H, m), 2.11 (3H, m), 2.35 (3H, s), 2.75 (1H, m), 3.02 (2H, m), 4.12 (1H, m), 5.15 (1H, dd), 6.74 (3H, m), 7.24 (3H, m), 7.41 (1H, m).

Example No. 158

$^1$H-NMR (400 MHz): δ (ppm)=1.28 (2H, m), 1.54 (2H, m), 1.88 (3H, m), 2.11 (3H, m), 2.22 (1H, m), 2.32 (3H, s), 2.75 (1H, m), 2.96 (1H, m), 4.12 (1H, m), 4.42 (2H, d), 5.17 (1H dd), 6.28 (1H, s), 6.72 (3H, m), 7.21 (3H, m), 7.43 (1H, m), 8.48 (2H, m).

Example No. 159

$^1$H-NMR: δ (ppm)=1.47 (4H, m), 1.90 (2H, m), 2.00 (3H, m), 2.15 (1H, m), 2.70 (1H, m), 2.95 (1H, m), 3.54 (2H, m), 3.67 (1H, m), 4.16 (1H, m), 5.05 (1H, dd), 6.72 (3H, m), 7.38 (1H, m), 7.41 (4H, m), 8.48 (1H, d).

Example No. 177

$^1$H-NMR: δ (ppm)=1.40 (1H, m), 1.58 (2H, m), 1.78, (1H, m), 1.98 (3H, m), 2.18 (7H, m), 2.25 (3H, s), 2.35 (3H, s), 2.77 (1H, m), 3.03 (1H, m), 3.19, (1H, m), 3.97 (2H, m), 4.13 (0.5H, m), 4.48 (0.5H, m), 5.17 (1H, dd), 6.73 (3H, m), 7.22 (3H, m), 7.40 (1H, m).

Example No. 180

$^1$H-NMR: δ (ppm)=1.48 (4H, m), 1.95 (8H, m), 2.15 (1H, m), 2.28 (1H, m), 2.70 (1H, m), 2.93 (1H, m), 3.22 (1H, m), 3.51 (2H, m), 3.65 (1H, m), 4.10 (1H, t), 4.18 (1H, m), 5.05 (1H, dd), 6.73 (3H, m), 7.42 (1H, m), 7.40 (4H, m) 8.45 (1H, d).

Example No. 268

$^1$H-NMR (400 MHz): δ (ppm)=1.28 (2H, m), 1.48 (2H, m), 1.74 (2H, m), 1.88 (1H, m), 2.11 (4H, m), 2.32 (3H, s), 2.38 (1H, m), 2.73 (1H, dd), 2.96 (1H, m), 3.12 (2H, dt), 3.38 (4H, m), 4.12 (1H, m), 4.68 (1H, t), 5.17 (1H, dd), 6.72 (3H), 7.21 (3H), 7.43 (1H), 7.79 (1H, t).

Example No. 303

$^1$H-NMR (400 MHz, D$_2$O): δ (ppm)=1.45 (4H, m), 1.93 (2H, m), 2.08 (1H, m), 2.18 (3H, m) 2.30 (1H, m) 2.81 (1H, m), 3.02 (1H, m), 3.35 (2H, t), 3.80 (2H, m), 4.42 (1H, m), 5.30 (1H, dd), 6.81 (2H, m), 6.90 (1H, m), 7.29 (3H, m), 7.48 (1H, m).

Pharmacological Examples

A) Assay Method for Determining the NCX1 Inhibitory Activity

The sodium/calcium exchanger NCX1 can transport calcium ions and sodium ions through the cell membrane. The transport is an exchange of Ca$^{2+}$ and Na$^+$ in two directions depending on membrane potential and ion gradients. At the first direction, named "forward mode" or "calcium export mode", $Ca^{2+}$ is transported out of the cell and $Na^+$ is transported into the cell. At the other direction, named "reverse mode" or "calcium import mode", the transport directions are vice versa. The effect of the compounds of the invention on NCX1 was determined in CHO cells stably expressing human NCX1 (gene symbol SLC8A1; cf. WO 2009/115238). The assay is based on the monitoring of intracellular $Ca^{2+}$ concentrations using a calcium-sensitive fluorescence dye which is detected by means of a FLIPR device (Fluorimetric Imaging Plate Reader, Molecular Devices).

Assay Technology—Reverse Mode

The assay is based on the monitoring of intracellular $Ca^{2+}$ concentrations using the calcium-sensitive dye Fluo-4. CHO cells expressing NCX1 were loaded with the dye by means of the acetoxymethyl ester Fluo-4 AM (Invitrogen, F14202), which is cleaved intracellularly by esterase activity to yield the charged species of free Fluo-4. After an preincubation period with the test compound, Gramicidine (Sigma, G5002) was added. Gramicidine is an ionophor for $Na^+$ ions mediating an increase of intracellular $Na^+$ ions. Consequently, intracellular $Na^+$ ions are exchanged against extracellular $Ca^{2+}$ ions ($Ca^{2+}$ influx, reverse mode). The intracellular elevation of $Ca^{2+}$ ions was detected by measuring the fluorescence of Fluo-4 at a wavelength of 520 nm by a FLIPR device.

Briefly, for the reverse mode transport assay 18000 cells per well were seeded into a 96 well microplate (Corning COSTAR 3904) and incubated overnight in culture medium (1× Nut Mix F12 (Ham) (Gibco, 21765-029); 10% (v/v) fetal calf serum (PAA Gold, A15-649); 450 µg/ml Geneticin (Gibco, 10131-027)). A total volume of 100 µl medium per well was used. For the preparation of the FLIPR assay, the culture medium was removed from the plates and 100 µl of dye solution (2 µM Fluo-4 AM; 0.02% (v/v) Pluronic F-127 (20%, Invitrogen, P3000MP); 0.1% (v/v) bovine albumin solution (30% (v/v), Sigma, A9205) in assay buffer (133.8 mM NaCl (Sigma, S5886); 4.7 mM KCl (Sigma, P3911); 1.25 mM $MgCl_2$ (Merck, 1.05833.0250); 3.5 mM $CaCl_2$ (Merck, 1.02083.0250); 5 mM glucose (Sigma, G7021); 10 mM Hepes (Sigma, H4034); 0.01% (v/v) Pluronic F-127 (5%, Sigma, P2443); 2.5 mM Probenecid (Maybridge, SB00915EB); pH 7.4)) were added into each well. The plates were incubated in the dark at room temperature for 80 min. After the incubation period, the dye solution was removed and the wells were washed with 100 µl of assay buffer. Then 80 µl of a solution of the test compound in assay buffer in different concentrations were added into the wells. The plates were incubated at 16° C. for 45 min. Meanwhile a 60 µM solution of Gramicidine in assay buffer (4° C.) was prepared and stored in the wells of a 96 well microplate (96 well microplate, polypropylene, U-shape (Greiner Bio-One, 650201)) at 4° C. until measurement was started. The fluorescence monitoring was performed at 240 measuring points with measurement intervals of 2 sec. After the fifth measuring point, 40 µl of the Gramicidine solution were added to each well of the assay plates to give a final Gramicidine concentration of 20 µM. For the determination of the $IC_{50}$ values the minimal fluorescence value was subtracted from the maximal fluorescence value for all measuring points. The calculation of the $IC_{50}$ values via the percentage inhibitions of $Ca^{2+}$ influx into cells (reverse mode) effected by the test compound was performed in Biost@t Speed 2.0. Results obtained with compounds of the invention are given in Table 1.

Assay Technology—Forward Mode

The assay is based on the monitoring of intracellular $Ca^{2+}$ concentrations using the PBX Calcium Assay Kit from BD (Becton, Dickinson and Company) with calcium indicator dye 51-9000177BKa (BD, 640177). CHO cells expressing NCX1 were loaded with the dye, and after a preincubation period with the test compound, Ionomycin (Calbiochem, 407950) was added. Ionomycin is an ionophor for $Ca^{2+}$ ions mediating an increase of intracellular $Ca^{2+}$ ions. Consequently, intracellular $Ca^{2+}$ ions are exchanged against extracellular $Na^+$ ions ($Ca^{2+}$ efflux, forward mode). The decrease of intracellular $Ca^{2+}$ ions was detected by measuring the fluorescence of the calcium indicator dye at a wavelength of 520 nm by a FLIPR device.

Briefly, similarly as for the reverse mode, for the forward mode transport assay 18000 cells per well were seeded into a 96 well microplate (Corning COSTAR 3904) and incubated overnight in culture medium (cf. above). A total volume of 100 µl medium per well was used. For the preparation of the FLIPR assay, the culture medium was removed from the plates and 100 µl of assay buffer (133.8 mM NaCl (Sigma, S5886); 4.7 mM KCl (Sigma, P3911); 1.25 mM $MgCl_2$ (Merck, 1.05833.0250); 3.5 mM $CaCl_2$ (Merck, 1.02083.0250); 5 mM glucose (Sigma, G7021); 10 mM Hepes (Sigma, H4034); pH 7.4)) were added to each well in a washing step. Assay buffer was removed, and 100 µl of a solution of the test compound in assay buffer in different concentrations were added into the wells. Further, 100 µl of dye solution (0.09% (v/v) calcium indicator dye, 9.1% (v/v) signal enhancer (from PBX Calcium Assay Kit); in assay buffer) were added into each well. The plates were incubated in the dark at room temperature for 60 min. Meanwhile a 10 µM solution of Ionomycin in assay buffer (additionally containing 0.05% fetal calf serum (cf. above); 4° C.) was prepared and stored in the wells of a 96 well microplate (96 well microplate, polypropylene, U-shape (Greiner Bio-One, 650201)). The fluorescence monitoring was performed at 60 measuring points with measurement intervals of 2 sec. After the fifth measuring point, 50 µl of the Ionomycin solution were added to each well of the assay plate to give a final Ionomycin concentration of 2 µM. For the determination of the $IC_{50}$ values the minimal fluorescence value was subtracted from the maximal fluorescence value for the fifteenth to fifty-fifth measuring points. The calculation of the $IC_{50}$ values via the percentage inhibitions of $Ca^{2+}$ efflux out of cells (forward mode) effected by the test compound was performed in Biost@t Speed 2.0. Results obtained with compounds of the invention are given in Table 2. "NCX1fw $IC_{50}$" in Table 2 means the $IC_{50}$ value (in µM (micromol/liter)) for inhibition of NCX1 in forward mode.

TABLE 2

| $IC_{50}$ values for inhibition of the NCX1 in forward mode by example compounds | |
|---|---|
| Example number | NCX1fw $IC_{50}$ |
| 156 | 1.5 |
| 158 | 2.2 |
| 159 | 2.5 |
| 177 | 0.2 |
| 180 | 10 |
| 267 | 4.4 |
| 268 | 0.5 |
| 269 | 3.1 |
| 270 | 1.0 |
| 303 | 2.5 |

B) In Vivo Method for Determining the Effect on Heart Contractility

Adult male Sprague-Dawley rats (Harlan Winkelmann, Borchen, Germany) weighing 340 to 370 g were anesthetized with pentobarbital (100 mg/kg i.p.) and ventilated with a mixture of oxygen (40%) and room air (60%) at a tidal volume of 1 ml/100 g at 60 breaths/min. Body temperature was maintained at 36.5±0.3° C. with a heating lamp and was monitored with a rectal thermo sensor. Systemic blood pressure was measured in the left carotid artery using a pressure transducer (Combitrans; B. Braun Melsungen AG, Melsungen, Germany) connected to a DC-bridge-amplifier (PLUGSYS/ADC Type 663; Harvard Apparatus GmbH, March-Hugstetten, Germany). The electrocardiogram was measured as lead II via subcutaneously placed electrodes connected to a Heart-Rate-Module (PLUGSYS/HRM Type 669; Harvard Apparatus GmbH, March-Hugstetten, Germany). A micro-tip catheter (2 French, SPR-320; Millar Instruments, Houston, Tex., USA) was placed via the right carotid artery into the left ventricle, and the left ventricular pressure (LVP) and the enddiastolic pressure (EDP) were continuously measured. Registration of the hemodynamic data was performed via an analog digital converter by a personal computer using Notocord software (HEM version 3.5). Left ventricular contractility ($dp/dt_{max}$) and relaxation ($dp/dt_{min}$) were calculated from the LVP signal. For intravenous administration of the test compounds, the left jugular vein was prepared and a PP-50 catheter was inserted. Test compounds were administered either by intravenous bolus injection or by intravenous infusion by means of an infusion pump (Unita; B. Braun Melsungen AG, Melsungen, Germany). Test compounds were dissolved in a mixture of Glycofurol (75%) and Cremophor (25%), and the solution was further diluted with distilled water (1:4). In a typical experiment, several dosages of the test compound were administered subsequently at increasing doses. Statistical significance of the data obtained with drug vs control experiments, in which solvent was administered, was evaluated with the 2-sided ANOVA test (program Everstat). Increases in left ventricular contractility (percent increase) by example compounds are given in Table 3 in comparison to control experiments in which solvent was administered.

TABLE 3

Increase in left ventricular contractility by example compounds

| Example number | Dose (mg per kg of body weight) | Contractility increase (%) |
|---|---|---|
| 156 | 0.1 mg/kg | 44% |
| | 0.3 mg/kg | 110% |
| | 1.0 mg/kg | 171% |
| 158 | 0.1 mg/kg | 106% |
| | 0.3 mg/kg | 139% |
| | 1.0 mg/kg | 146% |
| 159 | 0.1 mg/kg | 46% |
| | 0.3 mg/kg | 104% |
| | 1.0 mg/kg | 140% |
| 177 | 0.1 mg/kg | 29% |
| | 0.3 mg/kg | 81% |
| | 1.0 mg/kg | 134% |
| 180 | 0.1 mg/kg | 26% |
| | 0.3 mg/kg | 66% |
| | 1.0 mg/kg | 99% |
| 268 | 0.1 mg/kg | 108% |
| | 0.3 mg/kg | 154% |
| | 1.0 mg/kg | 179% |
| 303 | 0.1 mg/kg | 69% |
| | 0.3 mg/kg | 114% |
| | 1.0 mg/kg | 172% |

What is claimed is:

1. A compound of the formula I, in any of its stereoisomeric forms or a mixture of stereoisomeric forms in any ratio, or a pharmaceutically acceptable salt thereof,

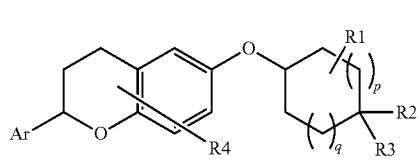

wherein
Ar is phenyl which is unsubstituted or substituted by one or more identical or different substituents R0;
R0 is selected from the series consisting of halogen, ($C_1$-$C_6$)-alkyl, ($C_3$-$C_7$)-cycloalkyl, ($C_3$-$C_7$)-cycloalkyl-($C_1$-$C_4$)-alkyl-, HO—, ($C_1$-$C_6$)-alkyl-O—, ($C_3$-$C_7$)-cycloalkyl-O— and ($C_3$-$C_7$)-cycloalkyl-($C_1$-$C_4$)-alkyl-O—, and two groups R0 bonded to adjacent ring carbon atoms in Ar, together with the carbon atoms carrying them, can form a 5-membered to 7-membered monounsaturated ring which comprises 0, 1 or 2 identical or different ring heteroatoms selected from the series consisting of nitrogen, oxygen and sulfur, and which is unsubstituted or substituted by one or more identical or different substituents selected from the series consisting of fluorine and ($C_1$-$C_4$)-alkyl;
R1 is hydrogen or one or more identical or different substituents selected from the series consisting of fluorine and ($C_1$-$C_4$)-alkyl;
R2 is selected from the series consisting of hydrogen, ($C_1$-$C_6$)-alkyl, HO—, ($C_1$-$C_6$)-alkyl-O—, ($C_1$-$C_6$)-alkyl-C(O)—O—, phenyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, wherein ($C_1$-$C_6$)-alkyl is unsubstituted or substituted by one or more identical or different substituents R20;
R3 is selected from the series consisting of hydrogen and ($C_1$-$C_6$)-alkyl, wherein ($C_1$-$C_6$)-alkyl is unsubstituted or substituted by one or two identical or different substituents selected from the series consisting of ($C_3$-$C_7$)-cycloalkyl, phenyl, HO— and ($C_1$-$C_4$)-alkyl-O—;
or the groups R2 and R3 together are oxo;
R4 is hydrogen or one or more identical or different substituents selected from the series consisting of halogen, ($C_1$-$C_4$)-alkyl and ($C_1$-$C_4$)-alkyl-O—;
R5 and R6 are independently of one another selected from the series consisting of hydrogen, ($C_1$-$C_6$)-alkyl, ($C_2$-$C_6$)-alkenyl, ($C_3$-$C_7$)-cycloalkyl, ($C_6$-$C_{10}$)-bicycloalkyl, phenyl, Het1 and Het2, wherein ($C_1$-$C_6$)-alkyl is unsubstituted or substituted by one or more identical or different substituents R20, and ($C_3$-$C_7$)-cycloalkyl, ($C_6$-$C_{10}$)-bicycloalkyl and Het2 all are unsubstituted or substituted by one or more identical or different substituents R21, and phenyl and Het1 all are unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of $(C_1-C_6)$-alkyl, $(C_3-C_7)$-cycloalkyl, phenyl, Het1 and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, and phenyl and Het1 all are unsubstituted or substituted by one or more identical or different substituents R22;

R8 is selected from the series consisting of hydrogen and $(C_1-C_4)$-alkyl;

R9 is selected from the series consisting of $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R10 is selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R20 is selected from the series consisting of R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R22 is selected from the series consisting of halogen, $(C_1-C_4)$-alkyl, HO—$(C_1-C_4)$-alkyl-, $(C_3-C_7)$-cycloalkyl, HO—, oxo, $(C_1-C_6)$-alkyl-O—, $(C_3-C_7)$-cycloalkyl-O—, HO—S(O)$_2$—O—, (HO)$_2$P(O)—O—, (HO)$_2$P(O)—O—CH$_2$—O—C(O)—O—, $(C_1-C_6)$-alkyl-S(O)$_n$—, $(C_3-C_7)$-cycloalkyl-S(O)$_n$—, R31-N(R32)-, R33-C(O)—N(R32)-, R33-O—C(O)—N(R32)-, $(C_1-C_6)$-alkyl-S(O)$_2$—N(R32)-, NC—, R33-C(O)—, R31-N(R32)-C(O)—, R34-O—C(O)— and R31-N(R32)-S(O)$_2$—;

R24 is a 3-membered to 10-membered, monocyclic or bicyclic ring which is saturated, partially unsaturated or aromatic and comprises 0, 1, 2, 3 or 4 identical or different ring heteroatoms selected from the series consisting of nitrogen, oxygen and sulfur, and which is unsubstituted or substituted by one or more identical or different substituents R22;

R30 and R33 are independently of one another selected from the series consisting of $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

R31 and R32 are independently of one another selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-, or the groups R31 and R32, together with the nitrogen atom carrying them, form a 4-membered to 7-membered, monocyclic saturated heterocycle which, in addition to the nitrogen atom carrying R31 and R32, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl;

R34 is selected from the series consisting of hydrogen, $(C_1-C_6)$-alkyl, $(C_3-C_7)$-cycloalkyl, $(C_3-C_7)$-cycloalkyl-$(C_1-C_4)$-alkyl-, phenyl-$(C_1-C_4)$-alkyl- and Het1-$(C_1-C_4)$-alkyl-;

Het1 is a 5-membered or 6-membered, monocyclic, aromatic heterocycle which comprises 1, 2 or 3 identical or different ring heteroatoms selected from the series consisting of nitrogen, oxygen and sulfur, and which is unsubstituted or substituted by one or more identical or different substituents selected from the series consisting of halogen, $(C_1-C_4)$-alkyl and $(C_1-C_4)$-alkyl-O—, unless specified otherwise;

Het2 is a 4-membered to 10-membered, monocyclic or bicyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, $(C_1-C_4)$-alkyl and $(C_1-C_4)$-alkyl-O—, unless specified otherwise;

wherein all cycloalkyl and bicycloalkyl groups, independently of any other substituents which can be present on a cycloalkyl or bicycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

2. A compound of the formula I, in any of its stereoisomeric forms or a mixture of stereoisomeric forms in any ratio, or a pharmaceutically acceptable salt thereof, according to claim 1, wherein Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_3-C_7)$-cycloalkyl-$(C_1-C_4)$-alkyl-, HO—, $(C_1-C_6)$-alkyl-O—, $(C_3-C_7)$-cycloalkyl-O— and $(C_3-C_7)$-cycloalkyl-$(C_1-C_4)$-alkyl-O;

R1 is hydrogen or one or more identical or different substituents selected from the series consisting of fluorine and $(C_1-C_4)$-alkyl;

R2 is selected from the series consisting of $(C_1-C_6)$-alkyl, HO—, $(C_1-C_6)$-alkyl-O—, $(C_1-C_6)$-alkyl-C(O)—O—, Het1-C(O)—O—, R5-N(R6)-, R7-C(O)—N(R8)-, R7-S(O)$_2$—N(R8)-, R9-N(R10)-C(O)—N(R8)- and R5-N(R6)-C(O)—, wherein (C$_1$-C$_6$)-alkyl is unsubstituted or substituted by one or more identical or different substituents R20;

R3 is selected from the series consisting of hydrogen and (C$_1$-C$_6$)-alkyl, wherein (C$_1$-C$_6$)-alkyl is unsubstituted or substituted by one or two identical or different substituents selected from the series consisting of (C$_3$-C$_7$)-cycloalkyl and phenyl;

or the groups R2 and R3 together are oxo;

R4 is hydrogen or one or more identical or different substituents selected from the series consisting of halogen, (C$_1$-C$_4$)-alkyl and (C$_1$-C$_4$)-alkyl-O—;

R5 and R6 are independently of one another selected from the series consisting of hydrogen, (C$_1$-C$_6$)-alkyl, (C$_2$-C$_6$)-alkenyl, (C$_3$-C$_7$)-cycloalkyl, Het1 and Het2, wherein (C$_1$-C$_6$)-alkyl is unsubstituted or substituted by one or more identical or different substituents R20, and (C$_3$-C$_7$)-cycloalkyl and Het2 all are unsubstituted or substituted by one or more identical or different substituents R21, and Het1 is unsubstituted or substituted by one or more identical or different substituents R22, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of (C$_1$-C$_6$)-alkyl, (C$_3$-C$_7$)-cycloalkyl, phenyl, Het1 and Het2, wherein (C$_1$-C$_6$)-alkyl is unsubstituted or substituted by one or more identical or different substituents R20, and (C$_3$-C$_7$)-cycloalkyl and Het2 all are unsubstituted or substituted by one or more identical or different substituents R21, and phenyl and Het1 all are unsubstituted or substituted by one or more identical or different substituents R22;

R8 is selected from the series consisting of hydrogen and (C$_1$-C$_4$)-alkyl;

R9 is selected from the series consisting of (C$_1$-C$_6$)-alkyl and (C$_3$-C$_7$)-cycloalkyl;

R10 is selected from the series consisting of hydrogen, (C$_1$-C$_6$)-alkyl and (C$_3$-C$_7$)-cycloalkyl;

R20 is selected from the series consisting of R24, fluorine, HO—, oxo, (C$_1$-C$_6$)-alkyl-O—, (C$_3$-C$_7$)-cycloalkyl-O—, R30-C(O)—O—, R30-NH—C(O)—O—, HO—S(O)$_2$—O—, (HO)$_2$P(O)—O—, (HO)$_2$P(O)—O—CH$_2$—O—C(O)—O—, (C$_1$-C$_6$)-alkyl-S(O)$_n$—, (C$_3$-C$_7$)-cycloalkyl-S(O)$_n$—, R31-N(R32)-, R33-C(O)—N(R32)-, (C$_1$-C$_6$)-alkyl-S(O)$_2$—N(R32)-, R31-N(R32)-C(O)—, R34-O—C(O)— and R31-N(R32)-S(O)$_2$—;

R21 is selected from the series consisting of (C$_1$-C$_4$)-alkyl, HO—(C$_1$-C$_4$)-alkyl-, R31-N(R32)-(C$_1$-C$_4$)-alkyl-, R34-O—C(O)—(C$_1$-C$_4$)-alkyl-, R24, fluorine, HO—, oxo, (C$_1$-C$_6$)-alkyl-O—, (C$_3$-C$_7$)-cycloalkyl-O—, R30-C(O)—O—, R30-NH—C(O)—O—, HO—S(O)$_2$—O—, (HO)$_2$P(O)—O—, (C$_1$-C$_6$)-alkyl-S(O)$_n$, R31-N(R32)-, R33-C(O)—N(R32)-, (C$_1$-C$_6$)-alkyl-S(O)$_2$—N(R32)- and R31-N(R32)-C(O)—;

R22 is selected from the series consisting of halogen, (C$_1$-C$_4$)-alkyl, HO—(C$_1$-C$_4$)-alkyl-, (C$_3$-C$_7$)-cycloalkyl, HO—, oxo, (C$_1$-C$_6$)-alkyl-O—, (C$_3$-C$_7$)-cycloalkyl-O—, HO—S(O)$_2$—O—, (HO)$_2$P(O)—O—, (C$_1$-C$_6$)-alkyl-S(O)$_n$, R31-N(R32)-, R33-C(O)—N(R32)-, R33-O—C(O)—N(R32)-, (C$_1$-C$_6$)-alkyl-S(O)$_2$—N(R32)-, NC—, R33-C(O)— and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R30 and R33 are independently of one another selected from the series consisting of (C$_1$-C$_6$)-alkyl, (C$_3$-C$_7$)-cycloalkyl, (C$_3$-C$_7$)-cycloalkyl-(C$_1$-C$_4$)-alkyl-, phenyl-(C$_1$-C$_4$)-alkyl- and Het1-(C$_1$-C$_4$)-alkyl-;

R31 and R32 are independently of one another selected from the series consisting of hydrogen, (C$_1$-C$_6$)-alkyl, (C$_3$-C$_7$)-cycloalkyl, (C$_3$-C$_7$)-cycloalkyl-(C$_1$-C$_4$)-alkyl-, phenyl-(C$_1$-C$_4$)-alkyl- and Het1-(C$_1$-C$_4$)-alkyl-;

R34 is selected from the series consisting of hydrogen, (C$_1$-C$_6$)-alkyl, (C$_3$-C$_7$)-cycloalkyl and (C$_3$-C$_7$)-cycloalkyl-(C$_1$-C$_4$)-alkyl-;

Het1 is a 5-membered or 6-membered, monocyclic, aromatic heterocycle which comprises 1, 2 or 3 identical or different ring heteroatoms selected from the series consisting of nitrogen, oxygen and sulfur, and which is unsubstituted or substituted by one or more identical or different substituents selected from the series consisting of halogen, (C$_1$-C$_4$)-alkyl and (C$_1$-C$_4$)-alkyl-O—, unless specified otherwise;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, (C$_1$-C$_4$)-alkyl and (C$_1$-C$_4$)-alkyl-O—, unless specified otherwise;

wherein all cycloalkyl groups, independently of any other substituents which can be present on a cycloalkyl group, can be substituted by one or more identical or different substituents selected from the series consisting of fluorine and (C$_1$-C$_4$)-alkyl;

wherein all alkyl groups, independently of any other substituents which can be present on an alkyl group, can be substituted by one or more fluorine substituents.

3. A compound of the formula I, in any of its stereoisomeric forms or a mixture of stereoisomeric forms in any ratio, or a pharmaceutically acceptable salt thereof, according to claim 1, wherein Ar is phenyl which is unsubstituted or substituted by one or more identical or different substituents R0;

R0 is selected from the series consisting of halogen, (C$_1$-C$_6$)-alkyl, (C$_3$-C$_7$)-cycloalkyl, (C$_3$-C$_7$)-cycloalkyl-(C$_1$-C$_4$)-alkyl-, HO—, (C$_1$-C$_6$)-alkyl-O—, (C$_3$-C$_7$)-cycloalkyl-O— and (C$_3$-C$_7$)-cycloalkyl-(C$_1$-C$_4$)-alkyl-O—;

R1 is hydrogen or one or more identical or different substituents selected from the series consisting of fluorine and (C$_1$-C$_4$)-alkyl;

R2 is selected from the series consisting of $(C_1-C_6)$-alkyl, HO—, $(C_1-C_6)$-alkyl-O—, R5-N(R6)-, R7-C(O)—N(R8)-, R9-N(R10)-C(O)—N(R8)- and R5-N(R6)-C(O)—, wherein $(C_1-C_6)$-alkyl is unsubstituted or substituted by one or more identical or different substituents R20;

R3 is selected from the series consisting of hydrogen and $(C_1-C_6)$-alkyl, wherein $(C_1-C_6)$-alkyl is unsubstituted or substituted by one or two identical or different substituents selected from the series consisting of $(C_3-C_7)$-cycloalkyl and phenyl;

or the groups R2 and R3 together are oxo;

R4 is hydrogen or one or more identical or different substituents selected from the series consisting of halogen, $(C_1-C_4)$-alkyl and $(C_1-C_4)$-alkyl-O—;

R5 and R6 are independently of one another selected from the series consisting of hydrogen, $(C_1-C_6)$-alkyl, $(C_3-C_7)$-cycloalkyl and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21, or the groups R5 and R6, together with the nitrogen atom carrying them, form a 4-membered to 7-membered, monocyclic, saturated or partially unsaturated heterocycle which, in addition to the nitrogen atom carrying R5 and R6, comprises 0 or 1 further ring heteroatom selected from the series consisting of nitrogen, oxygen and sulfur, and which is unsubstituted or substituted by one or more identical or different substituents R21;

R7 is selected from the series consisting of $(C_1-C_6)$-alkyl, $(C_3-C_7)$-cycloalkyl and Het2, wherein $(C_1-C_6)$-alkyl is unsubstituted or substituted by one or more identical or different substituents R20, and $(C_3-C_7)$-cycloalkyl and Het2 all are unsubstituted or substituted by one or more identical or different substituents R21;

R8 is selected from the series consisting of hydrogen and $(C_1-C_4)$-alkyl;

R9 is selected from the series consisting of $(C_1-C_6)$-alkyl and $(C_3-C_7)$-cycloalkyl;

R10 is selected from the series consisting of hydrogen, $(C_1-C_6)$-alkyl and $(C_3-C_7)$-cycloalkyl-;

R20 is selected from the series consisting of R24, fluorine, HO—, oxo, $(C_1-C_6)$-alkyl-O—, $(C_3-C_7)$-cycloalkyl-O—, R30-C(O)—O—, R30-NH—C(O)—O—, HO—S(O)$_2$—O—, (HO)$_2$P(O)—O—, $(C_1-C_6)$-alkyl-S(O)$_n$, R31-N(R32)-, R33-C(O)—N(R32)-, $(C_1-C_6)$-alkyl-S(O)$_2$—N(R32)-, R31-N(R32)-C(O)—, R34-O—C(O)— and R31-N(R32)-S(O)$_2$—;

R21 is selected from the series consisting of $(C_1-C_4)$-alkyl, HO—$(C_1-C_4)$-alkyl-, R31-N(R32)-$(C_1-C_4)$-alkyl-, R34-O—C(O)—$(C_1-C_4)$-alkyl-, R24, fluorine, HO—, $(C_1-C_6)$-alkyl-O—, $(C_3-C_7)$-cycloalkyl-O—, HO—S(O)$_2$—O—, (HO)$_2$P(O)—O—, $(C_1-C_6)$-alkyl-S(O)$_n$—, R31-N(R32)-, R33-C(O)—N(R32)- and R31-N(R32)-C(O)—;

R22 is selected from the series consisting of halogen, $(C_1-C_4)$-alkyl, HO—$(C_1-C_4)$-alkyl-, $(C_3-C_7)$-cycloalkyl, HO—, $(C_1-C_6)$-alkyl-O—, $(C_3-C_7)$-cycloalkyl-O—, HO—S(O)$_2$—O—, (HO)$_2$P(O)—O—, $(C_1-C_6)$-alkyl-S(O)$_n$, R31-N(R32)-, R33-C(O)—N(R32)-, NC—, R33-C(O)— and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R30 and R33 are independently of one another selected from the series consisting of $(C_1-C_6)$-alkyl, $(C_3-C_7)$-cycloalkyl and $(C_3-C_7)$-cycloalkyl-$(C_1-C_4)$-alkyl-;

R31 and R32 are independently of one another selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

R34 is selected from the series consisting of hydrogen, $(C_1-C_6)$-alkyl, $(C_3-C_7)$-cycloalkyl and $(C_3-C_7)$-cycloalkyl-$(C_1-C_4)$-alkyl-;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are independently of one another selected from the series consisting of 0 and 1;

wherein all phenyl groups are unsubstituted or substituted by one or more identical or different substituents selected from the series consisting of halogen, $(C_1-C_4)$-alkyl and $(C_1-C_4)$-alkyl-O—, unless specified otherwise;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

4. A compound of the formula I, in any of its stereoisomeric forms or a mixture of stereoisomeric forms in any ratio, or a pharmaceutically acceptable salt thereof, according to claim 1, wherein Ar is phenyl which is unsubstituted or substituted by one or more identical or different substituents R0;

R0 is selected from the series consisting of halogen, $(C_1-C_6)$-alkyl, $(C_3-C_7)$-cycloalkyl, $(C_1-C_6)$-alkyl-O— and $(C_3-C_7)$-cycloalkyl-O—;

R1 is hydrogen or one or more identical or different substituents selected from the series consisting of fluorine and $(C_1-C_4)$-alkyl;

R2 is selected from the series consisting of $(C_1-C_6)$-alkyl, HO—, R5-N(R6)-, R7-C(O)—N(R8)- and R5-N(R6)-C(O)—, wherein $(C_1-C_6)$-alkyl is unsubstituted or substituted by one or more identical or different substituents R20;

R3 is hydrogen;

R4 is hydrogen or one or more identical or different substituents selected from the series consisting of halogen and $(C_1-C_4)$-alkyl;

one of the groups R5 and R6 is selected from the series consisting of hydrogen and $(C_1-C_6)$-alkyl, and the other of the groups R5 and R6 is selected from the series consisting of $(C_1-C_6)$-alkyl, $(C_3-C_7)$-cycloalkyl and Het2, wherein $(C_1-C_6)$-alkyl all are unsubstituted or substituted by one or more identical or different substituents R20, and $(C_3-C_7)$-cycloalkyl and Het2 all are unsubstituted or substituted by one or more identical or different substituents R21;

R7 is selected from the series consisting of $(C_1-C_6)$-alkyl, $(C_3-C_7)$-cycloalkyl and Het2, wherein $(C_1-C_6)$-alkyl is unsubstituted or substituted by one or more identical or different substituents R20, and ($C_3$-$C_7$)-cycloalkyl and Het2 all are unsubstituted or substituted by one or more identical or different substituents R21;

R8 is selected from the series consisting of hydrogen and ($C_1$-$C_4$)-alkyl;

R20 is selected from the series consisting of R24, fluorine, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)-, R31-N(R32)-C(O)— and R31-N(R32)-S(O)$_2$—;

R21 is selected from the series consisting of ($C_1$-$C_4$)-alkyl, HO—($C_1$-$C_4$)-alkyl-, R31-N(R32)-($C_1$-$C_4$)-alkyl-, fluorine, HO—, ($C_1$-$C_6$)-alkyl-O—, ($C_3$-$C_7$)-cycloalkyl-O—, HO—S(O)$_2$—O—, (HO)$_2$P(O)—O—, R31-N(R32)-, R33-C(O)—N(R32)- and R31-N(R32)-C(O)—;

R22 is selected from the series consisting of halogen, ($C_1$-$C_4$)-alkyl, HO—($C_1$-$C_4$)-alkyl-, ($C_3$-$C_7$)-cycloalkyl, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)- and R31-N(R32)-C(O)—;

R24 is a 3-membered to 7-membered, monocyclic ring which is saturated, partially unsaturated or aromatic and comprises 0, 1, 2 or 3 identical or different ring heteroatoms selected from the series consisting of nitrogen, oxygen and sulfur, and which is unsubstituted or substituted by one or more identical or different substituents R22;

R33 is selected from the series consisting of ($C_1$-$C_6$)-alkyl;

R31 and R32 are independently of one another selected from the series consisting of hydrogen, ($C_1$-$C_6$)-alkyl, ($C_3$-$C_7$)-cycloalkyl and ($C_3$-$C_7$)-cycloalkyl-($C_1$-$C_4$)-alkyl-;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are 1;

wherein all cycloalkyl groups, independently of any other substituents which can be present on a cycloalkyl group, can be substituted by one or more identical or different substituents selected from the series consisting of fluorine and ($C_1$-$C_4$)-alkyl;

wherein all alkyl groups, independently of any other substituents which can be present on an alkyl group, can be substituted by one or more fluorine substituents.

5. A compound of the formula I, in any of its stereoisomeric forms or a mixture of stereoisomeric forms in any ratio, or a pharmaceutically acceptable salt thereof, according to claim 1, wherein R2 is selected from the series consisting of R5-N(R6)- and R7-C(O)—N(R8)-.

6. A compound of the formula I, in any of its stereoisomeric forms or a mixture of stereoisomeric forms in any ratio, or a pharmaceutically acceptable salt thereof, according to claim 1, wherein R2 is R5-N(R6)-C(O)—.

7. A compound of the formula I, in any of its stereoisomeric forms or a mixture of stereoisomeric forms in any ratio, or a pharmaceutically acceptable salt thereof, according to claim 1, wherein R3 is hydrogen.

8. A compound of the formula I, in any of its stereoisomeric forms or a mixture of stereoisomeric forms in any ratio, or a pharmaceutically acceptable salt thereof, according to any claim 1, wherein Ar is phenyl which is unsubstituted or substituted by one or two identical or different substituents R0;

R0 is selected from the series consisting of halogen, ($C_1$-$C_6$)-alkyl and ($C_1$-$C_6$)-alkyl-O—;

R1 is hydrogen;

R2 is R5-N(R6)-C(O)—;

R3 is hydrogen;

R4 is hydrogen;

one of the groups R5 and R6 is selected from the series consisting of hydrogen and ($C_1$-$C_6$)-alkyl, and the other of the groups R5 and R6 is selected from the series consisting of ($C_1$-$C_6$)-alkyl, ($C_3$-$C_7$)-cycloalkyl and Het2, wherein ($C_1$-$C_6$)-alkyl all are unsubstituted or substituted by one or more identical or different substituents R20, and ($C_3$-$C_7$)-cycloalkyl and Het2 all are unsubstituted or substituted by one or more identical or different substituents R21;

R20 is selected from the series consisting of R24, fluorine, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)-, ($C_1$-$C_6$)-alkyl-S(O)$_2$—N(R32)- and R31-N(R32)-C(O)—;

R21 is selected from the series consisting of ($C_1$-$C_4$)-alkyl, HO—($C_1$-$C_4$)-alkyl-, R31-N(R32)-($C_1$-$C_4$)-alkyl-, fluorine, HO—, ($C_1$-$C_6$)-alkyl-O—, ($C_3$-$C_7$)-cycloalkyl-O—, HO—S(O)$_2$—O—, (HO)$_2$P(O)—O—, R31-N(R32)-, R33-C(O)—N(R32)- and R31-N(R32)-C(O)—;

R22 is selected from the series consisting of halogen, ($C_1$-$C_4$)-alkyl, HO—($C_1$-$C_4$)-alkyl-, ($C_3$-$C_7$)-cycloalkyl, HO—, ($C_1$-$C_6$)-alkyl-O—, ($C_3$-$C_7$)-cycloalkyl-O—, HO—S(O)$_2$—O—, (HO)$_2$P(O)—O—, ($C_1$-$C_6$)-alkyl-S(O)$_n$—, R31-N(R32)-, R33-C(O)—N(R32)- and R31-N(R32)-C(O)—;

R24 is a 3-membered to 7-membered, monocyclic ring which is saturated, partially unsaturated or aromatic and comprises 0, 1 or 2 identical or different ring heteroatoms selected from the series consisting of nitrogen, oxygen and sulfur, and which is unsubstituted or substituted by one or more identical or different substituents R22;

R33 is selected from the series consisting of ($C_1$-$C_6$)-alkyl;

R31 and R32 are independently of one another selected from the series consisting of hydrogen and ($C_1$-$C_6$)-alkyl;

Het2 is a 4-membered to 7-membered, monocyclic, saturated or partially unsaturated heterocycle which comprises 1 or 2 identical or different ring heteroatoms selected from the series consisting of nitrogen, oxygen and sulfur;

n is selected from the series consisting of 0, 1 and 2, wherein all numbers n are independent of one another;

p and q are 1;

wherein all cycloalkyl groups independently of any other substituents which can be present on a cycloalkyl, can be substituted by one or more identical or different substituents selected from the series consisting of fluorine and ($C_1$-$C_4$)-alkyl;

wherein all alkyl groups, independently of any other substituents which can be present on an alkyl group, can be substituted by one or more fluorine substituents.

9. A compound of the formula I according to claim 1, which is selected from the series consisting of:
- trans-4-(2-o-Tolyl-chroman-6-yloxy)-cyclohexylamine,
- N-(Isoxazol-5-ylmethyl)-4-(2-o-tolyl-chroman-6-yloxy)-cyclohexanecarboxamide,
- 2-Amino-N-[trans-4-((S)-2-phenyl-chroman-6-yloxy)-cyclohexyl]-acetamide,
- 4-(2-o-Tolyl-chroman-6-yloxy)-N-(1,3,5-trimethylpyrazol-4-ylmethyl)-cyclohexylamine,
- (S)—N-[trans-4-(2-Phenyl-chroman-6-yloxy)-cyclohexyl]-pyrrolidine-2-carboxamide,
- trans-4-((R)-2-o-tolyl-chroman-6-yloxy)-cyclohexanecarboxylic acid (2-hydroxy-ethyl)-amide,
- trans-4-((S)-2-o-tolyl-chroman-6-yloxy)-cyclohexanecarboxylic acid (2-hydroxy-ethyl)-amide,
- cis-4-((R)-2-o-tolyl-chroman-6-yloxy)-cyclohexanecarboxylic acid (2-hydroxy-ethyl)-amide,
- cis-4-((S)-2-o-tolyl-chroman-6-yloxy)-cyclohexanecarboxylic acid (2-hydroxy-ethyl)-amide, and
- Phosphoric acid mono-(2-{[trans-4-((S)-2-o-tolyl-chroman-6-yloxy)-cyclohexanecarbonyl]-amino}-ethyl) ester, or a pharmaceutically acceptable salt thereof.

10. A pharmaceutical composition, comprising a compound of the formula I, in any of its stereoisomeric forms or a mixture of stereoisomeric forms in any ratio, or a pharmaceutically acceptable salt thereof, according to claim 1, and a pharmaceutically acceptable carrier.

11. A method of inhibiting sodium-calcium-exchanger (NCX) in a patient in need thereof, the method comprising administering to the patient an effective amount of a compound of claim 1, in any of its stereoisomeric forms or a mixture of stereoisomeric forms in any ratio, or a pharmaceutically acceptable salt thereof.

12. A method of treating heart failure, cardiac arrhythmia, stroke, dementia, hypertension, cardiac ischemia, renal failure or shock in a patient in need thereof, the method comprising administering to the patient an effective dose of a compound of claim 1, in any of its stereoisomeric forms or a mixture of stereoisomeric forms in any ratio, or a pharmaceutically acceptable salt thereof.

13. A method of inhibiting sodium-calcium-exchanger (NCX) of a cell, the method comprising contacting the cell with a compound of claim 1, in any of its stereoisomeric forms or a mixture of stereoisomeric forms in any ratio, or a pharmaceutically acceptable salt thereof.

14. A compound of the formula I according to claim 1, which is trans-4-((R)-2-o-tolyl-chroman-6-yloxy)-cyclohexanecarboxylic acid (2-hydroxy-ethyl)-amide.

15. A compound of the formula I according to claim 1, which is trans-4-((S)-2-o-tolyl-chroman-6-yloxy)-cyclohexanecarboxylic acid (2-hydroxy-ethyl)-amide.

16. A compound of the formula I according to claim 1, which is cis-4-((R)-2-o-tolyl-chroman-6-yloxy)-cyclohexanecarboxylic acid (2-hydroxy-ethyl)-amide.

17. A compound of the formula I according to claim 1, which is cis-4-((S)-2-o-tolyl-chroman-6-yloxy)-cyclohexanecarboxylic acid (2-hydroxy-ethyl)-amide.

18. A compound of the formula I according to claim 1, which is phosphoric acid mono-(2-{[trans-4-((S)-2-o-tolyl-chroman-6-yloxy)-cyclohexanecarbonyl]-amino}-ethyl) ester, or a pharmaceutically acceptable salt thereof.

* * * * *